US008865743B2

(12) United States Patent  
Palmer et al.

(10) Patent No.: US 8,865,743 B2  
(45) Date of Patent: *Oct. 21, 2014

(54) SMALL VOLUME ORAL TRANSMUCOSAL DOSAGE FORMS CONTAINING SUFENTANIL FOR TREATMENT OF PAIN

(75) Inventors: Pamela Palmer, San Francisco, CA (US); Thomas Schreck, Portola Valley, CA (US); Stelios Tzannis, Newark, CA (US); Larry Hamel, Mountain View, CA (US); Andrew I. Poutiatine, San Anselmo, CA (US); Charles Rampersaud, San Francisco, CA (US); Bruce Edwards, Menlo Park, CA (US)

(73) Assignee: AcelRx Pharmaceuticals, Inc., Redwood City, CA (US)

( * ) Notice: Subject to any disclaimer, the term of this patent is extended or adjusted under 35 U.S.C. 154(b) by 1623 days.

This patent is subject to a terminal disclaimer.

(21) Appl. No.: 11/985,162

(22) Filed: Nov. 14, 2007

(65) Prior Publication Data

US 2008/0268023 A1  Oct. 30, 2008

Related U.S. Application Data

(63) Continuation-in-part of application No. 11/650,174, filed on Jan. 5, 2007, now Pat. No. 8,202,535.

(60) Provisional application No. 60/756,937, filed on Jan. 6, 2006.

(51) Int. Cl.  
*A01N 43/40* (2006.01)  
*A61K 31/445* (2006.01)  
*A61K 31/4535* (2006.01)  
*A61K 9/70* (2006.01)  
*A61K 9/20* (2006.01)  
*G06F 19/00* (2011.01)  
*A61K 9/00* (2006.01)

(52) U.S. Cl.  
CPC .............. *A61K 9/006* (2013.01); *A61K 31/4535* (2013.01); *A61K 9/7007* (2013.01); *A61K 9/2031* (2013.01); *G06F 19/3456* (2013.01); *A61K 9/2018* (2013.01); *A61K 9/2009* (2013.01)  
USPC ........................................................ 514/326

(58) Field of Classification Search  
USPC ........................................................ 514/326  
See application file for complete search history.

(56) References Cited

U.S. PATENT DOCUMENTS 2,621,655 A  12/1952  Olson et al.  
3,162,322 A  12/1964  Gilbertson (Continued)

FOREIGN PATENT DOCUMENTS

CA   2549642 A1   7/2005  
CN   2776369 Y    5/2006

(Continued)

OTHER PUBLICATIONS

Brendenberg, "New Concepts in Administration of Drugs in Tablet Form—Formulations and Evaluation of a Sublingual Tablet for Rapid Absorption, and Presentation of an Individualised Dose Administration System", Comprehensive Summaries of Uppsala Dissertations from the Faculty of Pharmacy 287, ACTA Universitatis UPSALIENSIS UPPSALA.

(Continued)

*Primary Examiner* — Benjamin Packard  
(74) *Attorney, Agent, or Firm* — Cooley LLP

(57) ABSTRACT

Compositions, systems and methods for administration of small volume sufentanil drug dosage forms to the sublingual mucosa of a subject for treatment of pain using a device are disclosed.

35 Claims, 18 Drawing Sheets

(56) References Cited

U.S. PATENT DOCUMENTS

| | | |
|---|---|---|
| 3,444,858 A | 5/1969 | Russell |
| 3,757,781 A | 9/1973 | Smart |
| 3,780,735 A | 12/1973 | Crouter et al. |
| 3,789,845 A | 2/1974 | Long |
| 4,020,558 A | 5/1977 | Cournut et al. |
| 4,060,083 A | 11/1977 | Hanson |
| 4,226,848 A | 10/1980 | Nagai et al. |
| 4,229,447 A | 10/1980 | Porter |
| 4,237,884 A | 12/1980 | Erickson |
| 4,474,308 A | 10/1984 | Bergeron |
| 4,582,835 A | 4/1986 | Lewis et al. |
| 4,671,953 A * | 6/1987 | Stanley et al. ............... 424/440 |
| 4,764,378 A | 8/1988 | Keith et al. |
| 4,785,969 A | 11/1988 | McLaughlin |
| 4,863,737 A | 9/1989 | Stanley |
| 4,873,076 A | 10/1989 | Fishman |
| 4,880,634 A | 11/1989 | Speiser et al. |
| 4,950,234 A | 8/1990 | Fujioka et al. |
| 5,080,903 A | 1/1992 | Ayache |
| 5,112,616 A | 5/1992 | McCarty |
| 5,122,127 A | 6/1992 | Stanley |
| 5,132,114 A | 7/1992 | Stanley |
| 5,178,878 A | 1/1993 | Wehling |
| 5,190,185 A | 3/1993 | Blechl |
| 5,223,264 A | 6/1993 | Wehling et al. |
| 5,236,714 A | 8/1993 | Lee |
| 5,263,596 A | 11/1993 | Williams |
| 5,288,497 A | 2/1994 | Stanley |
| 5,288,498 A | 2/1994 | Stanley |
| 5,292,307 A | 3/1994 | Dolzine et al. |
| 5,296,234 A | 3/1994 | Hadaway |
| 5,348,158 A | 9/1994 | Honan et al. |
| 5,352,680 A * | 10/1994 | Portoghese et al. .......... 514/279 |
| 5,366,113 A | 11/1994 | Kim et al. |
| 5,482,965 A | 1/1996 | Rajadhyaksha et al. |
| 5,489,025 A | 2/1996 | Romick |
| 5,489,689 A | 2/1996 | Mathew |
| 5,507,277 A | 4/1996 | Rubsamen |
| 5,507,807 A | 4/1996 | Shippert |
| 5,549,560 A | 8/1996 | Van de Wijdeven |
| 5,584,805 A | 12/1996 | Sutton |
| 5,657,748 A | 8/1997 | Braithwaite et al. |
| 5,660,273 A | 8/1997 | Discko, Jr. |
| 5,694,919 A | 12/1997 | Rubsamen |
| 5,710,551 A | 1/1998 | Ridgeway |
| 5,724,957 A | 3/1998 | Rubsamen |
| 5,735,263 A | 4/1998 | Rubsamen |
| 5,752,620 A | 5/1998 | Pearson |
| 5,785,989 A | 7/1998 | Stanley |
| 5,800,832 A | 9/1998 | Tapolsky et al. |
| 5,827,525 A | 10/1998 | Liao |
| 5,850,937 A | 12/1998 | Rauche et al. |
| 5,855,908 A | 1/1999 | Stanley et al. |
| 5,860,946 A | 1/1999 | Hofstatter |
| 5,945,651 A | 8/1999 | Chorosinski |
| 5,950,632 A | 9/1999 | Reber et al. |
| 5,954,641 A | 9/1999 | Kehr et al. |
| 5,968,547 A | 10/1999 | Reder et al. |
| 5,981,552 A | 11/1999 | Alam |
| 5,984,888 A | 11/1999 | Nielsen et al. |
| 5,995,938 A | 11/1999 | Whaley |
| 5,997,518 A | 12/1999 | Laibovitz et al. |
| 6,024,981 A | 2/2000 | Khankari |
| 6,039,251 A | 3/2000 | Holowko |
| 6,116,414 A | 9/2000 | Discko, Jr. |
| 6,131,765 A | 10/2000 | Barry et al. |
| 6,171,294 B1 | 1/2001 | Southam et al. |
| 6,190,326 B1 | 2/2001 | McKinnon |
| 6,200,604 B1 | 3/2001 | Pather |
| 6,210,699 B1 | 4/2001 | Acharya |
| 6,216,033 B1 | 4/2001 | Southam et al. |
| 6,230,927 B1 | 5/2001 | Schoonen et al. |
| 6,234,343 B1 | 5/2001 | Papp et al. |
| 6,248,789 B1 | 6/2001 | Weg |
| 6,264,981 B1 * | 7/2001 | Zhang et al. ................. 424/451 |
| 6,294,999 B1 | 9/2001 | Yarin et al. |
| 6,310,072 B1 | 10/2001 | Smith |
| 6,319,510 B1 | 11/2001 | Yates |
| 6,328,159 B1 | 12/2001 | Discko, Jr. |
| 6,350,470 B1 | 2/2002 | Pather |
| 6,358,944 B1 | 3/2002 | Lederman |
| 6,364,158 B1 | 4/2002 | Dimoulis |
| 6,391,335 B1 | 5/2002 | Pather |
| 6,417,184 B1 | 7/2002 | Ockert |
| 6,425,495 B1 | 7/2002 | Senda et al. |
| 6,425,892 B2 | 7/2002 | Southam et al. |
| 6,484,718 B1 | 11/2002 | Schaeffer et al. |
| 6,488,953 B2 | 12/2002 | Halliday et al. |
| 6,495,120 B2 | 12/2002 | McCoy |
| 6,500,456 B1 | 12/2002 | Capella |
| 6,509,036 B2 | 1/2003 | Pather |
| 6,541,021 B1 | 4/2003 | Johnson et al. |
| 6,564,967 B1 | 5/2003 | Stringfield et al. |
| 6,576,250 B1 | 6/2003 | Pather et al. |
| 6,599,529 B1 | 7/2003 | Skinhøj et al. |
| 6,605,060 B1 | 8/2003 | O'Neil |
| 6,607,750 B2 | 8/2003 | Upadhyay et al. |
| 6,641,838 B2 | 11/2003 | Pather |
| 6,642,258 B1 | 11/2003 | Bourrie |
| 6,645,528 B1 | 11/2003 | Straub |
| 6,651,651 B1 | 11/2003 | Bonney et al. |
| 6,660,295 B2 | 12/2003 | Watanabe et al. |
| 6,680,071 B1 | 1/2004 | Johnson et al. |
| 6,682,716 B2 | 1/2004 | Hodges et al. |
| 6,685,951 B2 | 2/2004 | Cutler |
| 6,689,373 B2 | 2/2004 | Johnson et al. |
| 6,726,053 B1 | 4/2004 | Harrold |
| 6,752,145 B1 | 6/2004 | Bonney et al. |
| 6,759,059 B1 | 7/2004 | Pettersson |
| 6,761,910 B1 | 7/2004 | Pettersson |
| 6,762,684 B1 | 7/2004 | Camhi |
| 6,764,696 B2 | 7/2004 | Pather |
| 6,776,978 B2 | 8/2004 | Rabinowitz et al. |
| 6,793,075 B1 | 9/2004 | Jeter et al. |
| 6,796,429 B2 | 9/2004 | Cameron |
| 6,824,512 B2 | 11/2004 | Warkentin et al. |
| 6,835,194 B2 | 12/2004 | Johnson et al. |
| 6,855,310 B2 | 2/2005 | Rabinowitz et al. |
| 6,881,208 B1 | 4/2005 | Phipps et al. |
| 6,914,668 B2 | 7/2005 | Brestel |
| 6,916,485 B2 | 7/2005 | Aiache et al. |
| 6,932,983 B1 | 8/2005 | Straub |
| 6,959,808 B2 | 11/2005 | Discko |
| 6,961,541 B2 | 11/2005 | Overy et al. |
| 6,963,289 B2 | 11/2005 | Aljadeff et al. |
| 6,969,508 B2 | 11/2005 | Dugger, III et al. |
| 6,974,590 B2 | 12/2005 | Pather |
| 6,999,028 B2 | 2/2006 | Egbert et al. |
| 7,004,111 B2 | 2/2006 | Olson et al. |
| 7,018,370 B2 | 3/2006 | Southam et al. |
| 7,018,619 B2 | 3/2006 | Rabinowitz et al. |
| 7,044,125 B2 | 5/2006 | Vedrine |
| 7,044,302 B2 | 5/2006 | Conley et al. |
| 7,070,762 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,072,738 B2 | 7/2006 | Bonney et al. |
| 7,074,935 B2 | 7/2006 | Mathew |
| 7,078,018 B2 | 7/2006 | Rabinowitz et al. |
| 7,078,019 B2 | 7/2006 | Rabinowitz et al. |
| 7,078,020 B2 | 7/2006 | Rabinowitz et al. |
| 7,090,830 B2 | 8/2006 | Hale |
| 7,090,866 B2 | 8/2006 | Johnson |
| 7,118,550 B2 | 10/2006 | Loomis |
| 7,119,690 B2 | 10/2006 | Lerch et al. |
| 7,168,626 B2 | 1/2007 | Lerch et al. |
| 7,169,378 B2 | 1/2007 | Rabinowitz et al. |
| 7,172,573 B1 | 2/2007 | Lamb |
| 7,198,172 B2 | 4/2007 | Harvey et al. |
| 7,208,604 B2 | 4/2007 | Mathew |
| 7,215,295 B2 | 5/2007 | Egbert et al. |
| 7,248,165 B2 | 7/2007 | Collins et al. |
| 7,264,139 B2 | 9/2007 | Brickwood et al. |
| 7,276,246 B2 | 10/2007 | Zhang et al. |

(56) References Cited

U.S. PATENT DOCUMENTS

| | | |
|---|---|---|
| 7,295,890 B2 | 11/2007 | Jean-Pierre et al. |
| 7,306,812 B2 | 12/2007 | Zhang et al. |
| 7,458,374 B2 | 12/2008 | Hale et al. |
| 7,468,179 B2 | 12/2008 | Rabinowitz et al. |
| 7,484,642 B2 | 2/2009 | Bonney et al. |
| 7,500,444 B2 | 3/2009 | Bonney et al. |
| 7,540,998 B2 | 6/2009 | Terwilliger et al. |
| 7,552,728 B2 | 6/2009 | Bonney et al. |
| 7,581,657 B2 | 9/2009 | Dickmann |
| 7,744,558 B2 | 6/2010 | Maag |
| 8,062,248 B2 | 11/2011 | Kindel |
| 8,142,733 B2 | 3/2012 | Creaven |
| 8,202,535 B2 | 6/2012 | Palmer et al. |
| 8,226,978 B2 | 7/2012 | Palmer et al. |
| 8,231,900 B2 | 7/2012 | Palmer et al. |
| 8,252,328 B2 | 8/2012 | Tzannis et al. |
| 8,252,329 B2 | 8/2012 | Tzannis et al. |
| 8,357,114 B2 | 1/2013 | Poutiatine et al. |
| 8,499,966 B2 | 8/2013 | Palmer et al. |
| 8,535,714 B2 | 9/2013 | Palmer et al. |
| 2001/0020147 A1 | 9/2001 | Staniforth et al. |
| 2002/0026330 A1 | 2/2002 | Klein et al. |
| 2002/0037491 A1 | 3/2002 | Halliday |
| 2002/0071857 A1 | 6/2002 | Kararli et al. |
| 2002/0110578 A1 | 8/2002 | Pather et al. |
| 2002/0142050 A1 | 10/2002 | Straub |
| 2002/0160043 A1 | 10/2002 | Coleman |
| 2003/0008005 A1 | 1/2003 | Cutler |
| 2003/0015196 A1 | 1/2003 | Hodges et al. |
| 2003/0015197 A1 | 1/2003 | Hale |
| 2003/0017175 A1 | 1/2003 | Cutler |
| 2003/0017994 A1 | 1/2003 | Cutler |
| 2003/0022910 A1 | 1/2003 | Cutler |
| 2003/0035776 A1 | 2/2003 | Hodges |
| 2003/0052135 A1 | 3/2003 | Conley et al. |
| 2003/0052787 A1 | 3/2003 | Zerhusen et al. |
| 2003/0077300 A1 | 4/2003 | Wermeling et al. |
| 2003/0088236 A1 | 5/2003 | Johnson et al. |
| 2003/0091629 A1 | 5/2003 | Pather et al. |
| 2003/0099158 A1* | 5/2003 | De la Huerga .............. 368/10 |
| 2003/0124185 A1 | 7/2003 | Oshlack et al. |
| 2003/0130314 A1 | 7/2003 | Druzgala |
| 2003/0132239 A1 | 7/2003 | Konig et al. |
| 2003/0171401 A1 | 9/2003 | Johnson et al. |
| 2003/0173408 A1 | 9/2003 | Mosher et al. |
| 2003/0181501 A1 | 9/2003 | Le et al. |
| 2003/0185872 A1 | 10/2003 | Kochinke et al. |
| 2003/0190290 A1 | 10/2003 | Ross |
| 2003/0232080 A1 | 12/2003 | Pather et al. |
| 2004/0017567 A1 | 1/2004 | Loicht et al. |
| 2004/0025871 A1 | 2/2004 | Davies |
| 2004/0034059 A1 | 2/2004 | Grarup et al. |
| 2004/0037882 A1 | 2/2004 | Johnson |
| 2004/0080515 A1 | 4/2004 | Hagiwara et al. |
| 2004/0092531 A1 | 5/2004 | Chizh |
| 2004/0094564 A1 | 5/2004 | Papp et al. |
| 2004/0096402 A1 | 5/2004 | Hodges et al. |
| 2004/0120896 A1 | 6/2004 | Dugger et al. |
| 2004/0133305 A1 | 7/2004 | Jean-Pierre |
| 2004/0157884 A1 | 8/2004 | Johnson et al. |
| 2004/0158349 A1 | 8/2004 | Bonney et al. |
| 2004/0170567 A1 | 9/2004 | Sackler et al. |
| 2004/0180080 A1 | 9/2004 | Furusawa et al. |
| 2004/0185003 A1 | 9/2004 | Rabinowitz et al. |
| 2004/0191178 A1 | 9/2004 | Cutler |
| 2004/0202617 A1 | 10/2004 | Rabinowitz et al. |
| 2004/0213855 A1 | 10/2004 | Pettersson |
| 2004/0248964 A1 | 12/2004 | Crooks |
| 2004/0253307 A1 | 12/2004 | Hague et al. |
| 2005/0038062 A1 | 2/2005 | Burns |
| 2005/0049464 A1 | 3/2005 | Lassers |
| 2005/0054942 A1 | 3/2005 | Melker |
| 2005/0064030 A1 | 3/2005 | Pather et al. |
| 2005/0065175 A1 | 3/2005 | Gonzales et al. |
| 2005/0075273 A1 | 4/2005 | Rabinowitz et al. |
| 2005/0089479 A1 | 4/2005 | Rabinowitz et al. |
| 2005/0101936 A1 | 5/2005 | Gonzales et al. |
| 2005/0122219 A1 | 6/2005 | Petersen et al. |
| 2005/0129737 A1 | 6/2005 | Johnson |
| 2005/0131337 A1 | 6/2005 | Phipps et al. |
| 2005/0131386 A1 | 6/2005 | Freeman et al. |
| 2005/0142197 A1 | 6/2005 | Moe |
| 2005/0142198 A1 | 6/2005 | Moe |
| 2005/0150488 A1 | 7/2005 | Dave et al. |
| 2005/0150489 A1 | 7/2005 | Dunfield et al. |
| 2005/0163838 A1 | 7/2005 | Moe |
| 2005/0169989 A1 | 8/2005 | Moe et al. |
| 2005/0171464 A1 | 8/2005 | Phipps et al. |
| 2005/0176790 A1* | 8/2005 | Bartholomaus et al. ...... 514/373 |
| 2005/0177275 A1 | 8/2005 | Harvey et al. |
| 2005/0192218 A1 | 9/2005 | Ellis et al. |
| 2005/0258066 A1 | 11/2005 | Conley et al. |
| 2006/0026035 A1 | 2/2006 | Younkes |
| 2006/0031099 A1 | 2/2006 | Vitello et al. |
| 2006/0039959 A1 | 2/2006 | Wessling |
| 2006/0045865 A1 | 3/2006 | Jacob et al. |
| 2006/0062812 A1 | 3/2006 | Ross |
| 2006/0067978 A1 | 3/2006 | Heiler et al. |
| 2006/0069344 A1 | 3/2006 | Southam et al. |
| 2006/0089858 A1 | 4/2006 | Ling |
| 2006/0134200 A1 | 6/2006 | Vandoni et al. |
| 2006/0210632 A1 | 9/2006 | Oury et al. |
| 2006/0216352 A1 | 9/2006 | Nystrom |
| 2006/0229570 A1 | 10/2006 | Lovell |
| 2006/0233718 A1 | 10/2006 | Rabinowitz et al. |
| 2006/0251587 A1 | 11/2006 | Rabinowitz et al. |
| 2006/0292219 A1 | 12/2006 | Pather |
| 2007/0020186 A1 | 1/2007 | Stroppolo |
| 2007/0031502 A1 | 2/2007 | Pettersson |
| 2007/0036853 A1 | 2/2007 | Agarwal |
| 2007/0071806 A1 | 3/2007 | McCarty et al. |
| 2007/0074722 A1 | 4/2007 | Giroux |
| 2007/0104763 A1 | 5/2007 | Jobdevairakkam et al. |
| 2007/0178052 A1 | 8/2007 | Rabinowitz et al. |
| 2007/0184096 A1 | 8/2007 | Ameri et al. |
| 2007/0185084 A1 | 8/2007 | McKinney |
| 2007/0186923 A1 | 8/2007 | Poutiatine et al. |
| 2007/0190130 A1 | 8/2007 | Mark |
| 2007/0207207 A1 | 9/2007 | Tzannis et al. |
| 2007/0260491 A1 | 11/2007 | Palmer et al. |
| 2007/0286900 A1 | 12/2007 | Herry |
| 2007/0299687 A1 | 12/2007 | Palmer et al. |
| 2008/0147044 A1 | 6/2008 | Palmer et al. |
| 2008/0164275 A1 | 7/2008 | Poutiatine et al. |
| 2008/0166404 A1 | 7/2008 | Tzannis et al. |
| 2008/0203107 A1 | 8/2008 | Conley et al. |
| 2008/0268023 A1 | 10/2008 | Palmer et al. |
| 2009/0010992 A1 | 1/2009 | Palmer et al. |
| 2009/0048237 A1 | 2/2009 | Palmer et al. |
| 2009/0131479 A1 | 5/2009 | Palmer et al. |
| 2009/0258948 A1 | 10/2009 | Bartholomaus et al. |
| 2010/0105735 A1 | 4/2010 | Palmer et al. |
| 2010/0130551 A1 | 5/2010 | Pushpala et al. |
| 2010/0137836 A1 | 6/2010 | Palmer et al. |
| 2010/0253476 A1 | 10/2010 | Poutiatine et al. |
| 2010/0256190 A1 | 10/2010 | Palmer et al. |
| 2011/0091544 A1 | 4/2011 | Palmer |
| 2011/0288128 A1 | 11/2011 | Palmer et al. |
| 2012/0035216 A1 | 2/2012 | Palmer et al. |
| 2012/0232473 A1 | 9/2012 | Poutiatine et al. |
| 2013/0090594 A1 | 4/2013 | Palmer et al. |
| 2013/0131586 A1 | 5/2013 | Poutiatine et al. |
| 2013/0156842 A1 | 6/2013 | Tzannis et al. |
| 2013/0158074 A1 | 6/2013 | Palmer et al. |
| 2013/0165481 A1 | 6/2013 | Palmer et al. |

FOREIGN PATENT DOCUMENTS

| | | |
|---|---|---|
| EP | 1243524 A2 | 9/2002 |
| EP | 1261316 B1 | 4/2008 |
| EP | 2114383 B1 | 7/2010 |
| GB | 2309966 | 8/1997 |
| JP | 2000-142841 A | 5/2000 |
| JP | 2003-525081 A | 8/2003 |

(56) References Cited

FOREIGN PATENT DOCUMENTS

| | | |
|---|---|---|
| JP | 2004-511310 A | 4/2004 |
| JP | 2004-531806 A | 10/2004 |
| JP | 2005-199066 A | 7/2005 |
| JP | 2007-517636 A | 7/2007 |
| WO | WO 89/10127 A1 | 11/1989 |
| WO | 00/16750 | 3/2000 |
| WO | WO 00/16750 | 3/2000 |
| WO | 00/57858 | 10/2000 |
| WO | WO 00/57858 | 10/2000 |
| WO | 01/30288 | 5/2001 |
| WO | WO 01/30288 | 5/2001 |
| WO | WO 01/64182 A2 | 9/2001 |
| WO | 01/97780 | 12/2001 |
| WO | WO 02/32487 A1 | 4/2002 |
| WO | WO 02/067903 A2 | 9/2002 |
| WO | WO 02/074372 A2 | 9/2002 |
| WO | WO 02067916 A2 * | 9/2002 |
| WO | WO 02/078594 A2 | 10/2002 |
| WO | WO 03/047519 A2 | 6/2003 |
| WO | WO 03/070304 A1 | 8/2003 |
| WO | WO 03/092575 A2 | 11/2003 |
| WO | 2004/069198 | 8/2004 |
| WO | WO 2004/067004 A1 | 8/2004 |
| WO | WO 2004/069198 | 8/2004 |
| WO | 2004/080515 | 9/2004 |
| WO | WO 2005/032556 A1 | 4/2005 |
| WO | WO 2005/065319 A2 | 7/2005 |
| WO | WO 2005/097075 A2 | 10/2005 |
| WO | WO 2006/026840 A2 | 3/2006 |
| WO | WO2006097361 | 9/2006 |
| WO | WO 2006/103418 A1 | 10/2006 |
| WO | WO 2007/081949 A2 | 7/2007 |
| WO | WO 2008/085764 A1 | 7/2008 |
| WO | WO 2008/085765 A2 | 7/2008 |
| WO | WO 2009/021106 A1 | 2/2009 |

OTHER PUBLICATIONS

Chauvin, M., "Sufentanil Pharmacokinetics in Patients With Cirrhosis", Anesthes Analg, 1989, 68(1):1-4.
Coluzzi P.H., et al., Breakthrough Cancer Pain: A Randomized Trial Comparing Oral Transmucosal Fentanyl Citrate (OTFC) and Morphine Sulfate Immediate Release (MSIR), Pain, 2001, 91(1-2):123-130.
Farnsworth, S.T., et al., "Ocular Transmucosal Absorption and Toxicity of Sufentanil in Dogs", Anesth Analg, 1998, 86:138-140.
Gardner-Nix J., "Oral Transmucosal Fentanyl and Sufentanil for Incident Pain", J Pain Symptom Management, Aug. 2001, 22(2):627-630.
Geldner, G., et al., "Comparison Between Three Transmucosal Routes of Administration of Midazolam in Children", Paediatr Anaesth, 1997, 7(2):103-109.
Gerak, L.R., "Studies on Benzodiazepines and Opioids Administered Alone and in Combination in Rhesus Monkeys: Ventilation and Drug Discrimination", Psychopharmacology, 1998, 137:164-174.
Gordon, D.B., Oral Transmucosal Fentanyl Citrate for Cancer Breakthrough Pain: A Review, Oncol Nurs Forum, Nov. 3, 2006, 33(2)257-264.
Gram-Hansen P., "Plasma Concentrations Following Oral and Sublingual Administration of Lorazepam", Int J. Clin Pharmacol Ther Toxical, 1988, 26(6):323-324.
Haynes, G., "Plasma Sufentantil Concentration After Intranasal Administration to Paediatric Outpatients", Can J. Anaesth, 1993, 40(3):286.
Helmers, et al., 1989, Can J. Anaesth, 1989, 6:494-497.
Jackson K., et al., "Pilot Dose Finding Study of Intranasal Sufentanil for Breakthrough and Incident Cancer-Associated Pain", J Pain Symptom Manage, 2002, 23(6):450-452.
Jackson, "Pharmacokinetics and Clinical Effects of Multidose Sublingual Triazolam in Healthy Volunteers" J Clin Psychopharmacol, Feb. 2006, 26(1):4-8.

James, et al., "The Use of a Short-Acting Benzodiazepine to Reduce the Risk of Syncopal Episodes During Upright Sterotactic Breast Biopsy", Clin Radiol, Mar. 2005, 60(3):394-396.
Jeannet, et al., "Home and Hospital Treatment of Acute Seizures in Children with Nasal Midazolam", Eur J. Paediatr Neurol, 1999, 3(2):73-77.
Kaplan, G.B., "Single Dose Pharmacokinetics and Pharmacodynamics of Alprazolam in Elderly and Young Subjects", PubMed, 1998, 38(1):14-21.
Karl, et al., "Comparison of the Safety and Efficacy of Intranasal Midazolam of Sufentanil for Preinduction of Anesthesia in Pediatric Patients", Anesthesiology, 1992, 76:209-215.
Karl, H.W., Transmucosal Administration of Midazolam for Premedication of Pediatric Patients, Anesthesiology, 1993, 78(5):885-891.
Khalil, et al., "Sublingual Midazolam Premedication in Children: A Dose Response Study", Paediatr Anaesth, 1998, 8(6):461-465.
Kogan, et al., "Premedication with Midazolam in Young Children: A Comparison of four Routes of Administration", Paediatr Anaesth Oct. 2002, 12(8):685-689.
Kontinen, et al., "Premedication With Sublingual Triazolam Compared With Oral Diazepam", Canadian Journal of Anesthesia, 1993, 40:829-834.
Kroboth, P.D., "Triazolam Pharmacokinetics After Intravenous, Oral and Sublingual Administration", J Clin Psychophamacol, 1995, 15(4):259-262.
Kunz, K.M., "Severe Episodic Pain: Management With Sublingual Sufentanil", Journal of Pain and Symptom Management, 1993, 8:189-190.
Lennernäs B., "Pharmacokinetics and Tolerability of Different Doses of Fentanyl Following Sublingual Administration of a Rapidly Dissolving Tablet to Cancer Patients: A New Approach to Treatment of Incident Pain", Br J Clin Pharmacol, Feb. 2005, 59(2):249-253.
Lichtor, J.L., "The Relative Potency of Oral Transmucosal Fentanyl Citrate (OTFC) Compared With Intravenous Morphine in the Treatment of Moderate to Severe Postoperative Pain" Anesth Anal, 1999, 89(3):732-738.
Lipworth, et al., Pharmacokinetics, Effacacy and Adverse Efects of Sublingual Salbutamol in Patients with Asthma, European Journal of Clinical Pharmacology, Nov. 1989, 37(6).
Mathieu, N., et al., "Intranasal Sufentanil is Effective for Postoperative analgesia in Adults", Can J Anesth, 2006, 53(1):60-66.
McCann and Kain, "The Management of Preoperative Anxiety in Children: an Update", Anesthesia & Analgesia, 2001, 93:98-105.
Monk, J.P., "Sufentanil: A Review of Its Pharmacological Properties and Therapeutic Use", Drugs, 1988, 36:286-313.
Naguib, et al. "The Comparative Dose-Response Effects fo Melatonin and Midazolam for Premedication of Adult Patients: A Double-Blinded, Placebo-Controlled Study", Anesth Analg, Aug. 2000, 91(2):473-479.
Odou, C., et al., "Development of Midazolam Sublingual Tablets: In Vitro Study", Eur J Drug Metab Pharmacokinet, Apr.-Jun. 1998, 23(2):87-91.
Okayama, et al, "Bronchodilator Effect of Sublingual Isosorbide Dinitrate in Asthma", Eur J Clin Pharmacol, 1984, 26(2):151-155.
Roy, S.D., "Transdermal Delivery of Narcotic Analgesics: pH, Anatomical, and Subject Influences on Cutaneous Permeability of Fentanyl and Sufentanil", Pharm Res, 1990, 7:842-847.
Scavone, J.M., "The Pharmacokinectics and Pharmacodynamics of Sublingual and Oral Alprazolam in the Post-Pradial State", Eur J Clin Pharmacol, 1992, 42(4):439-443.
Scavone, J.M., et al, "Enhanced Bioavailibility of Triazolam Following Sublingual Versus Oral Administration", J Clin Pharmacol, Mar. 1986, 26(3):208-210.
Schreiber, K.M., "The Association of Preprocedural anxiety and the Success of Procedural Sedation inChildren", Am J Emerg Med, Jul. 2006, 24(4):397-401.
Schwagmeier, R., "Midazolam Pharmacokinetics Following Intravenous and Buccal Administration", Br J Clin Pharmacol, 1998, 46:203-206.
Sinatra, R.S., "Patient-Controlled Analgesia with Sufentanil: A Comparison of Two Different Methods of Administration", Journal of Clinical Anesthesia, 1996, 8:123-129.

(56) References Cited

OTHER PUBLICATIONS

Tweedy, C.M., "Pharmacokinetics and Clinical Effects of Sublingual Triazolam in Pediatric Dental Patients" J Clin Psychopharmacol, 2001, 21(3):268-272.
Vercauteren M., "Intranasal Sufentanil for Pre-Operative Sedation", Anaesthesia, 1988, 43(4):270-273.
Viitanen, et al, "Medazolam Premedication Delays Recovery from Propofol-Induced Sevoflurane Anesthesia in Children 1-3 yr", Canadian Journal of Anaesthesia, 1999, 46:766-71.
Weniberg, D.S., Sublingual Absorption of Selected Opioid Analgesics, Clin Parmacol Ther, Sep. 1988, 44(3):335-342.
Wheeler, M., "Uptake Pharmacokinetics of the Fentanyl Oralet in Children Scheduled for Central Venous Access Removal: Implications for the timing of Initiating Painful Procedures", Paediatric Anesthesia, 2002, 12:594-599.
Willens, J.S., "Pharmacodynamics, Pharmacokinetics, and Clinical Uses of Fentanyl, Sufentanil, and Alfentanil", Heart and Lung, 1993, 22:239-251.
Yager J.Y., "Sublingual Lorazepam in Childhood Serial Seizures", Am J Dis Child, 1988, 142:931-932.
Zedie, N., "Comparison of Intranasal Midazolam and Sufentanil Premedication in Pediatric Outpatients", Clin Parmacol and Therapeutics, 1996, 59:341-348.
Zhang, H., "Oral Mucosal Drug Delivery: Clinical Pharmacokinetics and Therapeutic Applications", Clinical Pharmacokinetics, 2002, 41(9):661-680(20).
ACTIQ fact sheet printed Mar. 2004.
Dale, et al., 2002, Acta Anaesth Scand, 46:759-770.
Darwish et al., 2007, J Clin Pharm 47: 56-63.
Darwish, et al., 2006, Clinical Therapies, 28(5):707-14.
Demeules, et al., Eur J Anaesthesiol Suppl. 2003; 28:7-11.
Egan, et al., 2000, Anesthesiology, 96:665-73.
Gardner-Nix J, J Pain Symptom Manage; 2001; 22:627-630.
Good, et al., 2009, Palliative Medicine, 23:54-58.
Henderson JM, et al.; Anesthesiology; 1988; 68:671-675.
Joshi, et al., 1993, Indian Pediatr, 30(1):84-5.
Karl, et al., 1997, Journal Clinical Psychopharmacology, 17(3):169-172.
Lim, et al., 1997, Can J Anaesth, 44(7): 723-6.
Mendelson J, et al.; J Clin Pharmacol; 1997; 37:31-7.
Motwani JG, Lipworth BJ; Clin Pharmacokinet; 1991; 21(2):83-94.
Mystakidou K, et al.; Drug Deliv. 2006; 13(4):269-76.
Nath RP, et al.; J Clin Pharmacol; 1999; 39:619-23.
Odou, et al., 1999, Eur J Drug Metab Pharmacokinet, 24(1):1-7.
Pavlin, et al., Anesthesiology. Jan. 1996; 84(1):23-37.
Portenoy RK, et al.; Pain; 1999; 79:303-12.
Raza, et al., Can J Anaesth. Nov. 1989; 36(6):617-23.
Reisfield G, Wilson G; Journal of Palliative Medicine; 2007; 10(2):465-475.
Reynolds, et al., 2004, Pain, 110:182-188.
Roy, SD and Flynn, GL; Pharm Research; 1989; 6(2): 147-151.
Scavone, et al., 1987, J Clin Psychpharmacol, 7(5):332-4.
Scholz J, et al.; Clin Pharmacokin ; 1996; 31:275-292.
Stopperich, et al., 1993, Anesth Prog, 40(4):117-21.
Streisand JB, et al.; Anesthesiology; 1991; 75:223-9.
Streisand JB, et al.; Anesthesiology; 1998; 88:305-9.
Sufenta Package Insert, 2006.
Zedie, et al., 1996, Clin Pharmacol Ther, 59:341-8.
Office Action for U.S. Appl. No. 11/429,904, mailed Sep. 17, 2008.
Office Action for U.S. Appl. No. 11/980,216, mailed Dec. 24, 2008.
Office Action for U.S. Appl. No. 11/11/650,230, mailed Sep. 25, 2008.
Office Action for U.S. Appl. No. 11/11/650,230, Mar. 10, 2009.
Office Action for U.S. Appl. No. 11/429,904, mailed Mar. 5, 2009.
Office Action for U.S. Appl. No. 11/650,227, mailed Dec. 9, 2008.
Office Action for U.S. Appl. No. 11/473,551, mailed Mar. 16, 2009.
Office Action for U.S. Appl. No. 11/473,551, mailed Sep. 26, 2008.
Office Action for U.S. Appl. No. 11/650,227, mailed Jul. 6, 2009.
Office Action for U.S. Appl. No. 11/980,216, mailed Jul. 20, 2009.
ISR WO2008/085764, Date mailed Jun. 23, 2008.
ISR WO2008/072445 AceIRx7PCT, mailed Oct. 20, 2008.
ISR WO2007/133478 (AceIRx2 PCT), mailed Aug. 5, 2008.
ISR WO2008/002358 (AceIRx3 PCT), mailed Aug. 21, 2008.
ISR WO2007/081949 (AceIRx6 PCT), mailed Sep. 11, 2007.
ISR WO2008/085765 (AceIRx6CIP2 PCT), mailed Oct. 15, 2008.
International Search Report and Written Opinion dated Dec. 17, 2007 issued in PCT/2007/00527 (WO/2007/081947).
International Search Report and Written Opinion dated Feb. 4, 2008 issued in PCT/2007/00528 (WO/2007/081948).
Berthold et.al.; "Comparison of sublingually and orally administered triazolam for premedication before oral surgery"; *Oral Surg Oral Med Oral Pathol Oral Radiol Endod*; 1997; 84(2):119-24.
Bredenberg et al; "In vitro and in vivo evaluation of a new sublingual tablet system for rapid or mucosal absorption using fentanyl citrate as the active substance"; *European Journal of Pharmaceutical Sciences*; 2003; 327-334.
Darwish et al.; "Bioequivalence following buccal and sublingual placement of fentanyl buccal tablet 400mcg in healthy subjects"; *Clin. Drug Invest*. 2008: 28(1): 1-7.
Darwish et al.; "Effect of buccal dwell time on the pharmacokinetic profile of fentanyl buccal tablet"; *Expert Opin. Pharmacother* Sep. 2007;8(13):2011-6. Review.
Darwish et al.; "Comparison of equivalent doses of fentanyl buccal tablets and arteriovenous differences in fentanyl pharmacokinetics"; *Clinical Pharmacokinetics*; 2006; 45(8): 843-50.
Darwish et al.; "Relative bioavailability of the fentanyl effervescent buccal tablet (FEBT) 1,080 pg versus oral transmucosal fentanyl citrate 1,600 pg and dose proportionality of FEBT 270 to 1,300 microg: a single dose, randomized, open-label, three period study in healthy adult volunteers"; *Clinical Therapies*; 2006; 28(5):715-24.
Darwish et al.; "Pharmacokinetics and dose proportionality of fentanyl effervescent buccal tablets in healthy volunteers"; *Clinical Pharmacokinetics*; 2005; 44(12): 1279-86.
KGH Drug Information Service; "Sublingual Sufentanil for Incident Pain"; *KGH Drug Information Bulletin*, vol. 37(4) 2, 2004.
Yeomans et al.; "Sublingual Sufentanil"; *Vancouver Hospital and Health Science Center Drug and Therapeutics Newsletter*, vol. 8(1) 2, 2001.
"FDA Guidance for Industry: Container Closure Systems for Packaging Human Drugs and Biologics," May 1999, pp. 1-E2.
"Triazolam" Drug Facts and Comparisons (Fiftieth Edition). 1996. Wolters Kluwer. p. 1619.
"Sufentanil Citrate," AHFS Drug Information, 28:08.08, 2157-2160, 2007.
Abrams, R. et al., "Safety and Effectiveness of Intranasal Administration of Sedative Medications (Ketamine, Midazolam, or Sufentanil) for Urgent Brief Pediatric Dental Procedures," Anesth Prog., 40:63-66 (1993).
AcelRx Pharmaceuticals, Inc., "AcelRx Pharmaceuticals Reports Positive Results from a Clinical Trial of Sublingual Sufentanil/Triazolam NanoTab™ Combination (ARX-03) in Treating Procedural Pain and Anxiety," 2 pages, Press Release (Jan. 12, 2009).
Actiq package insert (Cephalon) (2004).
Ahmad, S. et al., "Fentanyl HCl iontophoretic transdermal system versus intravenous morphine pump after gynecologic surgery," Arch. Gynecol. Obstet. 276:251-258 (2007).
Albert, J. M. et al., "Patient-Controlled Analgesia vs. Conventional Intramuscular Analgesia Following Colon Surgery," Diseases of the Colon & Rectum, 31(2):83-86 (1988).
Anlar, S. et al., "Formulation and In Vitro-In Vivo Evaluation of Buccoadhesive Morphine Sulfate Tablets," Pharm. Res., 11(2):231-236 (1994).
Bayrak, F. et al., "A Comparison of Oral Midazolam, Oral Tramadol, and Intranasal Sufentanil Premedication in Pediatric Patients," J. Opiod. Management, 3(2):74-78 (2007).
Bovill, G. J. et al., "The Pharmacokinetics of Sufentanil in Surgical Patients," Anesthesiology, 61:502-506 (1984).
Brown et al., "Procedural Sedation in the Acute Care Setting," Amer. Fam. Pharm. 71(1):85-90 (2005).
Brusset, A. et al., "Comparative Pharmacokinetic Study of Fentanyl and Sufentanil After Single High-Bolus Doses," Clin Drug Invest, 18(5):377-389 (1999).

(56) References Cited

OTHER PUBLICATIONS

Chen et al., "Studies on Formulations of Fenntanyl-Containing Oral Adhesive Tablets," Chin. J. Pharm. 28(3):129-131 (1997).
Christie, J. M. et al., "Dose-titration, multi-center study of oral transmucosal fentanyl citrate for the treatment of breakthrough pain in cancer patients using transdermal fentanyl for persistent pain," J Clin Oncol., 16(10):3238-3245 (1998).
Coda, B.A. et al., "Comparative efficacy of patient-controlled administration of morphine, hydromorphone, or sufentanil for the treatment of oral mucositis pain following bone marrow transplantation," Pain, 72:333-346 (1997).
Collins, L. M. C. et al., "The Surface Area of the Adult Human Mouth and Thickness of the Salivary Film Covering the Teeth and Oral Mucosa," J. Dent. Res. 66(8):1300-1302 (1987).
Coluzzi, Sublingual Morphine: Efficacy Reviewed, J. Pain Symp. Manage. 16(3):184-192 (1998).
Darwish, M. et al., "Absolute and Relative Bioavailability of Fentanyl Buccal Tablet and Oral Transmucosal Fentanyl Citrate," Journal of Clinical Pharmacology, 47:343-350 (2007).
De Castro, J. et al., "Practical Applications and Limitations of Analgesic Anesthesia," Acta Anesthesiologica Belgica, 3:107-128 (1976).
DeVries, M. et al., "Developments in Buccal Drug Delivery," Critical Reviews in Therapeutic Drug Carrier Systems, 8(3):271-303 (1991).
Durfee, S. et al., "Fentanyl Effervescent Buccal Tablets: Enhanced Buccal Absorption," American Journal of Drug Delivery, 4(1):1-5 (2006).
Ellmauer, S., "Sufentanil: An Alternative to Fentanyl/Alfentanil?" Anaesth. 43(3):143-158 (1994).
Enting, H. R. et al., "The 'Pain Pen' for Breakthrough Cancer Pain: A Promising Treatment," Journal of Pain and Symptom Management 29(2):213-217 (2005).
Fisher, D.M. et al., "Pharmacokinetics of an Implanted Osmotic Pump Delivering Sufentanil for the Treatment of Chronic Pain," Anesthesiology, 99(4):929-937 (Oct. 2003).
Friedman et al., "Population study of triazolam pharmacokinetics," Br. J. Clin. Pharmacol., 22:639-642, 1986.
Goodwin et al., "Clinical Policy: Procedural Sedation and Analgesia in the Emergency Department," Annals Emerg. Med. 45(2) 177-196, 2005.
Grass, J., "Patient-Controlled Analgesia," Anesth. Analg., 101:S44-S61 (2005).
Guay, J. et al., "Pharmacokinetics of Sufentanil in Normal Children," Canadian Journal of Anaesthesia, 39(1):14-20 (1992).
Halliburton, J. R., "The Pharmacokinetics of Fentanyl, Sufentanil and Alfentanil: A Comparative Review," Journal of the American Association of Nurse Anesthetists, 56(3):229-233 (1988).
Hazardous Substances Data Bank (HSDB) [online] [Retrieved from the Internet]. URL: http://toxnet.nlm.nih.gov. Apr. 9, 2007, Name: Sufentanil; RN: 56030-54-7.
Helmers, J. H. et al., "Sufentanil Pharmacokinetics in Young Adult and Elderly Surgical Patients," European Journal of Anaesthesiology, 11(3):181-185 (1994).
Heshmati et al., "Intranasal Sufentanil for Postoperative Pain control in Lower Abdominal Pediatric Surgery," Iran. J. Pharmacol. Therap., 5:131-133 (2006).
Hicks et al., "The measurement of preoperative anxiety," J. Royal Soc. Med., 81: 517-519, 1988.
Hicks, R. et al., "USP Medication Safety Forum: Medication Errors Involving Patient-Controlled Analgesia," Joint Commission on Quality and Patient Safety, 34(12):734-742 (2008).
Ikinci, G. et al., "Development of buccal bioadhesive nicotine tablet formulation for smoking cessation," Int. J. Pharm, 277(1-2):173-178 (2004).
International Preliminary Report on Patentability for International Application No. PCT/US2007/000527, dated Feb. 24, 2009.
International Preliminary Report on Patentability for International Application No. PCT/US2007/000528, dated Jul. 8, 2008.
International Preliminary Report on Patentability for International Application No. PCT/US2007/000529, dated Jul. 8, 2008.
International Preliminary Report on Patentability for International Application No. PCT/US2007/089016, dated Jul. 7, 2009.
International Preliminary Report on Patentability for International Application No. PCT/US2007/089017, dated Jul. 7, 2009.
International Preliminary Report on Patentability for International Application No. PCT/US2007/089018, dated Jul. 7, 2009.
International Preliminary Report on Patentability for International Application No. PCT/US2010/052655, dated Apr. 17, 2012.
International Preliminary Report on Patentability for International Application No. PCT/US2009/064232, dated May 24, 2011.
International Preliminary Report on Patentability for International Application No. PCT/US2008/072445, dated Feb. 9, 2010.
International Search Report for International Application No. PCT/US2010/052655, mailed Apr. 4, 2011.
International Search Report for International Application No. PCT/US2007/089016, mailed Jun. 17, 2008.
International Search Report for International Application No. PCT/US2011/037401, mailed Aug. 19, 2011.
International Search Report for International Application No. PCT/US2010/027437, mailed Jun. 21, 2010.
International Search Report for International Application No. PCT/US2009/064232, mailed Mar. 17, 2010.
Jia et al., p. 10, in Novel controlled-release dosage forms for drugs, Chemical Industry Press (CIP), China (2005).
Kraus et al., "Procedural sedation and analgesia in children," Lancet 367:766-780 (2006).
Kress et al. "Sedation and Analgesia in the Intensive Care Unit". Am J Respir Crit Care Med. 166; 2002:1024-1028.
Kress et al., "Efficacy and Tolerability of Intranasal Fentanyl Spray 50 to 200 μg for Breakthrough Pain in Patients With Cancer: A Phase III, Multinantional, Randomized, Double-Blind, Placebo-Controlled, Crossover Trial With a 10-Month, Open-Label Extension Treatment Period," Clinical Therapeutics, 31(6): 1171-1191 (2009).
Lehman, K. A. et al., "Pharmacokinetics of sufentanil in general surgical patients under different conditions of anesthesia," Acta Anaesthesiol Scand., 37:176-180 (1993).
Lehman, K. A. et al., "Postoperative patient-controlled analgesia with sufentanil: analgesic efficacy and minimum effective concentrations," Acta Anaesthesiol Scand., 35:221-226 (1991).
Loeffler, "Oral Benzodiazepines and Conscious Sedation: A Review," J. Oral Maxillofacial. Surg., 50(9) 989-997, 1992.
Mather, L. E., "Clinical Pharmacokinetics of Fentanyl and its Newer Derivatives," Clinical Pharmacokinetics, 8:422-446 (1983).
Molander, L. et al., "Pharmacokinetic investigation of a nicotine sublilngual tablet," Eur. J. Clin. Pharmacol., 56(11):813-819 (2001).
Onsolis Package Insert Jul. 2009.
Paix, A. et al., "Subcutaneous fentanyl and sufentanil infusion substitution for morphine intolerance in cancer pain management," Pain, 63:263-269 (1995).
Portenoy, R. K. et al., "A Randomized, Placebo-controlled Study of Fentanyl Buccal Tablet for Breakthrough Pain in Opioid-treated Patients with Cancer," Clin. J. Pain, 22(9):805-811 (2006).
Puig, M. M. et al., "Sufentanil Pharmacokinetics in Neurosurgical Patients," Intl. J. Clin. Pharmaco. Ther. Toxicol., 27(5):229-234 (1989).
Rosow, C. E., "Sufentanil Citrate: A New Opioid Analgesic for Use in Anesthesia," Pharmacotherapy, 4:11-19 (1984).
Savoia, G. et al., "Sufentanil: an overview of its use for acute pain management," Minerva Anesth, 67(9 Suppl 1):206-216 (2001).
Siepmann, J. et al., "Calculation of the Required Size and Shape of Hydroxypropyl Methylcellulose Matrices to Achieve Desired Drug Release Profiles," International Journal of Pharmaceutics, 201(1):151-164 (2000).
Smith, R. B. et al., "Temporal variation in traizolam pharmacokinetics and pharmacodynamics after oral administration," J. Clin. Pharmacol., 26(2):120-4 (1986).
Striebel, H. W. et al., "Patient-controlled intranasal analgesia (PCINA) for the management of postoperative pain: a pilot study," J Clin Anesth, 8:4-8 (1996).
Striebel, H. W. et al., "Patient-controlled intranasal analgesia: a method for noninvasive postoperative pain management," Anesth Analg, 83:548-551 (1996).

(56) References Cited

OTHER PUBLICATIONS

Supplementary European Search Report for European Application No. EP 08797363.2 dated Sep. 15, 2010.
Supplementary European Search Report for European Application No. EP 07716450.7 dated Apr. 6, 2011.
Van De Walle, J. et al., "Double blind comparison of fentanyl and sulfentanil in anesthesia," Acta Anaesth Belg, 27(3):129-138 (2009).
Van Vlymen et al., "Benzodiazepine Premedication," Anesthesiology 90:740-747, 1999.
Viscusi, E. R. et al., "An iontophoretic fentanyl patient-activated analgesic delivery system for postoperative pain: a double-blind, placebo-controlled trial," Anesth Analg., 102(1):188-194 (2006).
Viscusi, E. R. et al., "Patient-Controlled Transdermal Fentanyl Hydrochloride vs Intravenous Morphine Pump for Postoperative Pain: A randomized controlled trial," JAMA, 291(11):1333-1341 (2004).
Walder et al., Analgesia and Sedation in Critically Ill Patients, Swiss Med. Wkly., 134(23-24):333-346 (2004).
Written Opinion for International Application No. PCT/US2007/000529, mailed Sep. 11, 2007.
Written Opinion for International Application No. PCT/US2007/089018, mailed Oct. 15, 2008.
Written Opinion for International Application No. PCT/US2007/089016, mailed Jun. 17, 2008.
Written Opinion for International Application No. PCT/US2007/089017, mailed Jun. 23, 2008.
Written Opinion for International Application No. PCT/US2008/072445, mailed Oct. 20, 2008.
Written Opinion for International Application No. PCT/US2009/064232, mailed Mar. 17, 2010.
Written Opinion for International Application No. PCT/US2010/027437, mailed Jun. 21, 2010.
Written Opinion for International Application No. PCT/US2010/052655, mailed Apr. 4, 2011.
Written Opinion for International Application No. PCT/US2011/037401, mailed Aug. 19, 2011.
Center for Devices and Radiological Health, U.S Food and Drug Administration, "Infusion Pump Improvement Initiative," 7 pages (2010).
Chelly et al., "The Safety and Efficacy of a Fentayl Patient-Controlled Transdermal System for Acute Postoperative Analgesia: A Multicenter, Placebo-Controlled Trial," Anesth. Analg. 98:427-433 (2004).
Culling et al., "Haemodynamics and plasma concentrations following sublingual GTN and intravenous, or inhaled, isosorbide dinitrate," Br. J. Clin. Pharmac. 17:125-131 (1984).
Duncan, "The use of fentanyl and alfentanil sprays for episodic pain," Pall. Med. 16:550 (2002).
Fentora, 2008 Red Book, p. 174.
Griffin et al., "A Phase 2 Open-Label Functionality, Safety, and Efficacy Study of the Sufentanil Nanotaba,,c PCA System in Patients Following Elective Unilateral Knee Replacement Surgery," Reg. Anesth Pain Med. 7, 2 pages (2010).
Ishikawa et al., "The Experiences of Management in Oral Surgery Procedure of WPW Syndrome Patient," J. Jpn. Dental Soc. Anesth. 35:256-257 (2007).
Keohane et al. "Intravenous Medication Safety and Smart Infusion Systems," J. Infus. Nurs. 28(5):321-328 (2005).
Kotey et al., "Iontophoretic delivery of fentanyl for acute post-operative pain management," Eur. J. Hosp. Pharm. Sci. 13(1):3-9 (2007).
Lin et al., "Applying Human Factors to the Design of Medical Equipment:Patient-Controlled Analgesia," J. Clin. Monit. 14:253-263 (1998).
McInnes, F. et al., "Evaluation of the clearance of a sublingual buprenorphine spray in the beagle dog using gamma scintigraphy," Pharmaceutical Research, (2007), 6 pages.

Miaskowski, C., "Patient-controlled modalities for acute postoperative pain management," Journal of PeriAnesthesia Nursing, 20(4):255-267 (Aug. 2005).
Miller, R. D., "The pursuit of excellence. The 47th Annual Rovenstine Lecture," Anesthesiology, 110(4):714-720 (Apr. 2009).
Minkowitz, "A Phase 2 Multicenter, Randomized, Placebo-Controlled Study to Evaluate the Clinical Efficacy, Safety, and Tolerability of Sublingual Sufentanil Nanotab,,c in Patients Following Elective Unilateral Knee REplacement Surgery," Reg. Anesth. Pain Med. 8 (2010).
Momeni, M. et al., "Patient-controlled analgesia in the management of postoperative pain," Drugs, 66(18):2321-2337 (2006).
Paradis et al., "Solid-phase microextraction of human plasma samples for determination of sufentanil by gas chromatography-mass spectrometry," Therapeutic Drug Monitoring, 24:768-774 (2002).
Rawal, N. et al., "Current practices for postoperative pain management in Europe and the potential role of the fentanyl HCl iontophoretic transdermal system," European Journal of Anaesthesiology, 24:299-308 (2007).
Rosati, J. et al., "Evaluation of an oral patient-controlled analgesia device for pain management in oncology inpatients," J. Support. Oncol., 5(9):443-448 (2007).
Rothschild, J. M. et al., "A controlled trial of smart infusion pumps to improve medication safety in critically ill patients," Crit. Care Med., 33(3):533-540 (2005).
Sanford, Jr. et al., "A comparison of morphine, fentanyl, and sufentanil anesthesia for cardiac surgery: induction, emergence, and extubation," Anesthesia and Analgesia, 65:259-266 (1986).
Shojaei, "Buccal mucosa as a route for systemic drug delivery: a review," Journal of Pharmacy and Pharmaceutical Sciences, 1:15-30 (1998).
Singapore Search Report issued in Singapore Patent Application No. 201103689-4 (May 20, 2013).
Slatkin et al., "Fentanyl Buccal Tablet for Relief of Breakthrough Pain in Opioid-Tolerant Patients With Cancer-Related Chronic Pain," J. of Supportive Oncol., vol. 5, No. 7, Jul./Aug. 2007, pp. 327-334.
Stanley and Ashburn, "Novel Delivery Systems: Oral Transmucosal and Intranasal Transmucosal," J. Pain Sympt. Manag. 7(3):163-171 (1992).
Supplementary European Search Report for European Application No. EP 07717774.9 dated Jan. 2, 2013.
Supplementary European Search Report for European Application No. EP 07716451.5 dated Jan. 2, 2013.
Takeuchi et al., "Novel mucoadhesion tests for polymers and polymer-coated particles to design optimal mucoadhesive drug delivery systems," Adv. Drug Deliv. Rev. 57(11):1583-1594 (2005).
Vadivelu, N. et al., "Recent advances in postoperative pain management," Yale Journal of Biology and Medicine, 83:11-25 (2010).
Van Raders, P. et al., "Nurses' views on ease of patient care in postoperative pain management," British Journal of Nursing, 16(5):312-317 (2007).
Vasight, N. et al., "Formulation selection and pharmacokinetic comparison of fentanyl buccal soluble film with oral transmucosal fentanyl citrate," Clin. Drug Investig., 29(10):647-654 (2009).
Vercauteren, M. P. et al., "Epidural sufentanil for postoperative patient-controlled analgesia (PCA) with or without background infusion: a double-blind comparison," Anesth. Analg., 80:76-80 (1995).
Viscusi, E. R., "Patient-controlled drug delivery for acute postoperative pain management: a review of current and emerging technologies," Regional Anesthesia and Pain Medicine, 33(2):146-158 (2008).
Written Opinion for International Application No. PCT/US2007/010822, mailed Aug. 5, 2008.
Written Opinion for International Application No. PCT/US2007/011337, mailed Aug. 21, 2008.

\* cited by examiner

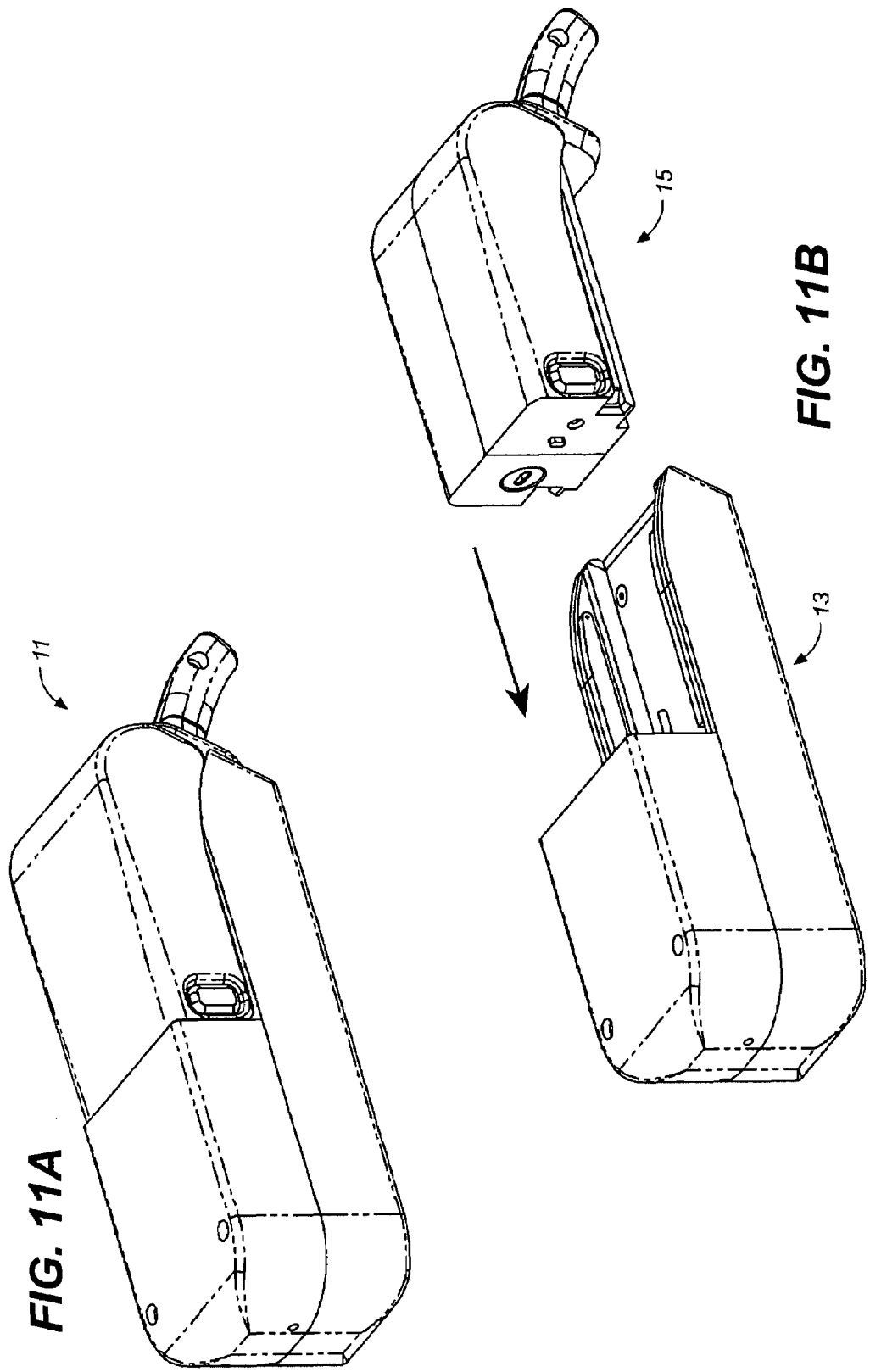

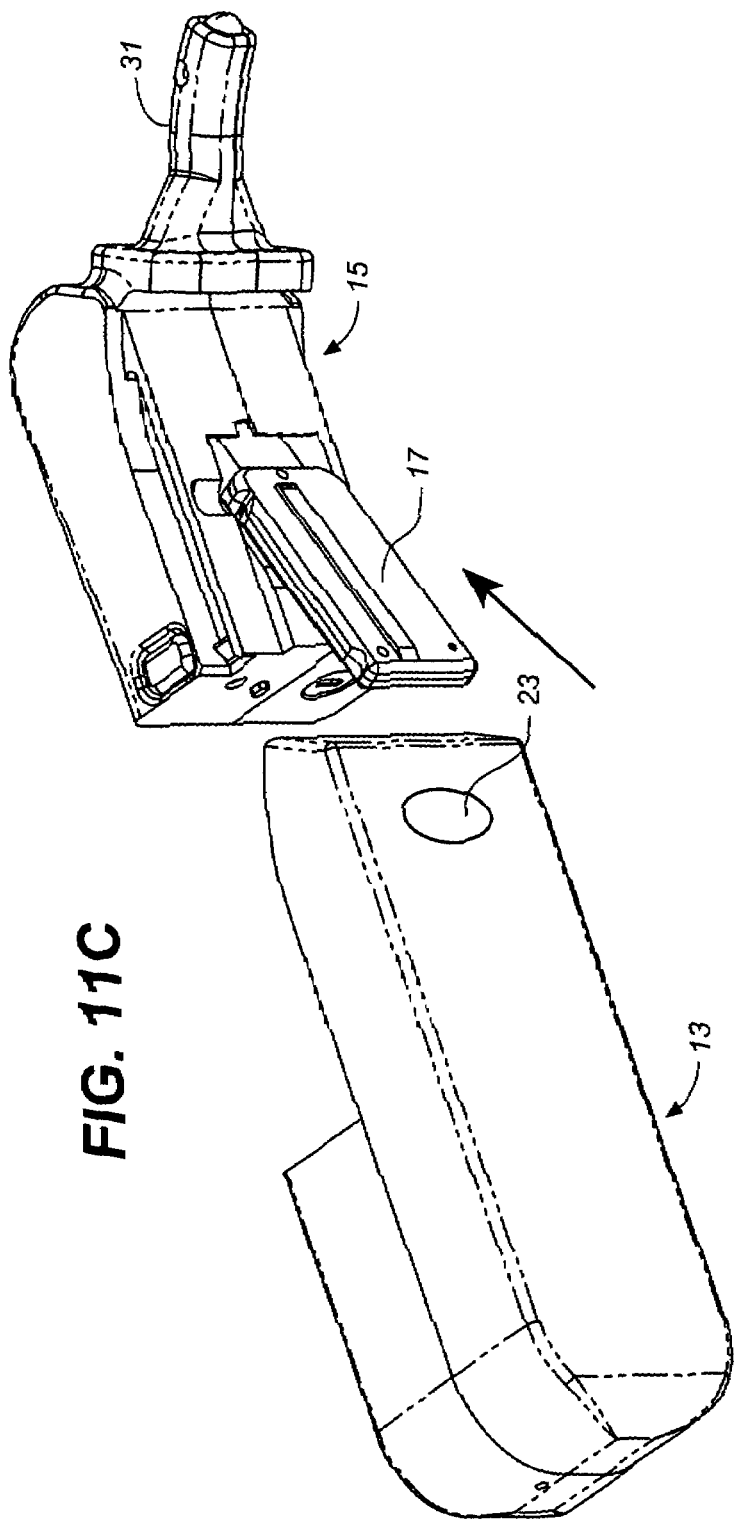

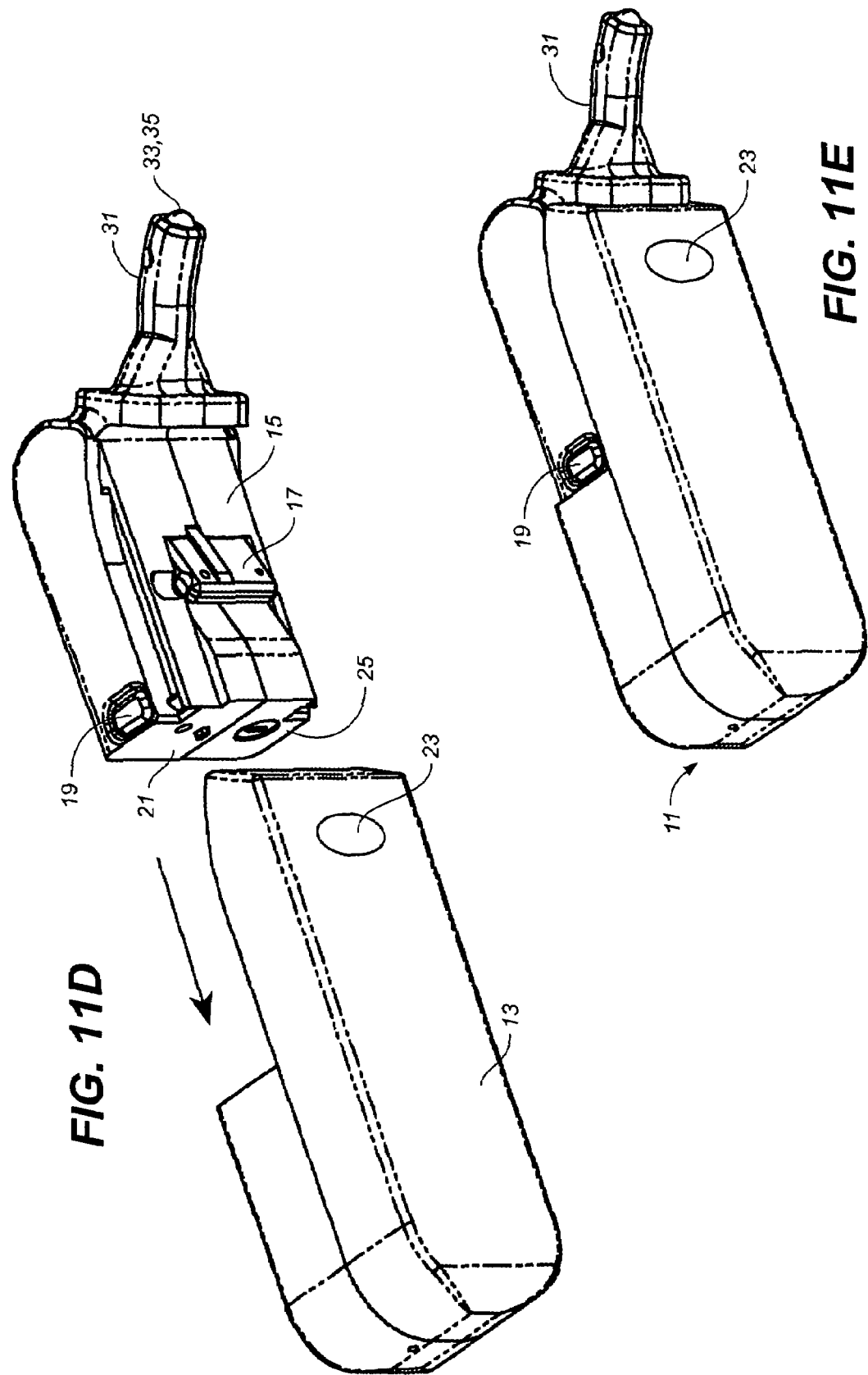

FIG. 16
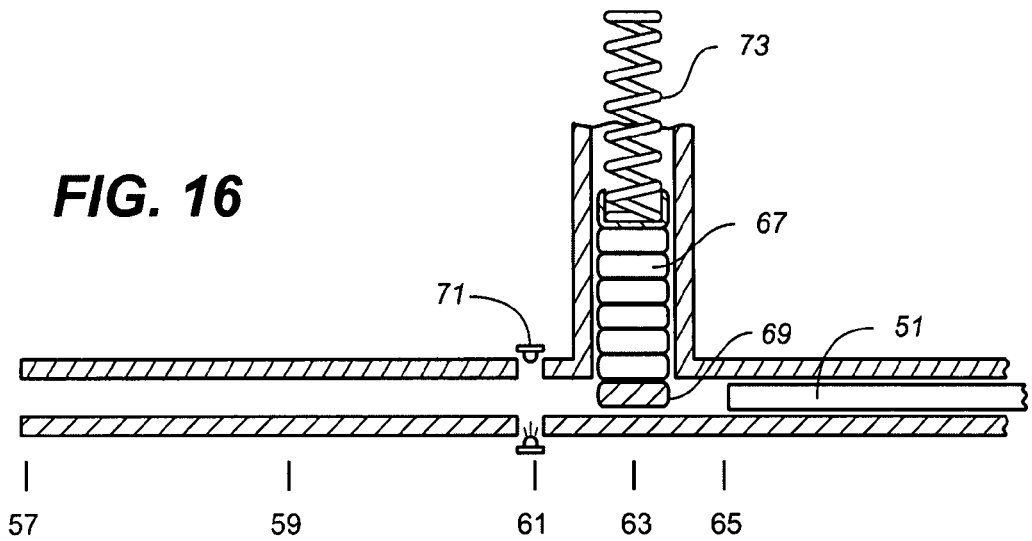
FIG. 17
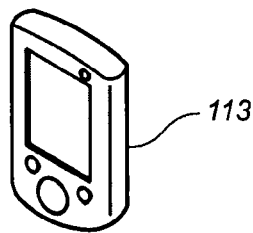
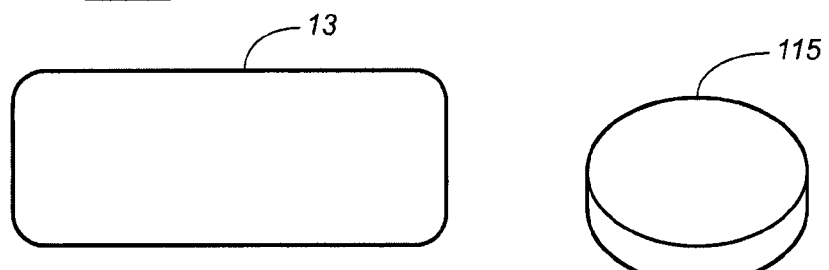
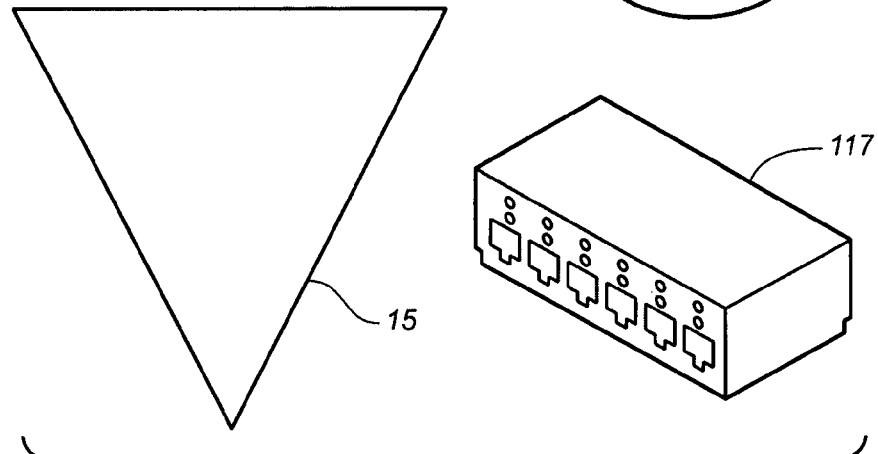

SMALL VOLUME ORAL TRANSMUCOSAL DOSAGE FORMS CONTAINING SUFENTANIL FOR TREATMENT OF PAIN

CROSS-REFERENCE TO RELATED APPLICATIONS

This application is a Continuation-In-Part of U.S. patent application Ser. No. 11/650,174, filed Jan. 5, 2007, which claims priority benefit of U.S. Provisional Application Ser. No. 60/756,937, filed Jan. 6, 2006, the disclosures of which are incorporated by reference herein in their entirety.

FIELD OF THE INVENTION

The invention relates to drug dispensing devices and systems for oral transmucosal administration of small volume drug dosage forms to a subject, wherein the drug dosage forms comprise sufentanil for treatment of pain.

BACKGROUND OF THE INVENTION

Oral dosage forms account for approximately eighty percent of all the drug dosage forms on the market. They are non-invasive, easily administered and have high patient compliance. Orally administered therapeutic agents, however, must be transported to the stomach and small intestine for absorption across the gastrointestinal (GI) mucosal membranes into the blood. The efficiency of absorption of a drug following oral administration can be low because of metabolism within the GI tract and first-pass metabolism within the liver, resulting in relatively lengthy onset times or erratic absorption characteristics that are not well-suited to control acute disorders. The majority of oral dosage forms on the market are designed for GI delivery. Relatively few oral dosage forms are designed for delivery through the oral mucosa.

Oral transmucosal delivery offers a number of advantages in that it can provide a shorter onset time to maximal plasma concentration ($C_{max}$) than oral delivery, in particular for lipophilic drugs. This is because the drug rapidly passes directly and efficiently through the epithelium of the highly vascularized mucosal tissue to the plasma, thus rapidly reaching the circulation while avoiding slower, often inefficient and variable GI uptake. It is therefore advantageous for a drug to be delivered through the mucous membranes of the oral cavity, (e.g., via the sublingual route), when rapid onset, consistent $T_{max}$ and $C_{max}$ are advantageous.

In the process of oral transmucosal drug delivery, the drug is absorbed through the epithelial membranes of the oral cavity. However, frequently the key risk associated with oral transmucosal delivery is the enhanced potential for swallowing the medication owing to the continuous generation, backward flow and swallowing of the saliva. This becomes a particular risk when the dosage forms employed are large enough to produce a significant saliva response, which, in turn, leads to swallowing of drug and/or loss of adherence of the dosage form to the oral mucosa.

Various solid dosage forms, such as sublingual tablets, troches, lozenges, lozenges-on-a-stick, chewing gums, and buccal patches have been used to deliver drugs via the oral mucosal tissue. Solid dosage forms such as lozenges and tablets have been used for oral transmucosal delivery of drugs such as nitroglycerin sublingual tablets.

Reproducible and effective drug delivery technology represents an area of active research, in particular, as it applies to controlled substances such as opioids like sufentanil.

The relevant art does not describe a solid drug dosage form for delivery of sufentanil to the oral mucosa, such as the sublingual space.

Controlled access oral transmucosal drug dispensing systems offer numerous advantages over conventional means of drug administration such as oral and intravenous routes, the most important of which is enhanced safety, with additional advantages being rapid and consistent onset of action, more consistent and predictable plasma concentrations and higher and more consistent bioavailability than currently available dosage forms.

This is particularly relevant to the treatment of pain, more specifically, acute (i.e. post-operative), intermittent and breakthrough pain.

Therefore, a need exists for drug dosage forms, methods and systems for administration of an opioid, such as sufentanil (e.g., by patient-controlled administration), for treatment of pain, wherein the drug dosage form is administered with a device which provides for safe and controlled delivery of the drug via the oral mucosa, while minimizing the potential for drug abuse and/or diversion.

The present invention addresses these needs.

BRIEF SUMMARY OF THE INVENTION

Disclosed herein are dosage forms for sublingual administration of sufentanil to a subject wherein the dosage forms comprise from about 5 to about 100 micrograms (mcg) of sufentanil, and a bioadhesive material, wherein the bioadhesive material provides for adherence to the sublingual mucosa of the subject.

Typically, the dosage forms have a volume of less than 30 microliters or a mass of less than 30 mg.

Erosion of the disclosed dosage forms is complete in from about 6 minutes to about 25 minutes following sublingual administration to a subject and the dosage forms are effective to deliver at least 55%, at least 60%, at least 65%, at least 70%, at least 75%, at least 80%, at least 85%, at least 90%, at least 95%, at least 98% or at least 99% of the total amount of sufentanil in the dosage form via the sublingual route.

A single sublingual administration of the disclosed sufentanil dosage forms to a subject results in one or more of the following: a bioavailability of greater than 50%; an $AUC_{inf}$ with a coefficient of variation of less than 40%; a $T_{max}$ with a coefficient of variation of less than 40%; a linear relationship between $C_{max}$ and the amount of sufentanil in the dosage form; and a linear relationship between $AUC_{inf}$ and the amount of sufentanil in the dosage form.

Repeated sublingual administrations of the disclosed sufentanil dosage forms to a subject results in one or more of the following: a bioavailability which is greater than the bioavailability following a single sublingual administration to the subject; a difference between the $T_{max}$ following repeated sublingual administration and the time of the previous sublingual administration which is shorter than the $T_{max}$ following a single sublingual administration to the subject; and a $T_{max}$ with a coefficient of variation of less than 40%.

The disclosed sufentanil dosage forms find utility in methods for treating pain, wherein a handheld dispensing device is used for placement of a sufentanil dosage form in the sublingual space of a subject. Placement/administration may be patient controlled.

The disclosed handheld dispensing devices comprise one or more of the following features: a housing having a dispensing end with a means to prevent or retard saliva ingress; a lock-out feature; a patient identification feature; and a disposable cartridge configured to hold one or more drug dosage forms. The lock-out feature may provide for repeated sublingual administration of sufentanil at a minimum interval of 20 minutes.

BRIEF DESCRIPTION OF THE DRAWINGS

FIGS. 11A-E provide a schematic depiction of an exemplary dispensing device wherein the device is designed to deliver drug dosage forms to oral mucosa of a patient under treatment. FIGS. 11A-E illustrate the progression of intact drug dispensing device 11 (FIG. 11A); the reusable head 13 and disposable body 15 of a drug dispensing device (FIG. 11B); a reusable head 13, disposable body 15 and cartridge 17, a dispense button 23, and a proboscis 31 of a drug dispensing device (FIG. 11C); various aspects of a drug dispensing device 11 including a reusable head 13, disposable body 15 and cartridge 17, a proboscis 31, and a latch 19 to unlock the device, a hub lock 21, a distal seal 33, 35, and a power train coupling 25 (FIG. 11D); and a reassembled intact drug dispensing device 11 (FIG. 11E).

FIGS. 15A-D provide a series of flow diagrams for use of an exemplary device showing the stages of push rod/tablet interaction during device use, wherein FIG. 15A shows the LOAD feature; FIG. 15B shows the CALIBRATE feature; FIG. 15C shows the DISPENSE feature; and FIG. 15D shows the DISASSEMBLE feature.

FIG. 16 is a schematic depiction of an exemplary device showing the stages of push rod/tablet interaction during device use. In FIG. 16, the push rod 51, dosage forms 67, shipping tablet 69, spring 73 and position sensor 71 are shown. During use, the push rod 51 moves between positions 57, 59, 61, 63, 65 and 67, also shown in FIG. 16.

FIG. 17 is a schematic architecture connection diagram illustrating the various components that may be included in a drug dispensing device or system including a device with a separate drug dispensing device head 13, drug dispensing device body 15, drug cartridge 17, a portable docking FOB 113, a patient RFID tag 115, and a base station 117.

DETAILED DESCRIPTION OF THE INVENTION

I. Introduction

Figure 1:
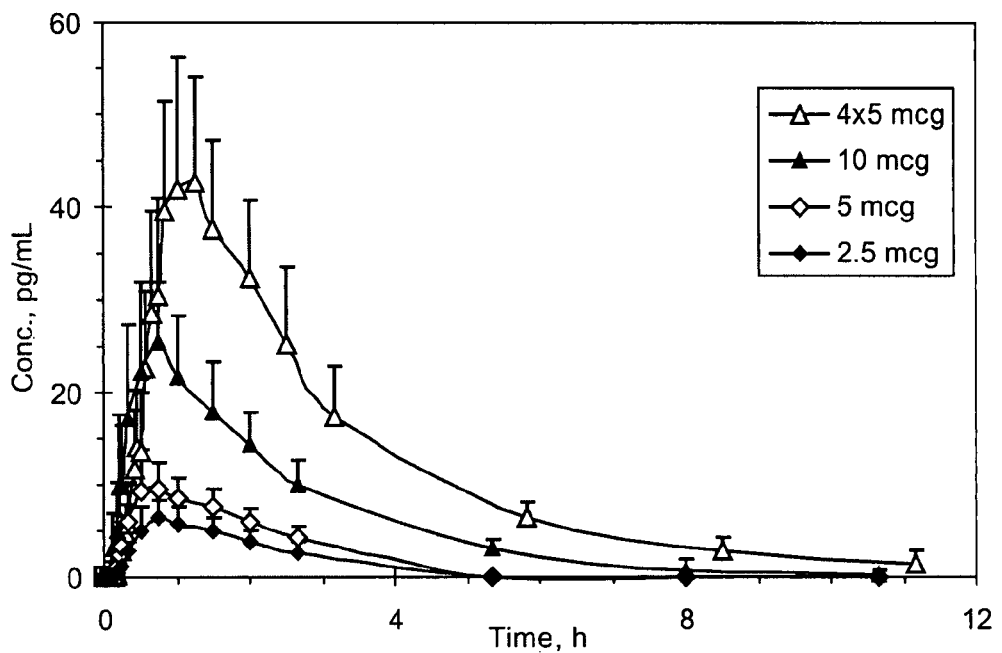
FIG. 1 is a graphic depiction of sufentanil plasma concentration mean+/−standard deviation (SD) versus time, following sublingual administration of 2.5, 5, 10 and 20 mcg (5 mcg every 10 minutes×4 doses) sufentanil dosage forms (slow-eroding) in healthy human volunteers.

Provided herein are compositions, methods, systems and kits for sublingual administration of sufentanil-containing small volume dosage forms using a device. Sublingual administration of the dosage forms minimizes the saliva response and therefore minimizes delivery of the drug to the GI tract, such that the majority of drug is delivered across the oral mucosa. The small volume dosage forms have bioadhesive properties which facilitate adherence to the oral mucosa, thus minimizing the risk of ingestion and inefficient delivery due to swallowing.

The claimed small volume sufentanil-containing dosage forms which are also called "Sublingual Sufentanil Nano- Tabs™" offer a number of advantages in terms of both safety and efficacy as compared to currently available pain treatments.

The following disclosure provides a description of the dosage forms, devices, methods, systems and kits which constitute the invention. The invention is not limited to the specific dosage forms, devices, methodology, systems, kits or medical conditions described herein, as such may, of course, vary. It is also to be understood that the terminology used herein is for the purpose of describing particular embodiments only, and is not intended to limit the scope of the present invention.

It must be noted that as used herein and in the appended claims, the singular forms "a", "and", and "the" include plural references unless the context clearly dictates otherwise. Thus, for example, reference to "a drug formulation" includes a plurality of such formulations and reference to "a drug delivery device" includes systems comprising drug dosage forms and devices for containment, storage and delivery of such dosage forms.

Unless defined otherwise, all technical and scientific terms used herein generally have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in their entirety for the purpose of describing and disclosing the compositions and methodologies which are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

II. Definitions

The term "active agent" or "active" may be used interchangeably herein with the term "drug" and is meant to refer to any therapeutically active agent.

The term "adhere" is used herein with reference to a drug dosage form or formulation that is in contact with a surface such as a mucosal surface and is retained on the surface without the application of an external force. The term "adhere" is not meant to imply any particular degree of sticking or bonding, nor is it meant to imply any degree of permanency.

The term "analgesic drug" as used herein includes sufentanil or a sufentanil congener, such as alfentanil, fentanyl, lofentanil, carfentanil, remifentanil, trefentanil, or mirfentanil, as well as formulations comprising one or more therapeutic compounds. Use of the phrase "sufentanil or a congener" is not meant to be limiting to use of, or formulations comprising, only one of these selected opioid compounds. Furthermore, reference to sufentanil alone or to a selected sufentanil congener alone, e.g., reference to "alfentanil", is understood to be only exemplary of the drugs suitable for delivery according to the methods of the invention, and is not meant to be limiting in any way.

The term "AUC" as used herein means "area under the curve", and is also referred to as "$AUC_{inf}$" in a plot of concentration of drug in plasma versus time. AUC is typically given for the time interval zero to infinity, however, clearly plasma drug concentrations cannot be measured 'to infinity' for a patient so a mathematical equation is used to estimate the AUC from a limited number of concentration measurements.

$AUC_{inf} = AUC_t + C_{last}/\lambda_z$ where $C_{last}$ was the last plasma concentration.

In a practical sense, $AUC_{inf}$ represents the total amount of drug absorbed by the body, irrespective of the rate of absorption. This is useful when trying to determine whether two formulations of the same dose release the same dose of drug to the body. The $AUC_{inf}$ of a transmucosal dosage form compared to that of the same dosage administered intravenously serves as the basis for a measurement of bioavailability.

The term "bioadhesion" as used herein refers to adhesion to a biological surface including mucosal membranes.

The term "bioavailability" or "F" as used herein means "percent bioavailability" and represents the fraction of drug absorbed from a test article as compared to the same drug when administered intravenously. It is calculated from the $AUC_{inf}$ of the test article following delivery via the intended route versus the $AUC_{inf}$ for the same drug after intravenous administration. The absolute bioavailability of sublingual administration was determined by the following formula:

$$F(\%) = \frac{AUC_{inf}^{sublingual}}{AUC_{inf}^{IV}} \times \frac{Dose_{IV}}{Dose_{sublingual}}$$

The term "breakthrough pain" as used herein, is a transitory flare of pain of moderate to severe intensity occurring on a background of otherwise controlled pain. "Breakthrough pain" can be intense for short periods of time, as short as 1 or 2 minutes or as long as 30 minutes or more.

The term "cartridge" is used herein with reference to a disposable cartridge configured to hold one or more drug dosage forms, typically, one up to 200 drug dosage forms. The cartridge typically comprises a smart cartridge recognition system with a physical keyed feature on the cartridge, a bar code on the cartridge, a magnetic tag on the cartridge, an RFID tag on the cartridge, an electronic microchip on the cartridge, or a combination thereof. The cartridge may comprise one or more shipping tablets wherein at least one shipping tablet is dispensed prior to dispensing of a dosage form.

The term "$C_{max}$," as used herein means the maximum observed plasma concentration following administration of a drug.

The term "congener" as used herein refers to one of many variants or configurations of a common chemical structure.

The term "disintegration" is used interchangeably herein with "erosion" and means the physical process by which a dosage form breaks down and pertains to the physical integrity of the dosage form alone. This can occur in a number of different ways including breaking into smaller pieces and ultimately, fine and large particulates or, alternatively, eroding from the outside in, until the dosage form has disappeared.

The term "dispensing device", "drug dispensing device", "dispenser", "drug dispenser", "drug dosage dispenser", "device" and "drug delivery device" are used interchangeably herein and refer to a device that dispenses a drug dosage form. The dispensing device provides for controlled and safe delivery of a pharmaceutically active substance (e.g., an opioid such as sufentanil) formulated in the dosage form. The device may be adapted for storage and/or delivery of a dosage form such as a lozenge, pill, tablet, capsule, membrane, strip, liquid, patch, film, gel, spray or other form.

The term "dispensing end" as used herein with reference to a device means the portion of the device comprising the proboscis and shroud which serves to deliver a drug dosage form to the oral mucosa of a subject.

The term "drug", "medication", "pharmacologically active agent", "therapeutic agent" and the like are used interchangeably herein and generally refer to any substance that alters the physiology of an animal and can be effectively administered by the oral transmucosal route.

The term "erosion time" means the time required for a solid dosage form to break down until the dosage form has disappeared.

The term "FOB" refers to a small, portable handheld, powered electronic docking device that can be used in conjunction with the drug dispensing device to upload data, download data, control access to the drug dispensing device, control access to the drug dosage forms, or enhance or otherwise alter the user interface of the drug dispensing device. A FOB may communicate and dock with a drug dispensing device either in a wired or wireless fashion. A FOB may be adapted to attach to a cord so as to allow the FOB to hang from the neck of a healthcare professional such as a physician or caregiver, particularly in the hospital setting. A drug dispensing device may communicate with the physician or care giver via the FOB.

The terms "formulation" and "drug formulation" as used herein refer to a physical composition containing at least one pharmaceutically active substance, which may be provided in any of a number of dosage forms for delivery to a subject. The dosage form may be provided to the patient as a lozenge, pill, capsule, membrane, strip, liquid, patch, film, gum, gel, spray or other form.

The term "hydrogel-forming preparation", means a solid formulation largely devoid of water which upon contact with an aqueous solution, e.g., a bodily fluid, and in particular that of the oral mucosa, absorbs water in such a way that it forms a hydrated gel in situ. The formation of the gel follows unique disintegration (or erosion) kinetics while allowing for release of the therapeutic agent over time.

The term "lock-out feature" is used herein with reference to a feature of the device which provides for a "lock-out time".

The term "lock-out time" is used herein with reference to the period of time during which the device does not allow drug accessibility, i.e., a dosage form cannot be dispensed during the "lock-out time". "Lock-out time" may be programmable, a fixed time interval, a predetermined interval, a predetermined variable interval, an interval determined by an algorithm or a variable interval communicated to the device from a remote computer or docking station.

The term "LogP" as used herein means logarithm of the ratio of equilibrium concentrations of un-ionized compound between octanol and water. P also called the "octanol-water partition coefficient" and serves as a means to quantify the hydrophobicity or lipophilicity of, a chemical characteristic of a given drug.

The term "mucoadhesion" is used herein in to refer to the adhesion to mucosal membranes which are covered by mucus, such as those in the oral cavity and may be used interchangeably herein with the term "bioadhesion" which refers to adhesion to any biological surface.

The term "mucosal membrane" refers generally to any of the mucus-coated biological membranes in the body. Absorption through the mucosal membranes of the oral cavity is of particular interest. Thus, oral mucosal absorption, i.e., buccal, sublingual, gingival and palatal absorption are specifically contemplated.

The term "mucosal-depot" is used herein in its broadest sense to refer to a reservoir or deposit of a pharmaceutically active substance within or just beneath the mucosal membrane.

The term "non-ordered particulate mixture" or "non-ordered mixture" is used herein with reference to a formulation where the mixture is not ordered with respect to the pharmaceutically active agent and the bioadhesive material or bioadhesion promoting agent, or other formulation components. In addition, it is used herein with reference to any formulation prepared by a process that involves dry mixing wherein drug particles are not uniformly distributed over the surface of larger carrier particles. Such 'non-ordered' mixing may involve dry mixing of particles in a non-ordered fashion, where there is no requirement with respect to the order of addition/mixing of specific excipients with the drug, bioadhesive material or bioadhesion promoting agent and/or disintegrants. Further in the non-ordered mixing process, there is no limitation on the size of the drug particles. The drug particles may be larger than 25 µm. In addition, a "non-ordered mixture" includes any mixing processes in which the primary carrier particles do not incorporate a disintegrant within. Finally the "non-ordered mixture" may be prepared by any 'wet mixing' processes, i.e. processes in which a solvent or non-solvent is added during the mixing process or any mixing process in which the drug is added in a solution or suspension form.

The term "operatively connected" as used herein means the components are provided in a device so as to function as intended to achieve an aim. For example, a memory device operatively connected to a CPU which is further operatively connected to a release mechanism may be meant to indicate that, upon actuation, the CPU communicates with the memory device to check the status or history of drug delivery, and then further communicates with the release mechanism (e.g., via a solenoid and a switch) to release and dispense a drug.

The term "opioid naïve patient" is used herein with reference to a patient who has not received repeated administration of an opioid substance over a period of weeks to months.

The term "opioid tolerant patient" as used herein means a physiological state characterized by a decrease in the effects of an opioid substance (e.g., analgesia, nausea or sedation) with chronic administration. An opioid substance is a drug, hormone, or other chemical substance that has analgesic, sedative and/or narcotic effects similar to those containing opium or its derivatives. If analgesic tolerance develops, the dose of opioid substance is increased to result in the same level of analgesia. This tolerance may not extend to side effects and side effects may not be well tolerated as the dose is increased.

The terms "oral transmucosal dosage form" and "drug dosage form" may be used interchangeably herein and refer to a dosage form which comprises a pharmaceutically active substance, e.g., a drug such as sufentanil. The oral dosage form is used to deliver the pharmaceutically active substance to the circulation by way of the oral mucosa and is typically a "sublingual dosage form", but in some cases other oral transmucosal routes may be employed. The dosage form provides for delivery of the pharmaceutically active substance across the oral mucosa and by controlling the formulation the timing for release of the pharmaceutically active substance can be achieved. The dosage form comprises pharmaceutically acceptable excipients and may be referred to as a NanoTab™, as detailed in U.S. application Ser. No. 11/650,174, expressly incorporated by reference herein. The dosage form comprises a formulation that is neither effervescent nor does it comprise an essentially water-free, ordered mixture of microparticles of drug adhered to the surface of carrier particles, where the carrier particles are substantially larger than the microparticles of drug.

The terms "oral transmucosal drug delivery" and "oral transmucosal administration" as used herein refer to drug delivery that occurs substantially via the transmucosal route and not via swallowing followed by GI absorption. Maximal delivery occurs via the oral mucosa, typically by placement of the dosage form within the sublingual cavity.

The term "proboscis" is used interchangeably with the terms "dispensing tip" a "delivery tip", and refers to a dispensing and/or positioning tip of a drug dosage form dispenser that delivers a dosage form to the oral mucosa (e.g., the sublingual space).

The term "radio frequency identification device" or "RFID" is used with reference to an automatic identification method, which relies on storing and remotely retrieving data using devices called RFID tags, wherein the RFID tag is applied to, or incorporated into a product, or person for the purpose of identification using radiowaves. Some tags can be read from several meters away and beyond the line of sight of the reader.

The term "replaceable cartridge" or "disposable cartridge" is used with reference to a cartridge for housing drug dosage forms which is typically configured to hold up to 200 drug dosage forms, wherein the cartridge is designed to be used and discarded.

The term "shipping tablet" is used herein with reference to an "initialization", or "shipping" tablet which is the same size and shape as a drug-containing dosage form but does not contain a pharmaceutically active substance. The "shipping tablet" may comprise a placebo dosage form that does not contain a pharmaceutically active substance or may be made of plastic or other material. It is the first thing dispensed from a new cartridge after insertion into a dispensing device. The device has a means for differentiating between the shipping tablet and a dosage form containing a pharmaceutically active substance.

The term "shroud" is used to describe a partial or complete covering of the dispensing end of the device which protects the delivery port from contact with saliva or other moisture in the oral cavity and forms a barrier between the device, the oral mucosa and tongue, has a relief for dosage form delivery, and an interior that is hydrophobic or hydrophilic which serves to minimize or eliminate saliva ingress or moisture ingress. The "shroud" creates a barrier from the oral mucosa contacting the valve area and dosage form, aiding in dosage form dispensing and discouraging dosage form adherence to the shroud. The shroud may have a rounded interior surface or other geometry to stop the dosage form adhering to the shroud. The shroud limits the ability of the tongue or sublingual mucosa to contact the dosage form dispensing area, thereby controlling saliva contact and ingress.

The term "subject" includes any subject, generally a mammal (e.g., human, canine, feline, equine, bovine, ungulate etc.), adult or child, in which treatment for a disorder is desired. The terms "subject" and "patient" may be used interchangeably herein.

The term "systems that include a drug dosage form and a dispensing device" as used herein refers to a drug dispensing system for delivery and/or monitoring of drug administration. The system may be used to monitor and deliver a pharmaceutically active substance, e.g., an opioid such as sufentanil, wherein the amount of drug delivered, corresponding efficacy and safety are enhanced over currently available systems. The system may have one or more features that provide for improved safety and ease of use over currently available systems including a security feature that prevents unauthorized access to the stored drugs, a dosing lock-out feature, a means for identifying an individual patient for controlled drug access, a dose counting feature, a memory means for retaining information about dose delivery, and an interface for bidirectional exchange of information with a user, a drug cartridge, or another device such as a computer.

The term "small volume drug dosage form" or "small volume dosage form" is used herein with reference to a small volume dosage form that has a volume of less than 100 µl and a mass of less than 100 mg. More specifically, the dosage form has a mass of less than 100 mg, 90 mg, 80 mg, 70 mg, 60 mg, 50 mg, 40 mg, 30 mg, 29 mg, 28 mg, 27 mg, 26 mg, 25 mg, 24 mg, 23 mg, 22 mg, 21 mg, 20 mg, 19 mg, 18 mg, 17 mg, 16 mg, 15 mg, 14 mg, 13 mg, 12 mg, 11 mg, 10 mg, 9 mg, 8 mg, 7 mg, 6 mg or 5 mg or a volume of less than 100 µl, 90 µl, 80 µl, 70 µl, 60 µl, 50 µl, 40 µl, 30 µl, 29 µl, 28 µl, 27 µl, 26 µl, 25 µl, 24 µl, 23 µl, 22 µl, 21 µl, 20 µl, 19 µl, 18 µl, 17 µl, 16 µl, 15 µl, 14 µl, 13 µl, 12 µl, 11 µl, 10 µl, 9 µl, 8 µl, 7 µl, 6 µl or 5 µl. The "dosage form" may or may not have bioadhesive characteristics and may form a hydrogel upon contact with an aqueous solution.

The "dosage form" may be used to deliver any drug that can be administered by the oral transmucosal route in an amount amenable to administration via the small size of the dosage form, i.e. 0.25 µg to 99.9 mg, 1 µg to 50 mg or 1 µg to 10 mg.

The term "small volume sufentanil-containing drug dosage form" is used herein with reference to a small volume dosage form that contains a dose of sufentanil selected from about 2 micrograms (mcg) to about 200 mcg of sufentanil, e.g., 5 mcg, 10 mcg, 15 mcg, 20 mcg, 30 mcg, 40 mcg, 50 mcg, 60 mcg, 70 mcg, 80 mcg or 100 mcg of sufentanil.

The term "solid dosage form" or "solid drug dosage form" is used herein with reference to a small volume dosage form that is a solid, e.g., a lozenge, a pill, a tablet, a membrane or a strip.

The term "sublingual", means literally "under the tongue" and refers to administering a drug dosage form via the mouth in such a way that the pharmaceutically active substance is rapidly absorbed via the blood vessels under the tongue rather than via the digestive tract. Absorption occurs via the highly vascularized sublingual mucosa and allows the pharmaceutically active substance more direct access to the blood circulation, providing for direct systemic administration independent of GI influences.

The term "terminal half-life" or "$t_{1/2}$ [h]" as defined herein is calculated as $\ln(2)/\lambda_2$ (defined as the first order terminal rate constant estimated by linear regression of the time versus log concentration curve) and also determined after the final dosing in repeated dose studies.

The term "$T_{max}$" as used herein means the time point of maximum observed plasma concentration.

The term "$T_{onset}$" as used herein means the observed "time of onset" and represents the time required for the plasma drug concentration to reach 50% of the maximum observed plasma concentration, $C_{max}$.

The term "therapeutically effective amount" means an amount of a therapeutic agent, or a rate of delivery of a therapeutic agent (e.g., amount over time), effective to facilitate a desired therapeutic effect, such as pain relief. The precise desired therapeutic effect (e.g., the degree of pain relief, and source of the pain relieved, etc.) will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

The term "transmucosal" delivery of a drug and the like is meant to encompass all forms of delivery across or through a mucosal membrane. In particular, "oral transmucosal" delivery of a drug includes delivery across any tissue of the mouth, pharynx, larynx, trachea, or upper gastrointestinal tract, particularly including the sublingual, gingival and palatal mucosal tissues.

III. Drug Dosage Forms

The claimed small volume sublingual drug dosage forms produce a reduced saliva response as compared with conventional, larger dosage forms that are intended to deliver a drug in the oral cavity.

The preferred site for oral transmucosal drug delivery is the sublingual area, although in certain embodiments it may be advantageous for the dosage form to be placed inside the cheek, or to adhere to the roof of the mouth or the gum.

Sublingual delivery is preferred as the sublingual mucosa is more readily permeable to medications than other mucosal areas, such as the buccal mucosa, resulting in more rapid uptake.

The dosage forms provide for the delivery of a greater percentage (and amount) of the drug via the oral mucosa and a corresponding decrease in delivery via the gastrointestinal (GI) tract as compared to traditional oral dosage forms and other oral transmucosal dosage forms.

Typically, the dosage forms are adapted to adhere to the oral mucosa (i.e. are bioadhesive) during the period of drug delivery, and until most or all of the drug has been delivered from the dosage form to the oral mucosa.

More specifically, the dosage forms have a mass of less than 100 mg, 90 mg, 80 mg, 170 mg, 60 mg, 50 mg, 40 mg, 30 mg, 29 mg, 28 mg, 27 mg, 26 mg, 25 mg, 24 mg, 23 mg, 22 mg, 21 mg, 20 mg, 19 mg, 18 mg, 17 mg, 16 mg, 15 mg, 14 mg, 13 mg, 12 mg, 11 mg, 10 mg, 9 mg, 8 mg, 7 mg, 6 mg or 5 mg or a volume of less than 100 µl, 90 µl, 80 µl, 70 µl, 60 µl, 50 µl, 40 µl, 30 µl, 29 µl, 28 µl, 27 µl, 26 µl, 25 µl, 24 µl, 23 µl, 22 µl, 21 µl, 20 µl, 19 µl, 18 µl, 17 µl, 16 µl, 15 µl, 14 µl, 13 µl, 12 µl, 11 µl, 10 µl, 9 µl, 8 µl, 7 µl, 6 µl or 5 µl.

In a preferred embodiment, the claimed dosage forms have a mass of less than 30 mg and a volume of less than 30 ul.

The dosage forms typically have bioadhesive characteristics and may form a hydrogel upon contact with an aqueous solution.

The dosage forms typically have an erosion time of from about 6 minutes or up to 25 minutes, however the erosion time may vary. More specifically, the dosage forms typically have an erosion time of about 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes or 25 minutes.

In general, at least 55%, at least 60%, at least 65%, at least 70%, at least 75%, at least 80%, at least 85%, at least 90%, at least 95%, at least 98% or at least 99% of the total amount of pharmaceutically active substance in a dosage form administered to the oral mucosa of a subject is absorbed via the oral transmucosal route.

The dosage forms may have essentially any shape, examples of which include a round disc with a flat, concave, or convex face, an ellipsoid shape, a spherical shape, a polygon with three or more edges and flat, concave, or convex faces. The dosage forms may be symmetrical or asymmetrical, and may have features or geometries that allow for controlled, convenient, and easy storage, handling, packaging or dosing.

Oral transmucosal drug delivery is simple, non-invasive, and can be accomplished by a caregiver or patient with minimal discomfort. A dosage form for oral transmucosal delivery may be solid or non-solid. In one preferred embodiment, the dosage from is a solid that turns into a hydrogel following contact with saliva. In another preferred embodiment, the dosage from is a solid that erodes without forming a hydrogel following contact with saliva.

Generally, oral transmucosal delivery of pharmaceutically active substances is achieved using solid dosage forms such as lozenges or tablets, however, liquids, sprays, gels, gums, powders, and films and the like may also be used.

For certain drugs, such as those with poor bioavailability via the GI tract, e.g., lipophilic opioids such as sufentanil, oral transmucosal delivery is a more effective delivery route than GI delivery. For such lipophilic drugs, oral transmucosal delivery has a shorter onset time (i.e., the time from administration to therapeutic effect) than does oral GI delivery and provides better bioavailability and more consistent pharmacokinetics.

The small size of the claimed drug dosage forms is designed to reduce the saliva response, thus reducing the amount of drug swallowed, and thereby delivering a substantial amount of drug to a subject via the oral mucosa. The claimed drug dosage forms provide for efficacious delivery of sufentanil via the oral mucosa and a consistent plasma level within the therapeutic window.

Formulations for preparation of the claimed dosage forms and methods of making them are described in U.S. application Ser. Nos. 11/825,251 and 11/650,227, expressly incorporated by reference herein. An exemplary formulation is bioadhesive and comprises from about 0.0004% to about 0.04% sufentanil, e.g., 0.0005%, 0.001%, 0.002%, 0.003%, 0.004%, 0.006%, 0.008%, 0.01%, 0.012%, 0.014% or 0.016% sufentanil. In general, the formulation comprises (a) a non-ordered mixture of a pharmaceutically active amount of a drug; (b) a bioadhesive material which provides for adherence to the oral mucosa of the subject; and (c) stearic acid, wherein dissolution of a dosage form comprising the formulation is independent of pH, e.g., over a pH range of about 4 to 8.

Numerous suitable nontoxic pharmaceutically acceptable carriers for use in oral dosage forms can be found in Remington's Pharmaceutical Sciences, 17th Edition, 1985.

It will be understood that the formulation is converted into a dosage form for delivery to a subject using procedures routinely employed by those of skill in the art, such as direct compression, wet granulation, etc. The process for preparation of the dosage form is optimized for each formulation in order to achieve high dose content uniformity.

While not wishing to be bound by theory, when a claimed dosage form is placed in the sublingual cavity, preferably under the tongue on either side of the frenulum linguae, it adheres upon contact. As the dosage form is exposed to the moisture of the sublingual space the dosage form absorbs water, resulting in erosion of the dosage form and release of the drug to the circulation of the subject.

IV. Sufentanil

Opioids are widely used for the treatment of pain, and are generally delivered intravenously, orally, epidurally, transdermally, rectally and intramuscularly. Morphine and its analogues are commonly delivered intravenously and are effective against severe, chronic and acute pain. However, they can also have severe respiratory depressive effects if not used appropriately and also suffer from a high abuse potential. The predominant cause of morbidity and mortality from pure opioid overdoses is due to respiratory complications.

Sufentanil (N-[(4-(Methoxymethyl-1-(2-(2-thienyl) ethyl)-4-piperidinyl)]-N-phenylpropanamide), is used as a primary anesthetic, to produce balanced general anesthesia in cardiac surgery, for epidural administration during labor and delivery and has been administered experimentally in both intranasal and liquid oral formulations. A commercial form of sufentanil used for IV delivery is the SUFENTA FORTE® formulation. This liquid formulation contains 0.075 mg/ml sufentanil citrate (equivalent to 0.05 mg of sufentanil base) and 9.0 mg/ml sodium chloride in water. It has a plasma elimination half-life of 148 minutes, and 80% of the administered dose is excreted in 24 hours.

The use of sufentanil clinically has predominantly been limited to IV administration in operating rooms or intensive care units. There have been a few studies on the use of liquid sufentanil preparations for low-dose intranasal administration (Helmers et al., 1989; Jackson K, et al., J Pain Symptom Management 2002: 23(6): 450-452) and case reports of sublingual delivery of a liquid sufentanil preparation (Gardner-Nix J., J Pain Symptom Management. 2001 August; 22(2): 627-30; Kunz K M, Theisen J A, Schroeder M E, Journal of Pain and Symptom Management, 8:189-190, 1993). In most of these studies, the smallest dosing of sufentanil in adults was 5 mcg in opioid naïve patients. Liquid administered to the oral or nasal mucosa suffers from lower bioavailability and possibly a shorter duration of action as demonstrated by the animal studies (sublingual liquid) described herein, as well as the literature (nasal liquid drops—Helmers et al., 1989). Gardner-Nix provides analgesic data (not pharmacokinetic data) produced by liquid sublingual sufentanil and describes the analgesic onset of liquid sublingual sufentanil occurring within 6 minutes but the duration of pain relief lasted only approximately 30 minutes.

A number of opioid dosage forms many of which contain fentanyl are currently available for treatment of pain.

Following transbuccal administration of fentanyl using a lozenge (e.g., Actiq®), the bioavailability is 50%, although the $T_{max}$ for the 200 mcg dosage of Actiq® ranges from 20-120 minutes resulting from erratic GI uptake due to the fact that 75% of the fentanyl is swallowed (Actiq® package insert). More recent publications on the $T_{max}$ of Actiq indicate that these original times were skewed towards more rapid onset (Fentora package insert indicates a range of $T_{max}$ for Actiq extending up to 240 minutes). Fentora (a fentanyl buccal tablet) exhibits a bioavailability of 65%, with reported swallowing of 50% of the drug. In contrast to the claimed dosage forms, both Actiq® and Fentora suffer from the disadvantage that substantial amounts of lozenge-administered fentanyl are swallowed by the patient.

Sufentanil and fentanyl have many similarities as potent mu-opioid receptor agonists, however, they have been shown to differ in many key ways. Multiple studies have demonstrated sufentanil to be in the range of 7-24 times more potent than fentanyl (SUFENTA® package insert; Paix A, et al. Pain, 63:263-69, 1995; Reynolds L, et al., Pain, 110:182-188, 2004). Therefore, sufentanil may be administered using a smaller dosage form, avoiding the increased saliva response of a larger dosage form and thereby minimizing the amount of drug that is swallowed. This leads to minimal GI uptake.

In addition, fentanyl and other opiate agonists, have the potential for deleterious side effects including respiratory depression, nausea, vomiting and constipation.

There is evidence which suggests that sufentanil may have less respiratory depression than fentanyl and other opioids at clinical doses (Ved et al., 1989; Bailey et al., 1990; Conti et al., 2004).

Since fentanyl has a 30% bioavailability from the GI route, swallowed drug can contribute to the $C_{max}$ plasma levels to a significant degree and results in the erratic $C_{max}$ and $T_{max}$ observed with these products. In contrast, the bioavailability of sufentanil from the GI route is 10-12%, and therefore swallowed drug will not contribute to the $C_{max}$ plasma levels to a significant degree.

Further, the lipid solubility (octanol-water partition coefficient) of sufentanil (1778:1) is greater than fentanyl (816:1) (van den Hoogen and Colpaert, Anesthes. 66:186-194, 1987). Sufentanil also displays increased protein binding (91-93%) compared with fentanyl (80-85%) (SUFENTA® and Actiq® package inserts, respectively). Sufentanil has a pKa of 8.01, whereas the pKa of fentanyl is 8.43 (Paradis et al., Therapeutic Drug Monitoring, 24:768-74, 2002). These differences can affect various pharmacokinetic parameters, for example, sufentanil has been shown to have a faster onset of action and faster recovery time than fentanyl (Sanford et al., Anesthesia and Analgesia, 65:259-66, 1986). As compared to fentanyl, use of sufentanil can result in more rapid pain relief with the ability to titrate the effect and avoid overdosing.

Importantly, sufentanil has been shown to produce endocytosis of the mu-opioid receptor 80,000 times more potently than fentanyl (Koch et al., Molecular Pharmacology, 67:280-87, 2005). The result of this receptor internalization is that neurons continue to respond to sufentanil more robustly over time than with fentanyl, suggesting that clinically less tolerance would develop to sufentanil compared to fentanyl with repeated dosing.

Prior to the work of the current inventors, no pharmacokinetic data had been published on sublingual sufentanil in any form. Pharmacokinetic data for ocular and intranasal transmucosal delivery of sufentanil has been published based on studies in dogs and humans. Farnsworth et al. (Anesth Analg, 1998, 86:138-140) describe ocular transmucosal absorption and toxicity of sufentanil in dogs, where 50 mcg of sufentanil was administered over a period of 2.5 minutes to the conjuctiva of five anesthetized dogs. The $T_{max}$ occurred at 5 min with a $C_{max}$ of 0.81 ng/mL and a $t_{1/2}$ of approximately 18 minutes. A study report of intranasal and intravenous administration of 15 mcg of sufentanil in 16 humans provides a comparison of pharmacokinetic profiles, where intranasal sufentanil was delivered via 3 drops in each nostril with 2.5 mcg/drop. Intranasal sufentanil had a 78% bioavailability based on the AUC from 0-120 minutes compared with intravenous delivery. Intranasal delivery resulted in a $T_{max}$ of 10 minutes with a $C_{max}$ of 0.08 ng/mL. The $t_{1/2}$ was approximately 80 minutes. See, Helmers et al., Can J Anaesth. 6:494-497, 1989. A third study in pediatric patients describes preoperative intranasal dosing of 15 children with 2 mcg/kg sufentanil via nasal drops and with, plasma levels of sufentanil measured starting at 15 minutes, which was too late to capture the $T_{max}$. Based on extrapolation of the data, the $C_{max}$ was approximately 0.3 ng/mL and the $t_{1/2}$ was approximately 75 minutes (Haynes et al., Can J Anaesth. 40(3):286, 1993).

Sufentanil Dosage Forms

The active agent in the claimed dosage forms is sufentanil, alone or in combination with a sufentanil congener such as alfentanil, fentanyl, lofentanil, carfentanil, remifentanil, trefentanil, or mirfentanil. In a preferred embodiment, sufentanil alone is the active agent. Sufentanil may be provided in the claimed dosage forms in any of a number of formulations.

Sufentanil may be provided as sufentanil citrate, sufentanil base, or a combination thereof.

A sufentanil drug dosage form may contain from about 0.25 to about 200 mcg of sufentanil per dosage form for sublingual delivery. In one exemplary embodiment, each dosage form contains from about 0.25 to about 200 mcg of sufentanil, alone or combination with one or more other therapeutic agents or drugs.

Exemplary drug dosage forms for administration to children (pediatric patients) contain from about 0.25 to about 120 mcg of sufentanil per dosage form. For example, a drug dosage form for administration to children may contain about 0.25, 0.5, 1, 2.5, 4, 5, 6, 8, 10, 15, 20, 40, 60 or 120 mcg of sufentanil for oral transmucosal delivery. It follows that for pediatric patients, an exemplary dose range is from at least about 0.02 mcg/kg to about 0.5 mcg/kg with a preferable range of from about 0.05 to about 0.3 mcg/kg.

Exemplary drug dosage forms for administration to adults contain from about 2.5 to about 200 mcg of sufentanil per dosage form. For example, a drug dosage form for administration to adults may contain about 2.5, 3, 5, 7.5, 10, 15, 20, 40, 60, 80, 100, 120, 140, 180 or 200 mcg or more of sufentanil for oral transmucosal delivery.

Preferably, a sufentanil-containing dosage form comprises from about 5 to about 100 micrograms (mcg) of sufentanil, e.g., 5 mcg, 10 mcg, 15 mcg, 20 mcg, 30 mcg, 40 mcg, 50 mcg, 60 mcg, 70 mcg, 80 mcg or 100 mcg of sufentanil.

As will be understood by those of skill in the art, the dose will be on the low end of the range for children and the high end of the range for adults dependent upon body mass, in particular when administered long term to opioid-tolerant adults. Prior to the work of the current inventors, small-volume sufentanil-containing dosage forms for oral transmucosal drug delivery had not been described.

In various embodiments, the claimed dosage forms provide effective pain relief in all types of patients including children, adults of all ages who are opioid tolerant or naïve and non-human mammals. The invention finds utility in both the inpatient and outpatient setting and in the field.

Congeners of Sufentanil

Congeners of sufentanil find use in the compositions, methods and systems described herein, examples of which include alfentanil, lofentanil, carfentanil, remifentanil, trefentanil or mirfentanil.

In certain embodiments, the dosage form comprises at least 0.005% to as much as 99.9% by weight of alfentanil, lofentanil, carfentanil, remifentanil, trefentanil or mirfentanil. The percentage of active ingredient(s) will vary dependent upon the size of the dosage form and nature of the active ingredient(s), optimized to obtain maximal delivery via the oral mucosal route. In some aspects of the invention, more than one active ingredient may be included in a single dosage form.

V. Treatment of Pain

Using current treatment methods, pain control is attempted using a number of interventions, which generally include: patient-controlled analgesia (PCA), continuous epidural infusion (CEI), other types of acute pain control, palliative care pain control, and home health patient pain control. These methods meet with varying degrees of success with respect to duration of control, ease of treatment and safety versus side effects.

The need for rapid treatment of acute pain occurs in many different clinical situations, including post-operative recuperation, rheumatoid arthritis, failed back, end-stage cancer (i.e., breakthrough pain), etc. Post-operatively, for example, patients suffer from severe pain for the first few days followed by days of mild to moderate levels of pain.

The most common analgesic used to treat moderate to severe post-operative pain is IV morphine. This is either delivered on an "as needed" basis to the patient by a nurse using IV injection or commonly a morphine syringe is placed in a PCA pump and the patient self-administers the opioid by pressing a button which has a lock-out feature. Other opioids, such as hydromorphone and fentanyl may also be administered in this manner.

Treatment of acute pain is also necessary for patients in an outpatient setting. For example, many patients suffer from chronic pain and require the use of opioids on a weekly or daily basis to treat their pain. While they may have a long-acting oral or transdermal opioid preparations to treat their chronic underlying pain levels, they often need short-acting potent opioids to treat their severe breakthrough pain levels.

Treatment of acute pain is also necessary "in the field" under highly sub-optimal conditions. Paramedics or military medics often are required to treat severe acute pain in un-sterile situations, where needles used for IV or IM administration can result in unintended needle sticks, risk of infection, etc. Oral opioid tablets often take 60 minutes to provide relief which is too long for someone in severe pain.

In a number of clinical settings, there is clearly a need for improved means to administer a drug that produces effective pain relief in a manner that is titratable, safe and convenient, and non-invasive that provides relief from acute, severe breakthrough or intermittent pain over an appropriate period of time.

The claimed compositions, methods and systems rely on administration of dosage forms comprising a pharmaceutically active substance such as sufentanil which is effective for the treatment of acute pain (i.e. post-operative pain), intermittent pain or breakthrough pain, using a dispensing device that includes features such as lock-out, a means for patient identification prior to drug administration and a means to protect the dosage forms stored in the dispensing device. The claimed methods and systems thereby provide significant advantages over currently available treatment modalities in terms of both safety and efficacy.

VI. In Vivo Human Studies

Provided herein is pharmacokinetic data obtained in humans based on studies where sufentanil was administered via the sublingual route using the claimed small volume dosage forms.

Two human clinical studies were performed using healthy human volunteers. The first study which is detailed in Example 1 was performed with 12 subjects (6 men and 6 women) using slow-eroding sublingual sufentanil dosage forms containing either 2.5 mcg, 5 mcg or 10 mcg of sufentanil base corresponding to 3.7 mcg, 7.5 mcg or 15 mcg of sufentanil citrate, respectively in comparison to a 10-minute IV infusion of 5 mcg sufentanil or 4 repeated doses of a slow-eroding sublingual sufentanil dosage form containing 5 mcg sufentanil administered at 10-minute intervals (Table 1). The second study which is detailed in Example 2 was performed with 11 subjects using faster-eroding sublingual sufentanil dosage forms containing either 10 mcg or 80 mcg of sufentanil base corresponding to 15 mcg or 120 mcg of sufentanil citrate, respectively, in comparison to a 10-minute IV infusion of 10 mcg sufentanil or a 20-minute IV infusion of 50 mcg sufentanil, a sublingual dose of 5 mcg of sufentanil solution or 4 repeated administrations of fast-eroding sublingual sufentanil dosage forms containing 10 mcg of sufentanil administered at 20-minute intervals (Table 2). All excipients were "pharmaceutically acceptable" (inactive) and have GRAS or "generally recognized as safe" status.

Sufentanil dosage forms designed for sublingual use were compared to IV sufentanil, administered through an IV catheter as a continuous infusion. Plasma samples were drawn from a different IV catheter at a remote location. The assay demonstrated good inter-day precision and accuracy at the high, medium and low quality control sample concentrations.

The dosage forms for the first study eroded over a period of 15-25 minutes in all subjects and are designated herein as "slow-eroding". The dosage forms for the second study eroded over a period of 6-12 minutes in all subjects and are designated herein as "faster-eroding". After placement of each sufentanil dosage form in the sublingual cavity of the healthy volunteers, a remarkably consistent pharmacokinetic profile was obtained. The bioavailability of sufentanil administered using small volume sublingual dosage forms as compared to IV administration for single and multiple administrations was high and ranged from 60.9% (10 mcg dose; faster-eroding) to 97.2% (4×5 mcg dose (slow-eroding). The bioavailability of sufentanil administered using small volume sublingual dosage forms is greater than that of the fentanyl products, Actiq and Fentora (47% and 65%, respectively—Fentora package insert). Importantly, the bioavailability is linked to the consistency of total drug delivered to the patient. For example, the total plasma drug area under the curve (AUC 0-infinity) for sufentanil dosage forms 10 mcg was 0.0705±0.0194 hr*ng/ml (mean±standard deviation (SD)). This SD is only 27.5% of the total AUC. Coefficient of variation (CV) is a term to describe the percent SD of the mean. The coefficient of variation for the fentanyl products, Fentora (AUC is 45%) and Actiq (AUC is 41%; Fentora package insert), while the coefficient of variation around the bioavailability of sufentanil administered using small volume sublingual dosage forms is less than 40%. Therefore, the total dose delivered to the subject is not only more bioavailable for the sufentanil dosage forms but it is more consistent.

Although this high bioavailability could be due to a number of factors including but not limited to erosion time, it is likely that the lack of saliva produced by the small size of the dosage forms limits the swallowing of the drug and avoids the low bioavailability typical of drug absorption via the GI route. Both Fentora and Actiq package inserts claim at least 50% and 75% of the drug dose, respectively, is swallowed via the saliva, and both exhibit lower bioavailability than the claimed dosage forms.

The dosage forms used in the clinical trials had a volume of approximately 5 microliters (mass of 5.5-5.85 mg), a small fraction of the size of Actiq or Fentora lozenges. Therefore, less than 25% of the drug is swallowed, which is a much lower percentage than is swallowed with Fentora or Actiq.

The sufentanil sublingual dosage forms are also superior in terms of consistent drug plasma levels early after administration. The $C_{max}$ obtained with the 10 mcg sufentanil dosage form was 27.5±7.7 pg/ml. The coefficient of variation of the $C_{max}$ is therefore only 28%. The $C_{max}$ for Fentora and Actiq suffer from variability of GI uptake of drug. Fentora reports a $C_{max}$ of 1.02±0.42 ng/ml, therefore the coefficient of variation of the $C_{max}$ is 41%. The range of coefficients of variation for the various doses of Fentora is from 41% to 56% (package insert). The Actiq coefficient of variation of $C_{max}$ is reported as 33% (Fentora package insert).

In addition to superior bioavailability and consistency in plasma concentrations, the $T_{max}$ for 10 mcg sufentanil dosage forms was 40.8±13.2 minutes (range 19.8-60 minutes). The reported average $T_{max}$ for Fentora is 46.8 with a range of 20-240 minutes. The $T_{max}$ for Actiq is 90.8 minutes, range 35-240 minutes (Fentora package insert). Therefore, the consistency in onset of analgesia for sufentanil dosage forms is markedly better than that of Fentora and Actiq.

In addition, the $T_{max}$ values obtained following repeated sublingual administration of the claimed sufentanil dosage forms were significantly shorter than those observed following administration of a single sublingual sufentanil dosage form. Most notably, the $T_{max}$ obtained with repeat dosing of 10 μg (4×10 μg) sufentanil dosage forms (fast-eroding) occurred 24.6 minutes after the previous (fourth) dose. The coefficient of variation around $T_{max}$ was only 18%, indicating a very consistent and predictable $T_{max}$ with repeated sublingual administration of the claimed sufentanil dosage forms.

The linearity of sufentanil plasma levels following sublingual administration of the claimed sufentanil dosage forms doses was consistent from the 2.5 mcg dose up through the 80 mcg dose.

Although still in development, published data allows comparison of the sufentanil pharmacokinetic data provided herein to that of Rapinyl, a fentanyl sublingual fast-dissolve lozenge. The coefficient of variation around the AUC for all three doses of sufentanil exemplified herein (2, 5, and 10 mcg) averaged 28.6%, demonstrating that the observed low coefficient of variation is not dependent on dose. In contrast, the published bioavailability for a sublingual fentanyl product, Rapinyl, is approximately 70% (Bredenberg, New Concepts in Administration of Drugs in Tablet Form, Acta Universitatis Upsaliensis, Uppsala, 2003). The coefficient of variation of the AUC (0-infinity) for Rapinyl ranges from 25-42% and is dose-dependent.

In addition, the coefficient of variation of the $C_{max}$ for Rapinyl varies from 34-58% depending on dose. As shown by the data presented herein, administration of the 10 mcg sufentanil dosage form resulted in a $C_{max}$ variation of only 28%, and the average coefficient of variation of $C_{max}$ for the 2, 5, and 10 mcg doses was 29.4%, indicating minimal variability depending on dose. Similarly, the coefficient of variation for $T_{max}$ with Rapinyl ranges from 43-54% depending on dose, whereas for our sufentanil dosage forms, this coefficient of variation for $T_{max}$ averages only 29% over all three dosage strengths. This consistent onset of action achieved with sublingual sufentanil dosage forms allows a safer redosing window when compared to any of the three comparator drugs, since rising plasma levels are contained to a shorter period.

Additionally, as with Fentora and Actiq, Rapinyl demonstrates a longer plasma elimination half-life (5.4-6.3 hours, depending on dose) than the claimed sufentanil dosage forms. The plasma elimination half-life of sufentanil dosage forms ranged from 1.5-2 hours following a single oral transmucosal administration in humans (Table 2), which allows for more titratability and avoids overdosing. As will be understood by those of skill in the art, the half-life described herein for the exemplified dosage forms may be adjusted by modification of the component and relative amounts of the excipients in the formulation used to make a given dosage form. The ability to titrate to higher plasma levels by administering repetitive doses of the sublingual sufentanil dosage forms was also tested in this human study.

The methods and systems described herein are designed to work effectively in the unique environment of the oral cavity, providing for higher levels of drug absorption and pain relief than currently available systems. The claimed methods and systems are designed to avoid the high peak plasma levels of intravenous administration by entry into the circulation via the sublingual mucosa.

The claimed methods and systems further provide for independent control of bioadhesion, dosage form disintegration (erosion) and drug release over time, together with administration using a device to provide a safe delivery profile. The device-administered sublingual dosage forms provide individual, repetitive doses that include a defined amount of the active agent (e.g., sufentanil), thereby allowing the patient or care giver to accurately titrate the amount of drug delivered and to adjust the amount as appropriate in a safe and effective manner. The lock-out feature of the dispensing device adds to the safety of the drug delivery profile.

Further, treatment with the claimed compositions, methods and systems provides for improved safety by minimizing the potentially deleterious side effects of the peaks and troughs in the plasma drug pharmacokinetics, which are typical of currently available medications or systems for treatment of pain.

Advantages of the claimed sublingual dosage forms over various liquid forms for either sublingual or intranasal administration include local release of drug from the dosage form over time with minimal swallowing of liquid drug via either the nasal or oral/GI route.

Due to the small size of the oral transmucosal dosage forms, repeated placement in the sublingual cavity over time is possible. Minimal saliva production and minimal physical discomfort occurs due to the small size, which allows for repetitive dosing over days to weeks to months. Given the lipid profile of the sublingual cavity, the sublingual route, also allows for slower release into the plasma for certain drugs, such as sufentanil, which may be due to utilization of a "depot" effect that further stabilizes plasma levels compared to buccal delivery.

The oral transmucosal dosage forms are designed to fit comfortably under the tongue such that the drug form erodes sufficiently slowly to avoid the immediate peak plasma levels followed by significant drop off seen in prior art formulations such as described in U.S. Pat. No. 6,759,059 (Rapinyl), wherein fentanyl was administered via tablets containing 400 mcg of fentanyl which resulted in a peak plasma level of 2.5 ng/ml followed by an immediate drop in plasma level. Fentora (fentanyl buccal tablet) also suffers from a lack of a plateau phase but rather has a steep incline up to the $C_{max}$ followed by a significant drop-off in plasma levels (Fentora package insert).

VII. Utility of Small-Volume Oral Transmucosal Dosage Forms

The claimed dosage forms, methods and systems find utility in delivery of sufentanil via the sublingual route for treatment of pain. The small volume of the sublingual dosage forms provide for high bioavailability, low variability in $T_{max}$, low variability in $C_{max}$ and low variability in AUC. The dosage forms also provide for prolonged plasma levels within the therapeutic window.

More specifically, the claimed dosage forms, methods and systems provide the advantages that:

(a) there is a linear relationship between sufentanil plasma levels in a subject following administration of the claimed sufentanil dosage forms and the amount of sufentanil in the dosage form;

(b) a single sublingual administration of the claimed sufentanil dosage forms to a subject results in an $AUC_{inf}$ with a coefficient of variation of less than 40%;

(c) a single or repeated sublingual administration of the claimed sufentanil dosage forms to a subject results in a $T_{max}$ with a coefficient of variation of less than 40%;

(d) repeated sublingual administration of the claimed sufentanil dosage forms to a subject results in a bioavailability that is greater than the bioavailability following a single sublingual administration to said subject;

(e) the difference between the $T_{max}$ following repeated sublingual administration of the claimed sufentanil dosage forms and the time of the previous sublingual administration is shorter than the $T_{max}$ following a single sublingual administration to the subject;

(f) there is a linear relationship between $C_{max}$ and the amount of sufentanil in the dosage form;

(g) there is a linear relationship between $AUC_{inf}$ and the amount of sufentanil in the dosage form; and (h) the highest predicted steady-state sufentanil concentration following multiple administrations of 10 or 15 mcg sublingual sufentanil dosage forms is predictable allowing for an accurate determination of safe lock-out times and therefore safe and efficacious treatment of pain.

In one exemplary embodiment described in detail herein, the dosage forms find utility in treating a subject suffering from pain that may be associated with any of a variety of identifiable or unidentifiable etiologies. In this embodiment, the dosage forms find utility in suppression or mitigation of pain. The term "treatment" or "management" of pain is used here to generally describe regression, suppression, or mitigation of pain so as to make the subject more comfortable, as determined for example by pain score.

The invention finds utility in the treatment of both opioid naïve patients and opioid tolerant patients.

The dosage forms find particular utility in the treatment of acute pain, such as post-operative pain, as well as other pain, such as "in the field", i.e., under highly sub-optimal conditions.

Paramedics or military medics often are required to treat severe acute pain or other injuries or conditions in non-sterile situations, where needles used for IV or IM administration can result in unintended needle sticks, risk of infection, etc. Oral opioid tablets often take 60 minutes to provide relief which is too long for someone in severe pain. The claimed dosage forms find utility in addressing this need.

When the dosage forms are used for the treatment of pain, the claimed methods and systems find utility in administration of drugs to pediatric and adult populations and in treatment of human and non-human mammals, as well as in opioid tolerant and opioid naïve patient populations.

Application of the claimed methods and systems is not limited to any particular therapeutic indication. As such, the claimed dosage forms find utility in administration of sufentanil to pediatric and adult subjects and in the treatment of human and non-human mammals.

The dosage forms find utility in pediatric applications, since the comfortable and secure nature of the dosage form allows children to readily accept this mode of therapy and will reliably deliver drug transmucosally. Specific examples include, but are not limited to, treatment of pediatric acute pain when IV access is not available or inconvenient, treatment of pediatric asthma when the child is not able to use an inhaled route of administration effectively, treatment of nausea when a child can not or will not swallow a pill, pre-procedural sedation when a child is NPO (no oral intake allowed) or a more rapid onset is required.

The dosage forms find further utility in veterinary applications. Specific examples include, but are not limited to, any treatment of an acute condition for which IV administration is not readily available or inconvenient, such as pain relief, anxiety/stress relief, pre-procedural sedation, etc.

VIII. Dispensing Devices

Dispensing devices and systems for oral transmucosal administration of small volume drug dosage forms are provided. The dispensing devices are handheld and portable and comprise a housing having a dispensing end which typically has a proboscis with a shroud that provide a means for blocking or retarding saliva ingress and/or moisture control. The dispensing devices further provide safety features such as a means for lock-out and a means for patient identification.

The claimed dispensing devices, methods and systems comprise delivery of small volume dosage forms to the oral mucosa. The invention is not limited to the specific devices, systems, methodology and dosage forms detailed herein, as these may, of course, vary. It is also to be understood that the terminology used herein is for the purpose of describing particular embodiments only, and is not intended to limit the scope of the present invention.

Blocking/Retarding Saliva and Moisture Ingress

The claimed dispensing devices comprise a means for minimizing or eliminating saliva ingress and moisture ingress into the dispensing device: (1) to avoid wetting the dosage forms therein; (2) to isolate any saliva that enters the dispensing device in such a manner that the dosage forms therein remain dry; (3) to absorb or adsorb any saliva that enters the dispensing device in such a manner that the dosage forms remain dry; (4) to block saliva and moisture from entering the device to protect the dosage forms from vapor and liquid phase moisture, or (5) any combination thereof.

The dispensing device has a means for preventing and/or controlling humidity ingress due to ambient conditions outside of the device.

The means for minimizing or eliminating saliva ingress or preventing other moisture from entering the dispensing device includes, but is not limited to, one or more flexible or rigid seals, one or more flexible or rigid wipers, use of one or more absorbent material components such as a desiccant or pad, a door or latch that is manually or automatically opened and closed, multiple stage delivery systems, a positive air pressure and airflow, or an air gap or prescribed distance or barrier/shroud maintained between the dosage form delivery orifice and the mucous membrane tissues within the mouth that may transport the saliva. The shroud limits the ability of the tongue or sublingual mucosa to contact the dosage form dispensing area, thereby controlling saliva contact and ingress. By inhibiting or eliminating the "wetness" inside the shroud and on the surface of the valve/seal, the dosage form is dispensed without adhesion occurring between the dosage form and the shroud or valve/seal.

To protect the drug dosage forms from exposure to moisture either from humidity, saliva ingress, or accidental exposure to other water based liquids, the dispensing device and the container or cartridge which houses the dosage forms within the device contains a desiccant.

Means for trapping or otherwise isolating saliva or moisture if it enters the device include, but are not limited to, a hydrophilic wicking material or component, an absorbent or adsorbent material or component, a desiccant material or component, a separate track or channel for moisture to collect, a separate channel to communicate moisture to the absorbents or adsorbents, or any combination of these materials or components.

A desiccant is a sorbant, in the form of a solid, liquid, or gel that has an affinity for water, and absorbs or adsorbs moisture from it's surrounding, thus controlling the moisture in the immediate environment. Any commercial desiccant may be used. Commercial desiccants typically take the form of pellets, canisters, packets, capsules, powders, solid materials, papers, boards, tablets, adhesive patches, and films, and can be formed for specific applications, including injection moldable plastics. There are many types of solid desiccants, including silica gel (sodium silicate, which is a solid, not a gel), alumino-silicate, activated alumina, zeolite, molecular sieves, montmorillonite clay, calcium oxide and calcium sulfate, or others, any of which may be used in the claimed dispensing devices. Different desiccants have different affinities to moisture or other substances, as well as different capacities, and rates of absorption or adsorption. Also, different types of desiccants will come to equilibrium at different relative humidities in their immediate surroundings. As a means for protecting the dosage forms and the internal portions of the dispensing device from moisture, one or more desiccants may be employed at the proboscis; in or adjacent to the dosage form; in or adjacent the delivery pathway; in or adjacent the dosage form, tablet magazine or cartridge; in or adjacent to other components of the dispensing device; formed as an injection molded component of the dispensing device; a compressed desiccant that is pressed into location; or desiccant in any other location within or without the device.

In one preferred embodiment, the desiccant snaps into a cavity in the side of the cartridge. There are holes in the desiccant cavity that connect it to the dosage form stack, exposing the dosage forms to desiccant and keeping them dry.

The claimed dispensing devices rely on valves, pads, seals, the rest position of the push rod, proboscis design and a shroud to minimize or eliminate saliva ingress or moisture into the dispensing device during administration of the dosage form.

Valves for use in the claimed devices are typically dome/trocar type valves that provide enough sealing force to keep saliva and/or moisture from entering the device and serve to minimize or eliminate saliva ingress or moisture by closing the distal orifice during dispensing and after a dosage form has been dispensed.

Pads for use in the claimed devices have various geometries that aid in contacting or communicating with the push-rod in order to removed liquid from the push rod surface. Such pads typically contain hydrophilic properties and serve to minimize or eliminate saliva ingress or moisture ingress by transporting the liquid away from the track and push rod.

Seals and wipers for use in the claimed devices are designed to maintain a uniform seal around a drug dosage form and a pushrod during delivery and are characterized by flexible materials that impart a seal around the dosage form and pushrod and serve to minimize or eliminate saliva ingress or moisture by sealing and wiping the orifice and pushrod before, during, and after dispensing.

The rest position of the push rod in the claimed devices is characterized by positioning the pushrod in an intermediate location distal to the cartridge exit, and proximal to the distal dispensing orifice and serves to minimize or eliminate saliva ingress and moisture by allowing the pushrod to reside in a location that contains a desiccant, absorbents, or channel that dries the pushrod while at rest between dosage dispenses.

The proboscis design for use in the claimed devices is characterized by a distal device shape, typically an S-shape, that aids in use of the device and/or placement of the tip on the oral mucosa of the subject. The shape typically has curves, angles, and geometries such that it enables proper use of the device and placement of the dosage form on the oral mucosa of the subject, e.g., in the sublingual space.

The shroud of the claimed devices has a geometry that forms a barrier between the device and the oral mucosa and tongue, a relief for dosage form delivery, and an interior that is hydrophobic or hydrophilic and serves to minimize or eliminate saliva ingress or moisture ingress by creating a barrier from the oral mucosa contacting the valve area and dosage form, aiding in dosage form dispensing and discouraging dosage form adherence to the shroud. The shroud may have a rounded interior surface or other geometries to mitigate the dosage form adhering to the shroud. The shroud limits the ability of the tongue or sublingual mucosa to contact the dosage form dispensing area, thereby controlling saliva contact and ingress.

FIGS. 11A-E provide schematic depictions of a variety of aspects of one embodiment of a drug dispensing device constructed to hold a plurality of dosage forms for oral transmucosal delivery. FIG. 11A is a schematic depiction of a fully assembled or single piece dispensing device 11 of the invention. In FIG. 11B, the dispensing device 11 includes a reusable head 13 and a disposable body 15; in FIG. 11C the dispensing device 11 further includes a cartridge 17 in FIG. 11D the dispensing device 11 includes a valve 33, a proboscis 31, a latch button 19, a power train coupling 25, a hub lock 21 and a dispense button 23; and FIG. 11E is a schematic depiction of a reassembled and complete dispensing device 11.

Figure 12:
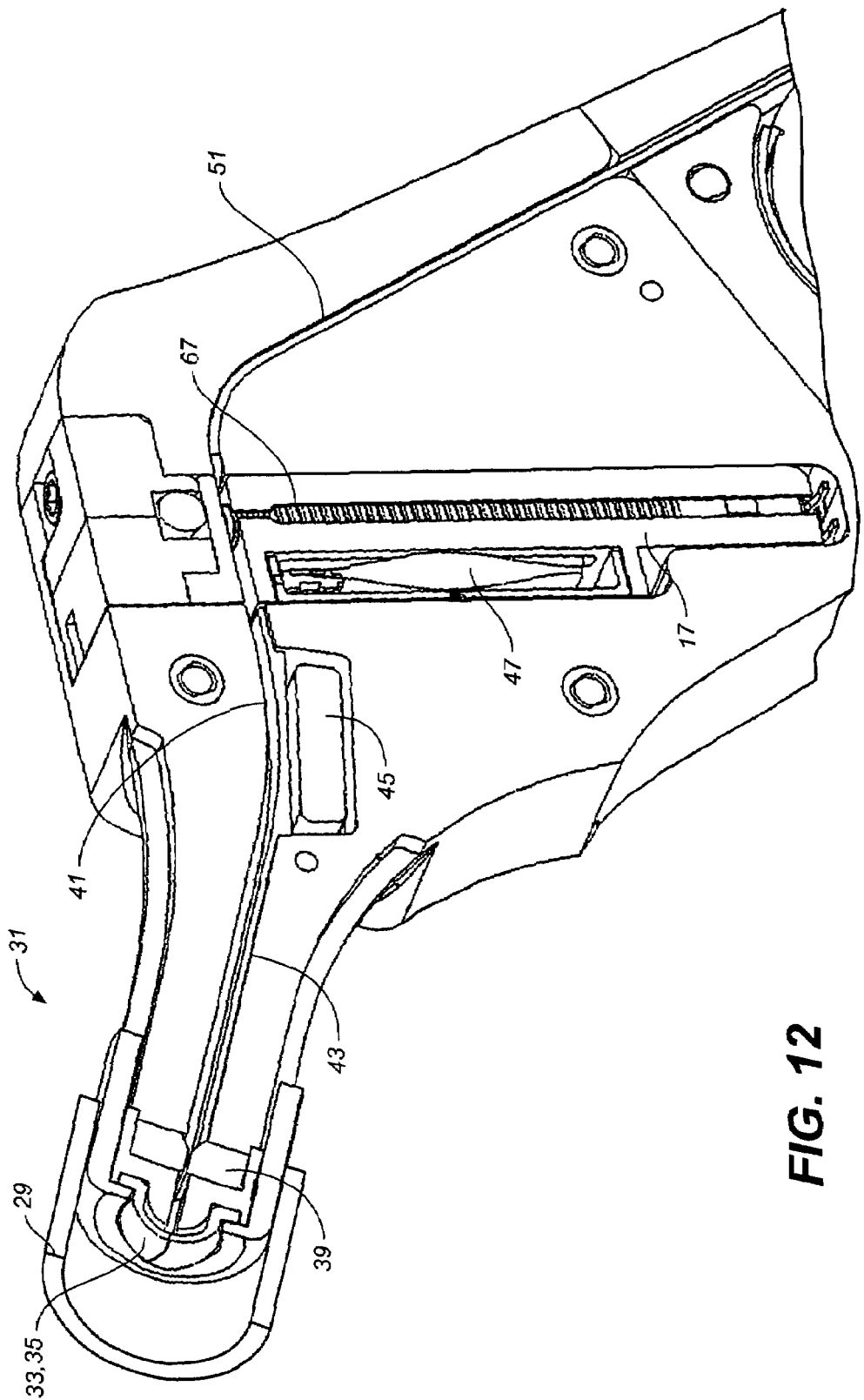
FIG. 12 is a schematic depiction of an exemplary dispensing device showing features designed to block or retard saliva and moisture ingress. The preferred embodiment includes a dispensing tip having a shroud 29, having one or more of: a wiping seal/valve 33, 35, an absorbent pad 39, a pushrod 51, a drying chamber/moisture communication channel 43, desiccant in the channel 45, a cartridge 17 containing dosage forms 67 and desiccant in the cartridge 47.

FIG. 12 provides a schematic depiction of an exemplary dispensing device wherein the dispensing tip comprises a shroud 29 having a one or more of: a wiping/sealing valve 37, an absorbent pad 39, a drug drying chamber/moisture communication channel 43, desiccant in the channel 45, a cartridge 17 containing dosage forms 67 and desiccant in the cartridge 47.

Figure 13A:
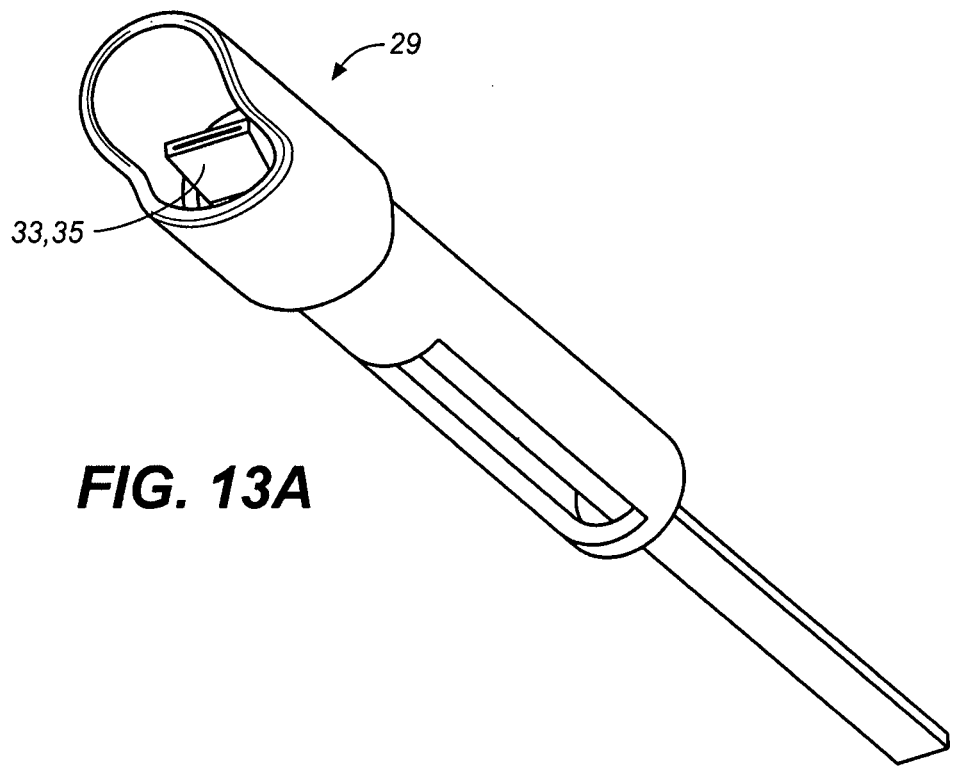
FIGS. 13A and 13B are schematic depictions of an exemplary geometry for a dispensing tip.
Figure 13B:
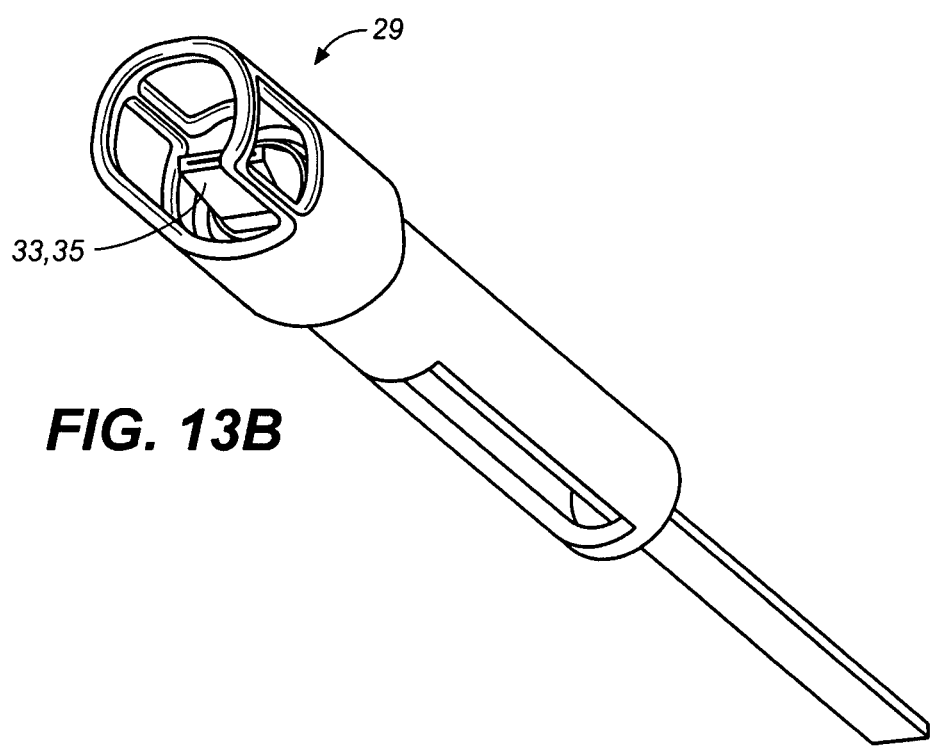
Figure 14A:
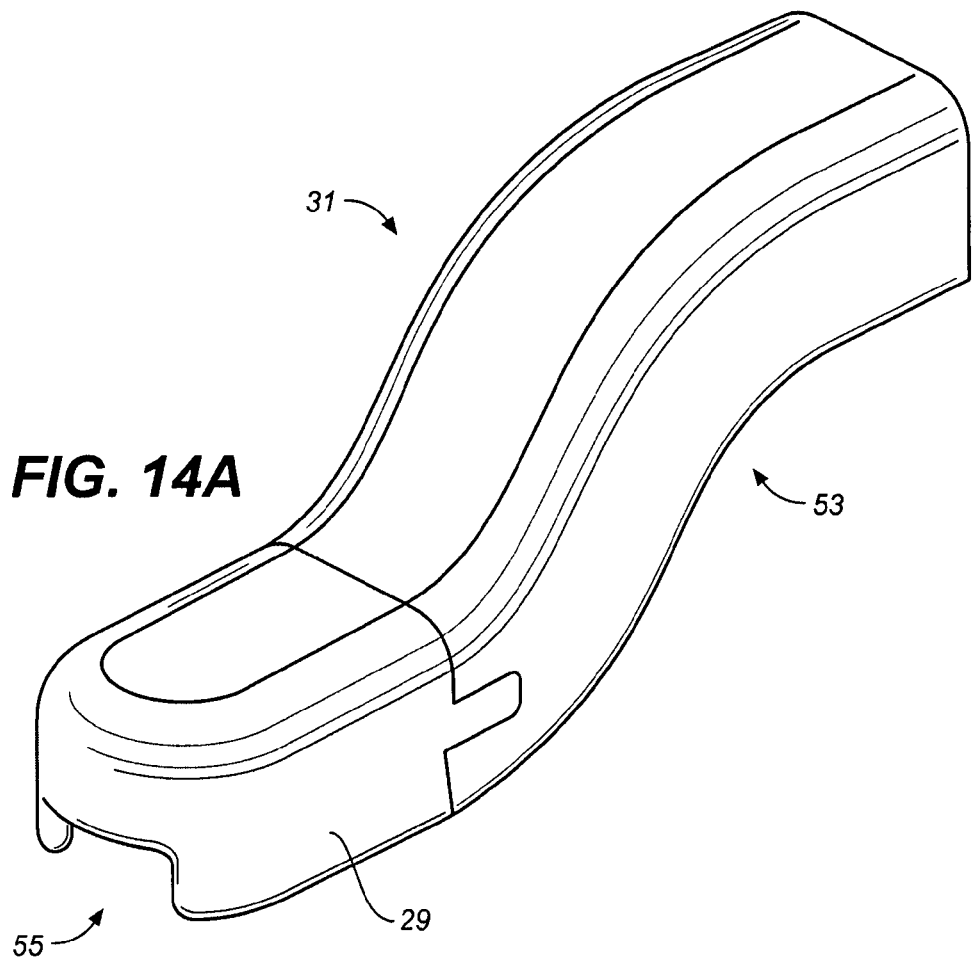
FIGS. 14A-D are a schematic depiction of an exemplary proboscis 31 of a dispensing device 11 wherein the proboscis 31 has an S-shape 53 and comprises a shroud 29 and a valve. The shroud shields the valve from moisture and saliva ingress from the tongue and other mucosa and provides an area for the dosage form to exit the device without "sticking" to the wetted distal valve or shroud area. The shroud also comprises a cut-out/relief 55 in order to mitigate the dragging of dosage forms when the device is removed from the oral space. The valve functions with the shroud to control saliva and moisture ingress, as well as aid in delivery of the dosage form.
Figure 14B:
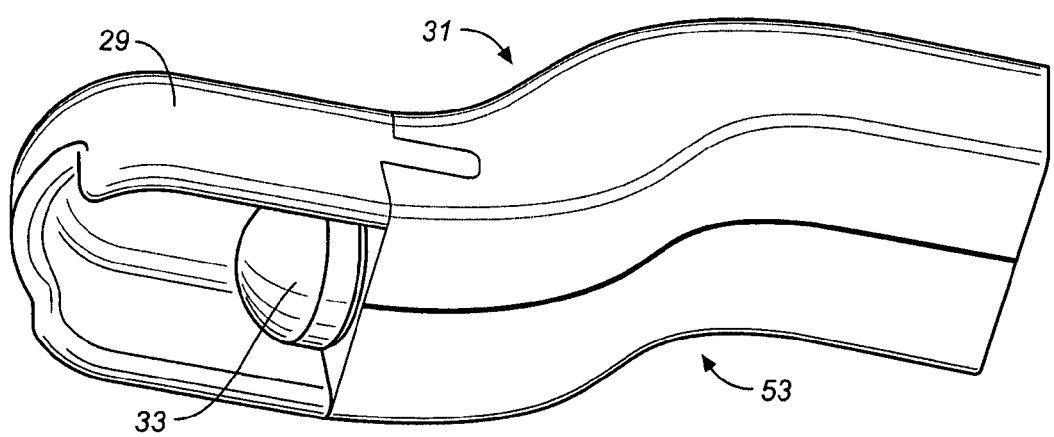
Figure 14C:
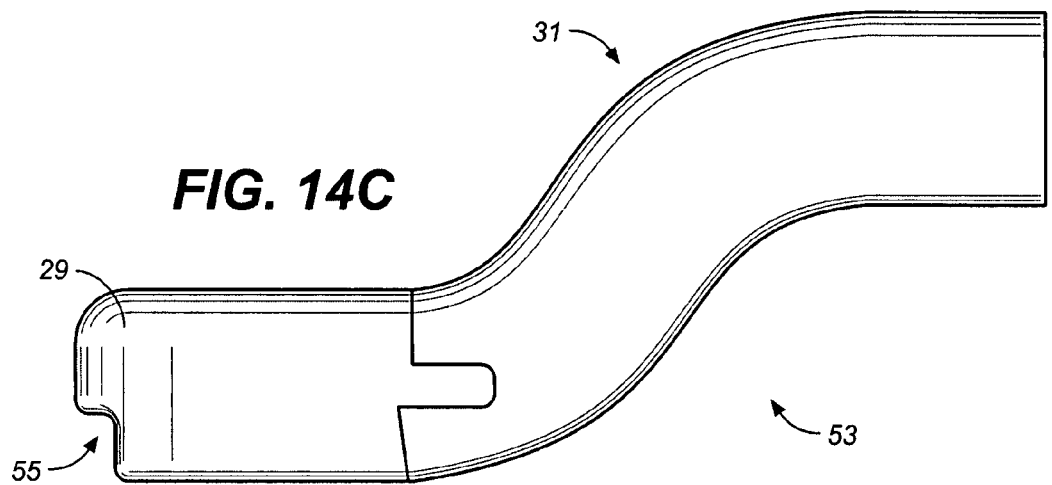
Figure 14D:
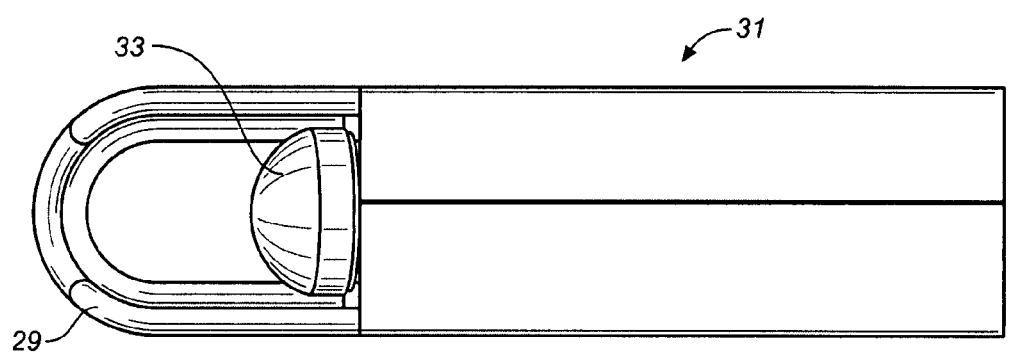

FIGS. 13A and 13B are schematic depictions of an exemplary geometry for the dispensing tip that prevents contact of one or more seals 33, 35 with the moist or wet surface of the oral mucosa via a shroud 29.

FIGS. 14A-D are a schematic depiction of an exemplary proboscis 31 of a dispensing device 11 wherein the proboscis 31 comprises a shroud 29, a valve 33 for dispensing a dosage form 67 and a cut-out/relief 55 for the dosage form 67 to be placed against the oral mucosa and not moved when the device 11 is withdrawn following dispensing.

A means for minimizing saliva ingress and moisture into the claimed devices is important for preservation of the integrity of dosage forms during storage, e.g., prior to an between oral transmucosal administrations.

The claimed dispensing devices may be used to administer a drug dosage form that is sensitive to moisture and/or humidity. In such cases, a drug dosage form cartridge serves to protect the drug dosage form from liquid and vapor phase moisture, including humidity, liquid moisture, saliva, mucus, etc. The cartridge may be cylindrical, disk-shaped, helical, rectilinear, non-ordered, or may take the form of any assemblage of drug dosage forms that allows the drug dispensing device to dispense them in a controlled manner. To prevent the unused drug dosage forms from absorbing moisture or otherwise becoming exposed to moisture prior to use, the cartridge may provide a means of sealing the drug dosage forms from exposure to moisture. This may accomplished by use of a cartridge that contains individually packaged drug dosage forms separated by a thin impermeable foil or impermeable material such that when one drug dosage form is dispensed from the cartridge, the seal protecting the remaining dosage forms remains unbroken. Alternatively, the dosage forms may be packaged in such a manner within the cartridge that two or more dosage forms are packaged together in each separate sealed compartment. In some embodiments, all of the dosage forms in a cartridge may be packaged together in a foil sealed compartment.

A drug cartridge that houses small volume drug dosage forms within the dispensing device may afford a seal against moisture by means of a septum, an elastomeric seal or valve, a sliding, translating, hinged door or valve, or by means of sealing against another component of the drug dispensing device when loaded. In this manner, a single re-sealable seal may be opened either independently or by means of the passage of a dosage out of the cartridge. Once the dosage form is delivered from the cartridge, the re-sealable seal on the cartridge may be re-sealed to prevent moisture or other contaminants from damaging the remaining drug dosage forms within the cartridge. The cartridge may further have a non-re-sealable seal that is broken when it is loaded into the drug dispensing device or upon delivery of the first dosage form from the cartridge.

In other embodiments, the cartridge contains a desiccant or other absorbent or adsorbent material to absorb or adsorb moisture that penetrates the cartridge either prior to use or during normal use. A cartridge for use in a claimed dispensing device may contain any combination of individually sealed dosage forms, multiply sealed dosage forms, re-sealable seals, non-re-sealable seals, desiccants, absorbents, or adsorbents. In one embodiment, a cartridge for use in the dispensing device in holds sufficient drug dosage forms for 1-5 days of treatment, e.g. 40 dosage forms or sufficient drug dosage forms to provide 48 to 72 hours of treatment.

Pushrod Design

Figures 15A, 15B:
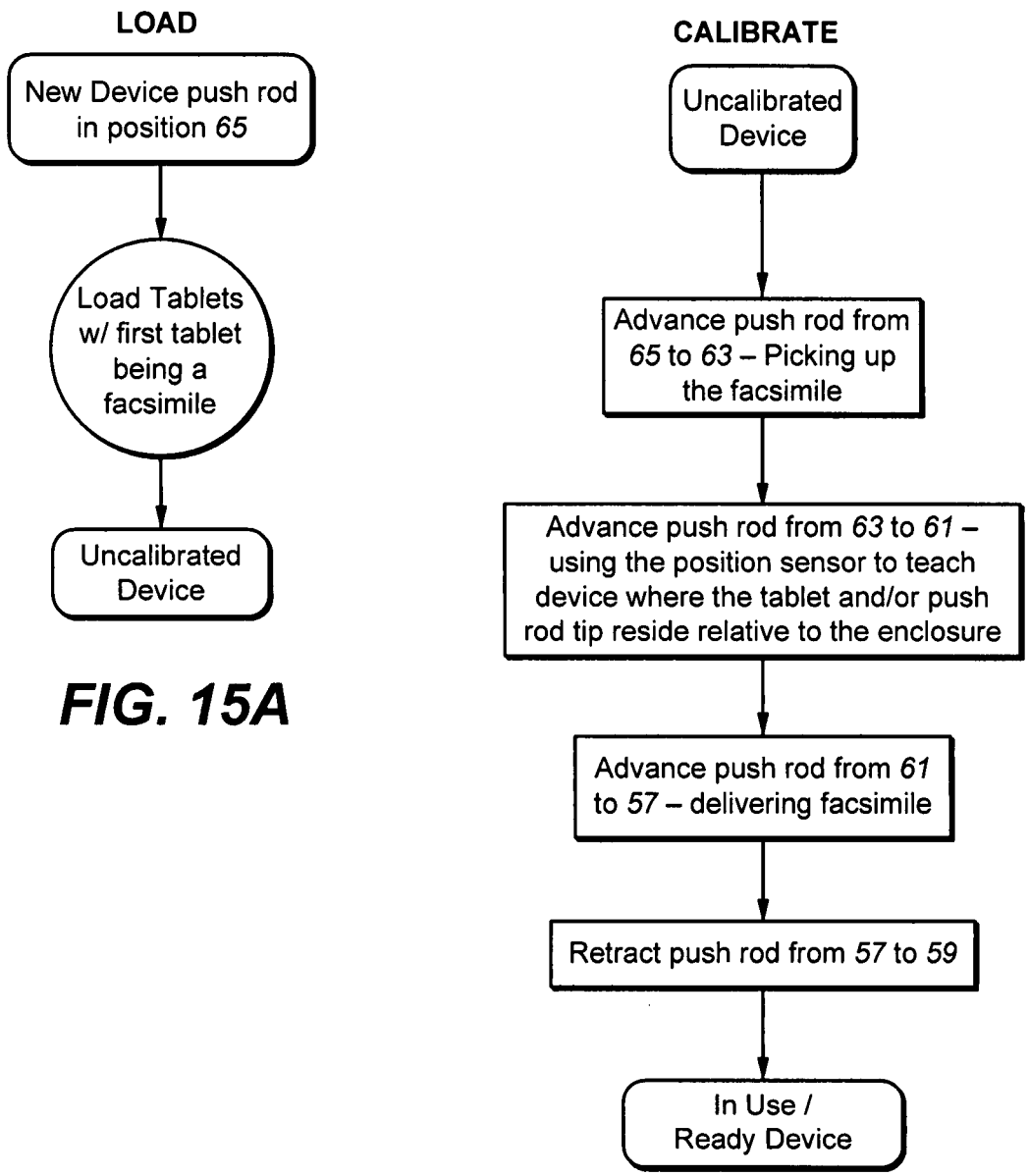

FIGS. 15A-D provide a series of flow diagrams for use of an exemplary dispensing device showing pusher logic, wherein FIG. 15A shows the LOAD feature; FIG. 15B shows the device calibration logic flow. Referring to FIG. 16, the pushrod 51 is advanced from position 65, picks up the shipping tablet 69 at position 63, and is further advanced to position 61. At position 61, the device senses the presence of the shipping tablet 69 and/or push rod 51. In doing so, the device is calibrated and knows the location of the shipping tablet 69 and/or end of the push rod 51 regardless of assembly tolerances, variations in push rod length and push rod end conditions. Following this calibration, the push rod 51 advances the shipping tablet 69 from position 61 to position 57 where the shipping tablet 69 is dispensed from the device. During this operation, the device is able to distinguish between a shipping tablet 69, a push rod 51, and a drug dosage form 67. This differentiation enables the device to confirm that a cartridge is unused because a shipping tablets is the first thing dispensed from a new cartridge during device setup. The feature that provides the means for differentiating between the shipping tablet, push rod, and dosage form 67 may be optical, physical, RF, electronic (resistive, capacitive, or other) or magnetic. The push rod 51 advance from position 65 and position 57 described above, could be continuous or intermittent and a physical stop at position 61 is not required. The push rod 51 then retracts from position 57 to position 59, placing the device 11 in the ready position with the push rod 51 under the remaining dosage forms 67. In this position, the push rod 51 keeps dosage forms 67 from inadvertently falling out of the device 11.

Figures 15C, 15D:
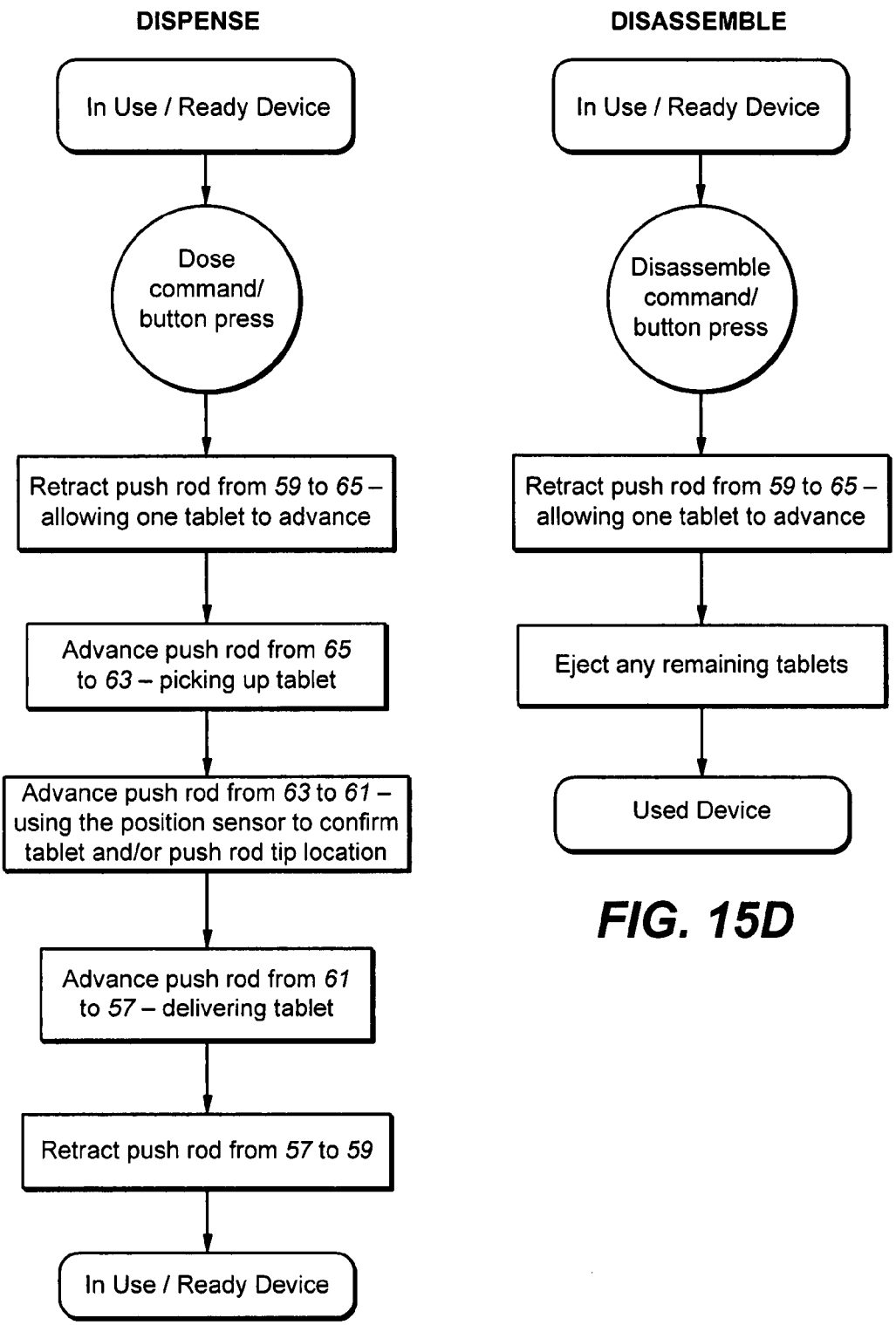

FIG. 15C shows the device dispense logic flow. referencing FIG. 16, following a dose command, the push rod 51 retracts from position 59 to position 65, allowing the dosage forms 67 to advance into the push rod track. The push rod 51 then advances from position 65, picks up a dosage form at position 63, and then dispenses the dosage forms 67 from the device at position 57. Between positions 63 and 57, the presence of a dosage form 67 is sensed/confirmed at position 61 by the position sensor. The push rod then retracts from position 57 to position 59, placing it in the ready position with the push rod 51 is under the remaining dosage forms 67. In this position, the push rod 51 is allowed to dry before the next dosage form 67 dispense, as well as keeps dosage forms 67 from inadvertently falling out of the device 11.

FIG. 15D shows the device disassemble logic flow. Following a "disassemble" command, the push rod 51 is moved to position 65. This allows for the removal of any remaining dosage forms 67 without push rod interference.

FIG. 16 is a schematic depiction of an exemplary dispensing device showing the stages of push rod/dosage form interaction during device use. In FIG. 16, the push rod 51, dosage forms 67, shipping tablet 69, spring 73 and position sensor 71 are shown. During use, the push rod 51 moves between positions 57, 59, 61, 63 and 65, also shown in FIG. 16 and further detailed in FIGS. 15A-D.

Dosing History/Feedback

Further embodiments of the device include the ability to store historical use information and the ability to transmit such information. The device may be capable of unidirectional (downloading) or bidirectional information transfer. For example, an exchange of information may be accomplished by downloading stored information to a computer through a physically wired interface, such as a USB or any other communication connection. Alternatively, information may be communicated via a wireless system.

In another embodiment, the dispensing device has a dose counting feature that monitors and stores the history of drug usage. Such information may include historical use information, for example the number of dosages stored and dispensed, and the times of dispensing.

Calibration

The dispensing device may be capable of self-calibration of the dispense mechanism, or the device may be calibrated manually. This process may employ a shipping tablet with a feature or features that physically differentiate it from a drug dosage form or the push rod. These features may be designed so that device calibration precision is higher that that attainable using a dosage form or push rod. The differentiating feature may be physical, optical, radio frequency (RF), electronic or magnetic.

Patient Identification Feature

In one aspect, the dispensing device comprises a detecting means for patient identification such as a fingerprint reader, an optical retinal reader, a voice recognition system, a face recognition system, a dental imprint recognition system, a visual recognition system, or a DNA reader. The dispensing device may employ one or more means to identify the user, enabling the system to determine if a dispensing request is being made in an authorized or unauthorized manner. It is important for effective delivery of many potential drugs and drug dosage forms to ensure that the dispensing device is not accidentally or intentionally used by an unauthorized individual to prevent accidental or intentional diversion of the drug. Such patient identification systems may recognize one or more users, for example, in an inpatient hospital setting the dispensing device could be programmed to recognize the patient to whom it is prescribed, as well as authorized healthcare providers such as nurses and physicians. In an outpatient home setting, for example, the dispensing device may only respond to the patient to whom it is prescribed.

The dispensing device may employ any means of user identification, including fingerprint identification, RFID detection with the use of an active or passive RFID tag on bracelet, necklace, clip, belt, strap, adhesive patch, implant, or means of locating and affixing a tag, retina identification, DNA identification, voice recognition, password or code entry, physical key, electronic or magnetic key, personal area network identification using the human body or clothing as a data or signal conduit, optical scanner or face recognition, sonic, subsonic or ultrasonic identification, or any other means of identifying an individual and verifying their identity.

One method of patient identification is the use of a short distance ("near field") passive RFID tag attached to a bracelet, necklace, adhesive patch, clothing tag, orally mounted device, like an orthodontic retainer, belt, strap, some combination of these, or another location. When an RFID tag is used in the "near field", roughly defined as about 16% of the wavelength of the received signal, the tag behaves in the inductive mode of operation, coupling between the reader and tag antenna magnetically. The near field is characterized by at least two features: first is a rapid decline in field strength with distance, and second is a strong directionality of the signal. In the near field, the signal strength falls off very rapidly, with a signal strength loss of approximately 60 dB per decade in distance. For good inductive coupling between the transmitter antenna and the RFID tag antenna, the two antennas are oriented in parallel planes with the axes through the center of each antenna in close proximity. Strong signal strength (robust patient identification) is provided when the device is very close to the RFID tag. At the same time, a very poor signal is provided when the device is further away from the tag, which helps prevent unauthorized use by someone other than the patient who attempts to use the device. It is preferable to operate in this near field region with good antenna alignment. Furthermore, it is preferable to operate with a very short distance of adequate signal strength for a positive identification, so that it is very difficult to receive a signal if the device is not in the proper orientation and proximity to the RFID tag. To attain a short distance and a proper alignment between antennas, the dispensing device may be designed so as to properly locate the RFID reader antenna, mounted in the dispensing device, adjacent to an RFID tag antenna, mounted, for example, on a wrist band or bracelet, or a clothing tag on the collar, or an adhesive patch on the hand, arm, cheek, neck, or elsewhere. Furthermore, an RFID tag antenna on a wrist band or bracelet may be held in proper alignment and location by means of a small adhesive patch that prevents the bracelet from moving or rotation on the wrist.

In another embodiment, the dispensing device employs a high frequency RFID reader for use in the inpatient (hospital, clinic, etc.) setting, operating on or near the 13.56 MHz frequency band, and the patient is be fitted with a matching RFID tag and antenna on a disposable bracelet or wrist band, designed in such a way that if the bracelet or wrist band is removed the RFID tag, the antenna, or another component of the associated circuit will be damaged or destroyed, rendering the bracelet or wrist band non-functional. In one example, the range of the RFID communication is short, between 0 inches and 10 inches preferably, more preferably between 0 and 5 inches, and most preferably between 0 and 3 inches, and may additionally be directional, allowing proper use by the intended patient to be easy and reliable, while at the same time making unauthorized use by another individual difficult, very difficult, or impossible.

Lock Out

The dispensing device provides for lock out, requiring the patient to communicate with the physician or other authorized care giver to unlock the device for the next fixed period.

In this way the device and dock provide for safe drug administration due to greater physician oversight and care management.

The dispensing device provides a means for adjusting both the initial dose and subsequent doses, as well as the lock-out time. The initial dose and lock out time may subsequently be adjusted dependent upon patient response, duration of treatment and the like.

The initial timed lock-out period for a claimed dispensing device is typically from about 1 minute to about 60 minutes, from 3 minutes to 40 minutes or from 5 minutes to 30 minutes, and in particular cases is set at any one minute interval from 1 to 60 minutes, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes.

In some cases, a dispensing device has a fixed lockout between doses and may exhibit a shutdown after a fixed period of time. In other cases, the lock-out time is a programmable lock-out time. The lock-out time may also be a fixed time lock-out interval, a predetermined lock-out interval, a predetermined variable lock-out interval, a lock-out interval determined by an algorithm or a variable lock-out interval communicated to the device from a remote computer or docking station.

Additional Features

A dispensing device may provide the ability to recognize a specific cartridge by a mechanical, optical (e.g. bar code), electronic (e.g. microchip), magnetic, radio frequency, chemical, or other means of detecting and identifying the cartridge. In one exemplary embodiment, the drug-containing cartridge contains a physical keying detail on the cartridge that is physically detected by a sensor or switch or a series of sensors or switches in the dispensing device. Furthermore, the dispensing device may communicate unidirectionally or bidirectionally with the cartridge to exchange information. Such information may include drug name, dosage strength, usage information, lockout period, manufacturing lot number, indications for use, side effects, drug interactions, date of manufacture, date of expiration, serial number, number of doses in the cartridge, or any other relevant information. The dispensing device may be able to write, in addition to read, information to the cartridge, like date used, nurse or patient identification, number of doses used, etc.

The dispensing device may provide mechanical protection for the dosage forms contained therein, preventing breakage, chipping, hydration etc., thereby allowing for dispensing of the undamaged dosage forms contained therein. This is of particular importance for small fragile and friable dosage forms.

The drug dispensing device may be powered by a battery, capacitor, fuel cell, or other power supply source, or may require no electrical power, but be manually activated.

In some embodiments, the dispensing device is capable of issuing alarms or other notifications when functional or safety issues arise. The alarm or other notification may trigger an alert on the dispensing device, on a dock or other peripheral device; on a computer or by means of a wired or wireless network, or may alert other remote devices. The alarm or notification may be audible, tactile, visual, or may employ other means of notifying one or more individuals.

Docking Station

In certain embodiments, the device includes a portable or fixed docking station that may query the device, reset it between dosing, lock it when not properly accessed, and control the dosing regimen. The drug dispensing device may communicate with a physician or care giver, via the dock, or by a wired or wireless communication means.

The dispensing device may employ one or more levels of interface for different types of authorized users, for example the patient, the nurse, the physician, pharmacist or other authorized medical or healthcare personnel. These different interfaces may include components such as keypads, buttons, graphical icons and instructions, lights, LED's, monochrome or color graphical or text displays, touch-screens, LCD's, sounds, tactile feedback, voice recognition interfaces, and other input and output devices and means. The activity, or mode, of the user interface may be determined by the mode of operation of the dispensing device, by a login or access activity by a user such as a password or code entry, by the connection or disconnection of the dispensing device from a dock, computer, or network, or by the detection of an authorized access key, such as a key, and/or RFID tag, or similar combination. Upon changing the interface mode, the functionality of the device may be changed, either activating, inactivating or changing the functionality of the various interface components described above. By allowing the device to have one or more interface modes, with differing functionality associated with each one, the device can be optimized for various uses.

Base Station

In some embodiments the drug dispensing system includes a base station for recharging the drug dispensing device and the portable docking FOB between uses. This base station allows for recharging the batteries or fuel cells in multiple dispensing devices and/or FOBs simultaneously. In addition to recharging the drug dispensing devices and FOBs, the base station may provide one or more of the following functionality: wireless or wired connectivity to a peripheral device, computer or network; feedback on the charging state for the devices being recharges; an interface for viewing, adding, deleting, or modifying the data on a drug dispensing device or FOB; a means for synchronizing data between multiple drug dispensing devices and/or FOBs; and a means for conducting a diagnostic test on drug dispensing devices and/or FOBs.

IX. Methods and Systems for Delivering Small Volume Sufentanil Dosage Forms Using a Device Methods and systems for delivering small volume sufentanil-containing dosage forms using a device are provided. FIG. 17 provides a schematic architecture connection diagram illustrating the various components that may be included in a dispensing device or system for dispensing small volume drug dosage forms, including a device with a separate head 13, body 15 and cartridge 17, a portable docking FOB 113, Patient RFID 115 and a base station 117.

Figure 18A:
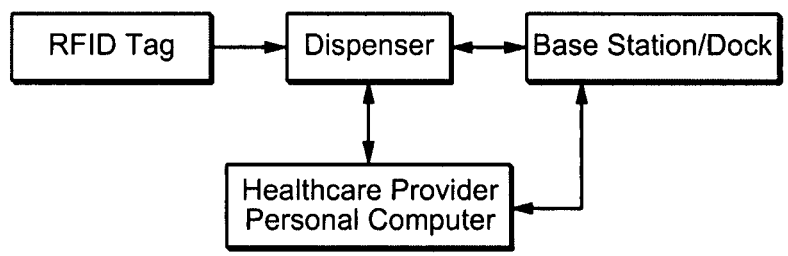
FIG. 18A is a block diagram illustrating one aspect of communication in the drug dispensing system, including an RFID tag, a drug dispensing device, a base station/dock and a healthcare provider personal computer.

A block diagram illustrating one aspect of communication in a drug dispensing system, including an RFID tag, a drug dispensing device, a base station/dock and a healthcare provider personal computer system wherein a drug dispensing device can communicate with the physician or care giver, via the dock, or by means of a wired or wireless communication method is provided in FIG. 18A.

Figure 18B:
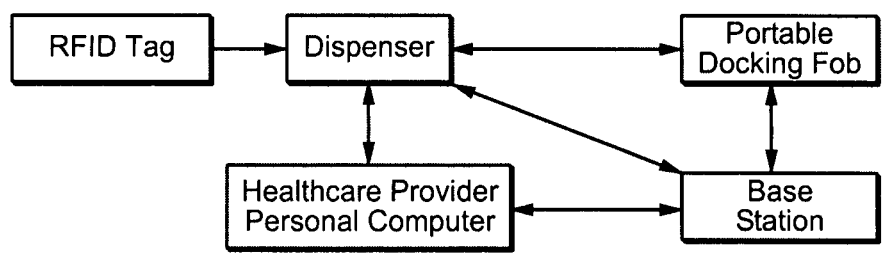
FIG. 18B is a block diagram illustrating another aspect of communication in a drug dispensing system, including an RFID tag, a drug dispensing device, a portable docking FOB, a base station and a healthcare provider personal computer.

A block diagram illustrating another aspect of communication in a drug dispensing system, including an RFID tag, a drug dispensing device, a portable docking FOB, a base station and a healthcare provider personal computer is provided in FIG. 18B. The drug dispensing device may communicate with the physician or care giver, via the FOB, by means of a wired or wireless communication method to provide usage information and information regarding the respiratory status or blood pressure of the patient to the physician at regular intervals. The FOB can be adapted to attach to a cord so as to allow the FOB to hang from the neck of the physician or caregiver.

Exemplary features of the dispensing device include the following:

In one embodiment, the head, body, and cartridge comprise the handheld portion of the device. This device assembly has a latch to disconnect the head and body, and a dispense button for patient use. The device also has lights to show lock-out status, errors, and power. In this embodiment, the cartridge which contains the drug dosage forms and the body are used a single time only.

The system may comprise a portable dock which is handheld, independent of the patient device and solely for healthcare professional use. The dock enables higher level feature use such as deeper queries into patient device use, the ability to upload device data, unlocking of the head/body and the tether, lockout override for dosing the patient, and a larger reading display. The dock is also used to setup and take down the patient device.

The system may also comprise an RFID bracelet that is activated via the dock and is worn by the patient to establish and control dosing to correct patient and to that patient alone. This feature prohibits use of the device by others.

The system may further comprise a recharging base used to charge the dock and heads and is also used to update the heads and docks when new software becomes available or when new users are programmed into the system.

The drug dosage forms are typically provided in disposable cartridges which are loaded into the device prior to administration.

Exemplary set-up instructions for the device include the following steps:

The device head and dock are charged on the recharging station.

The device body and wristband are removed from the packaging.

The device head and dock are removed from the charging station.

The cartridge is loaded into the body by inserting a cartridge into the device body as indicated ensuring that the cartridge "clicks' and is locked in place.

The device body (with cartridge) is assembled onto the head.

The power button on the assembled device is pushed to power-up the system.

The power button on the dock is pushed to power-up the dock.

The assembled device is plugged into the dock.

A healthcare professional scans their fingerprint or inputs a unique password in order to unlock the dock.

The device reads the label on the cartridge and the dock displays setup information, for example, the drug name, the quantity of tablets, the drug concentration, the preset lockout time, the duration of use (72 hours), and the battery status of the head.

After the information is read from the cartridge and displayed on the dock, the healthcare professional will be requested to confirm that all information is correct and will require a witness to verify the information.

The dock will require that the patient wristband be paired to the device by bringing the wristband close to the device.

The device will read the band and request confirmation of the band number; selection and confirmation of the number The patient ID is entered into the dock. i.e. patient medical record number The wristband is placed on the patient's hand that will be used to operate device.

Then, the dock will indicate that it is ready to dispense a plastic initialization tablet or "shipping tablet".

Upon confirmation, the device will dispense a plastic initialization tablet or "shipping tablet". This step is used by the device to calibrate the dispensing mechanism, initiate the cartridge for use, and allows the healthcare professional to verify proper use and to train the patient with a "shipping" or placebo-type tablet.

Once the plastic initialization tablet or "shipping tablet" is dispensed, the dock will require the healthcare professional to confirm that the plastic tablet was dispensed.

After confirmation, the display will indicate that the device is ready for use.

In some cases, a tether can be connected to the device via the dock. The dock will allow the healthcare professional to lock and unlock the tether as required.

If a patient will self administer a drug dosage form using the device, the patient will be trained prior to use.

Exemplary use of the claimed devices and systems is provided in Examples 6-8.

The following examples are provided to illustrate the invention and are not intended to limit any aspect of the invention as set forth above or in the claims below.

EXAMPLES

The following examples are provided to illustrate the invention and are not intended to limit any aspect of the invention as set forth above or in the claims below.

Two different sublingual sufentanil formulations were evaluated including a slower-eroding form (erosion time of approximately 15-25 minutes; Examples 1A and 1B), and a faster-eroding form (approximate erosion time of 6-12 minutes; Examples 2A and 2B). Patients were blocked with a mu-opioid receptor antagonist, naltrexone (50 mg orally twice per day).

Sufentanil plasma concentrations with respect to time were analyzed and tabulated. The maximum sufentanil concentration in plasma ($C_{max}$), time to $C_{max}$ ($T_{max}$) and terminal $t_{1/2}$ were summarized for each dose group. After the final dosing of the repeat-dose studies, the sufentanil $t_{1/2}$ was determined. Comparisons were made between the area under the curve (AUC) for each single administration of sublingual sufentanil dose vs. IV. $C_{max}$, $T_{max}$ and $t_{1/2}$ data were compared for each sublingual sufentanil dosage vs. IV and sublingual administration of sufentanil liquid.

Example 1

Evaluation of the Bioavailability and Pharmacokinetics Following Sublingual Administration of a Small Volume Sufentanil Dosage Form Example 1A All subjects received a 10-minute IV infusion of 5 mcg sufentanil. After a 1-day washout period, each subject then received a single sublingual administration of a dosage form (comprising a slow-eroding formulation) containing 2.5 mcg of sufentanil. On the two subsequent study days, the dose was escalated, and each subject received a dosage form (comprising a slow-eroding formulation) containing 5 and 10 mcg of sufentanil.

Example 1B

All subjects received four repeated sublingual doses of a dosage form (comprising a slow-eroding formulation) containing 5 mcg of sufentanil administered at 10-minute intervals.

The slow-eroding sublingual sufentanil formulation containing 10 mcg sufentanil is provided below:

| Ingredient | Amount |
|---|---|
| Sufentanil Citrate | 0.27% |
| Mannitol (Pearlitol 200SD) | 73.77% |
| PEG 8000 | 14.98% |
| Polyox 303 | 3.00% |
| Lutrol F68 | 2.00% |
| Stearic Acid | 5.00% |
| Mg Stearate | 1.00% |
| Total | 100.00% |

The sufentanil plasma concentration at various time points following a single sublingual administration of a 2.5, 5, or 10 mcg sufentanil dosage form (slow-eroding) or 4 administrations of a 5 mcg sufentanil dosage form (slow-eroding) 10 minutes apart are shown in FIG. 1.

The mean sufentanil $t_{1/2}$ was similar for all of the sufentanil doses and varied from 1.56 hours (5 mcg sublingual dosage form) to 1.97 hours (10 mcg sublingual dosage form) with no obvious differences based on dose or route of administration (Table 1). The mean sufentanil $C_{max}$ and $AUC_{inf}$ increased with dose and were proportional to dose. The $T_{max}$ following a single sublingual administration of sufentanil ranged from 0.68 to 0.77 hours. The bioavailability following sublingual administration varied from 74.5% in subjects who were administered 5 mcg sufentanil dosage forms to 95.5% in subjects who were administered 10 mcg sufentanil dosage forms.

Table 1 provides a summary of pharmacokinetic parameters including $C_{max}$, $T_{max}$, $AUC_{inf}$, F and $t_{1/2}$. The $C_{max}$ after multiple sublingual dosing was 46.36 pg/mL. The mean $AUC_{inf}$ increased with multiple sublingual dosing of sufentanil and was generally proportional to dose when compared to single sublingual administration. The bioavailability of sufentanil following multiple sublingual dosing (97.2%) was greater than that following single administration at the same dose level (74.5%).

Figure 2:
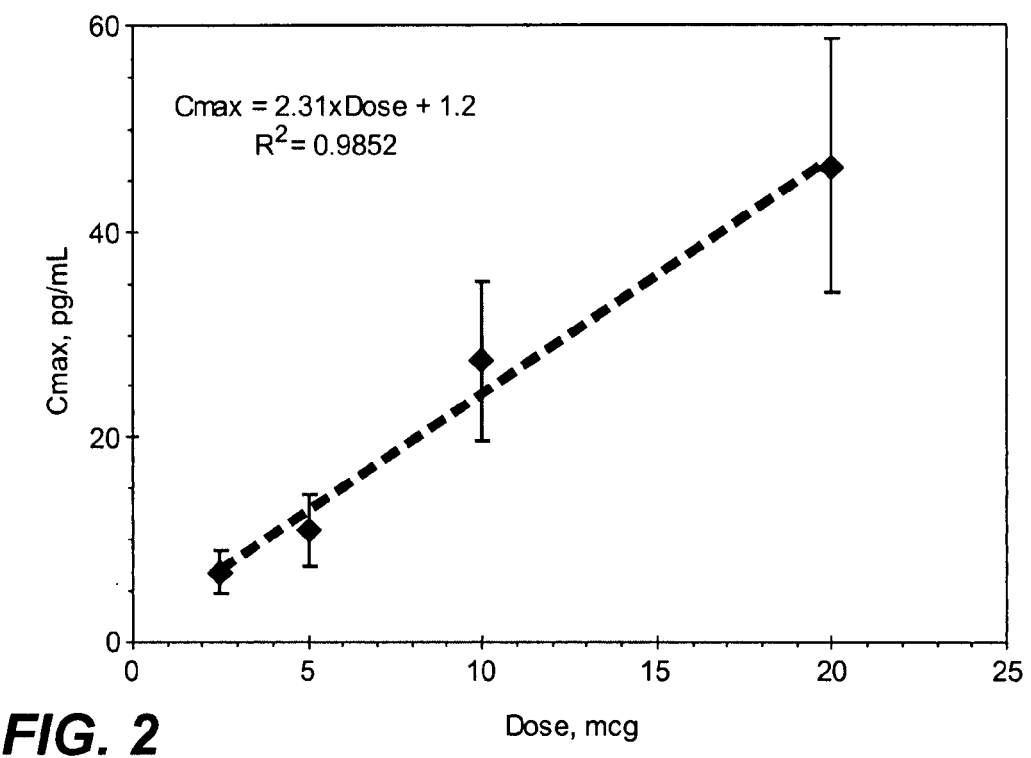
FIG. 2 is a graphic depiction of the linearity of $C_{max}$ (mean+/−SD) versus sufentanil dose (mcg), following sublingual administration of 2.5, 5, 10 or 4×5 mcg sufentanil dosage forms (slow-eroding) in healthy human volunteers.
Figure 3:
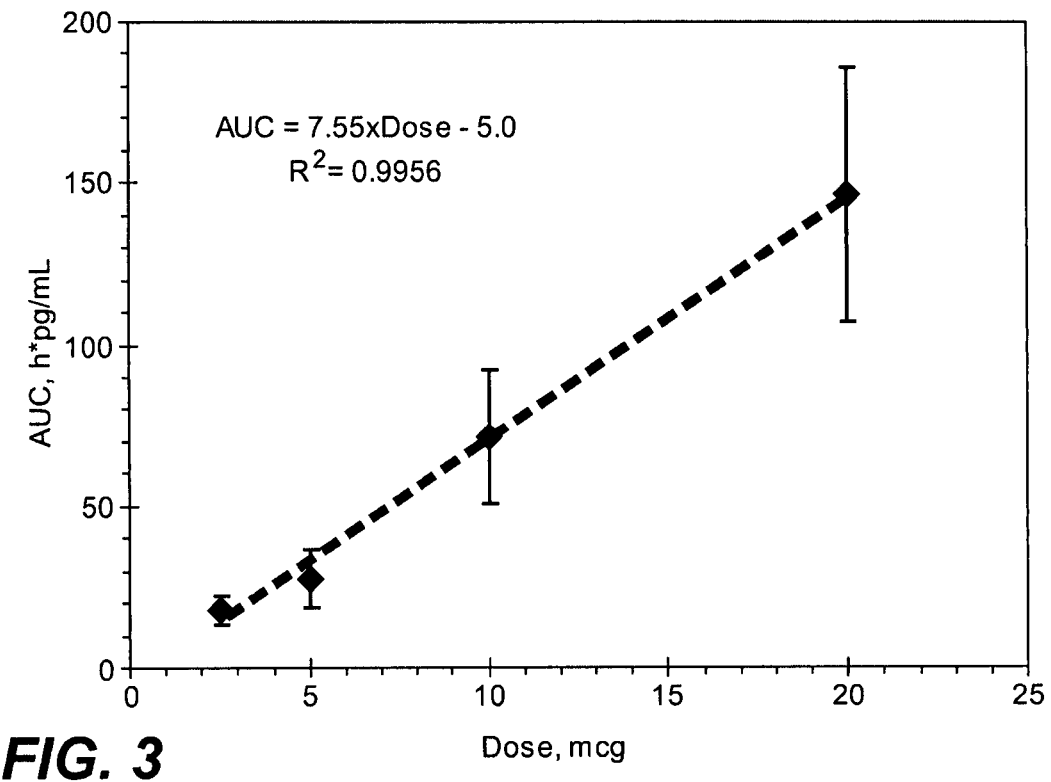
FIG. 3 is a graphic depiction of the linearity of $AUC_{inf}$ (mean+/−SD) versus sufentanil dose (mcg), following sublingual administration of 2.5, 5, 10 or 4×5 mcg sufentanil dosage forms (slow-eroding) in healthy human volunteers.

A paired t-test comparison of the mean sufentanil $C_{max}$ and $AUC_{inf}$ parameters was conducted after normalizing to the 10 mcg sublingual dose. The results are shown in Tables 2A and 2B. Results show that the $C_{max}$ and $AUC_{inf}$ were dose proportional from 2.5 to 10 mcg. Supporting data for dose-proportionality of the $C_{max}$ and $AUC_{inf}$ is shown in FIGS. 2 and 3, respectively.

TABLE 2A

Comparison of Sufentanil Pharmacokinetic Parameters Dose-Normalized to 10 mcg (2.5 mcg slow-eroding dosage forms)

| n = 12 | 2.5 mcg | 10 mcg | Difference | Standard deviation | t value | p value |
|---|---|---|---|---|---|---|
| $C_{max}$ (pg/mL) | 27.24 | 27.45 | −0.21 | 10.24 | −0.07 | 0.946 |
| $AUC_{inf}$ (hr*pg/mL) | 71.85 | 71.18 | −0.67 | 16.31 | 0.14 | 0.89 |

TABLE 2B

Comparison of Sufentanil Pharmacokinetic Parameters Dose-Normalized to 10 mcg 5 mcg slow-eroding dosage forms)

| n = 12 | 5 mcg | 10 mcg | Difference | Standard deviation | t value | p value |
|---|---|---|---|---|---|---|
| $C_{max}$ (pg/mL) | 21.81 | 27.45 | −5.65 | 10.99 | −1.78 | 0.10 |
| $AUC_{inf}$ (hr*pg/mL) | 54.85 | 71.18 | −16.33 | 17.94 | −3.15 | 0.009** |

**p value < 0.05, statistically significant

Figure 4:
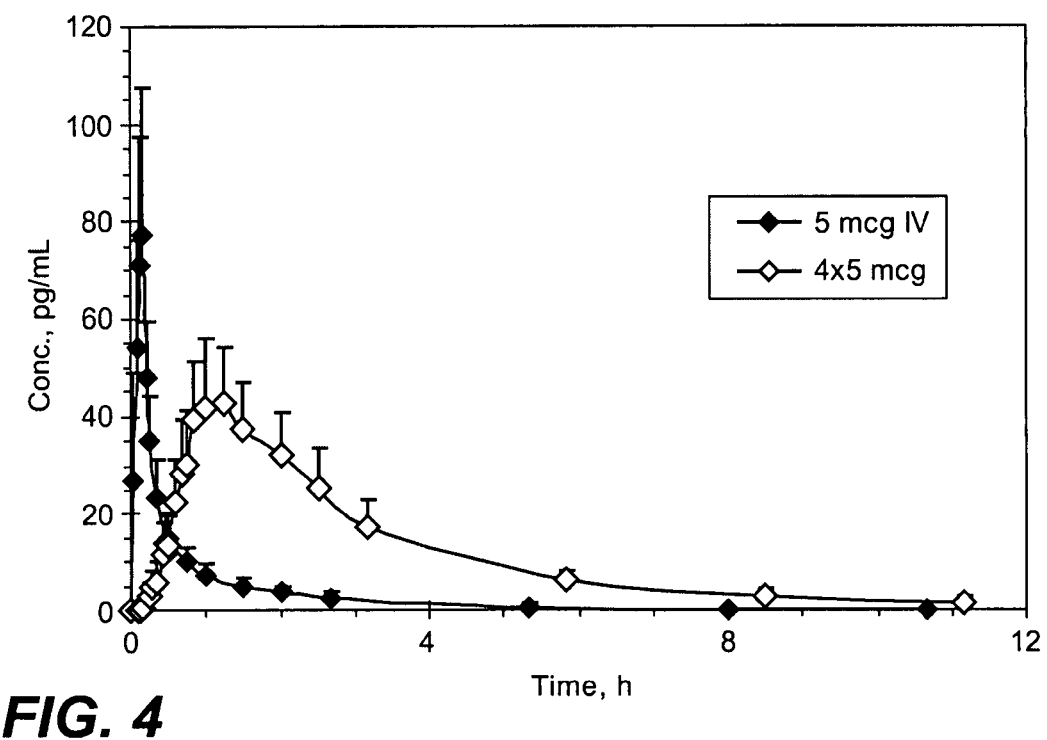
FIG. 4 is a graphic depiction of sufentanil plasma concentration (mean+/−SD) versus time, following repeated sublingual administration of four 5 mcg sufentanil dosage forms (slow-eroding) at 10 minute intervals in healthy human volunteers as compared to IV Infusion of 5 mcg sufentanil over 10 minutes.

Mean sufentanil plasma concentrations versus time (+/−SD) following repeated sublingual administration of 4×5 mcg sufentanil dosage forms (slow-eroding) at 10 minute intervals in healthy human volunteers as compared to IV Infusion of 5 mcg sufentanil over 10 minutes are shown in FIG. 4.

Figure 5A:
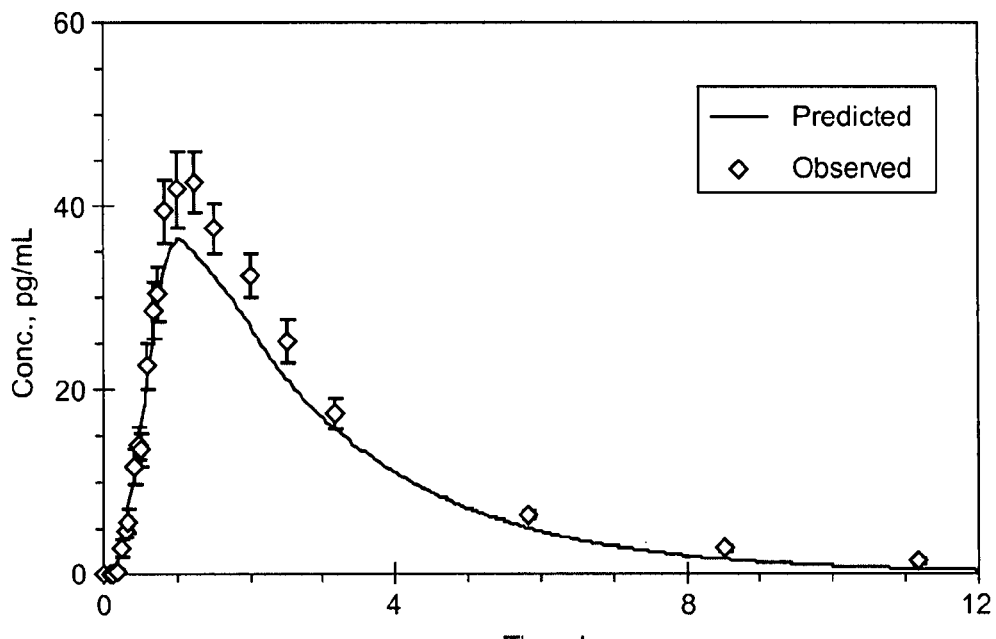
FIGS. 5A and 5B provide a graphic depiction of observed and predicted sufentanil plasma concentration (mean+/−SD) versus time, following repeated sublingual administration of 4×5 mcg sufentanil-dosage forms (slow-eroding) at 10 minute intervals in healthy human volunteers over a period of 12 hours (FIG. 5A) or a period of 2.5 hours (FIG. 5B).
Figure 5B:
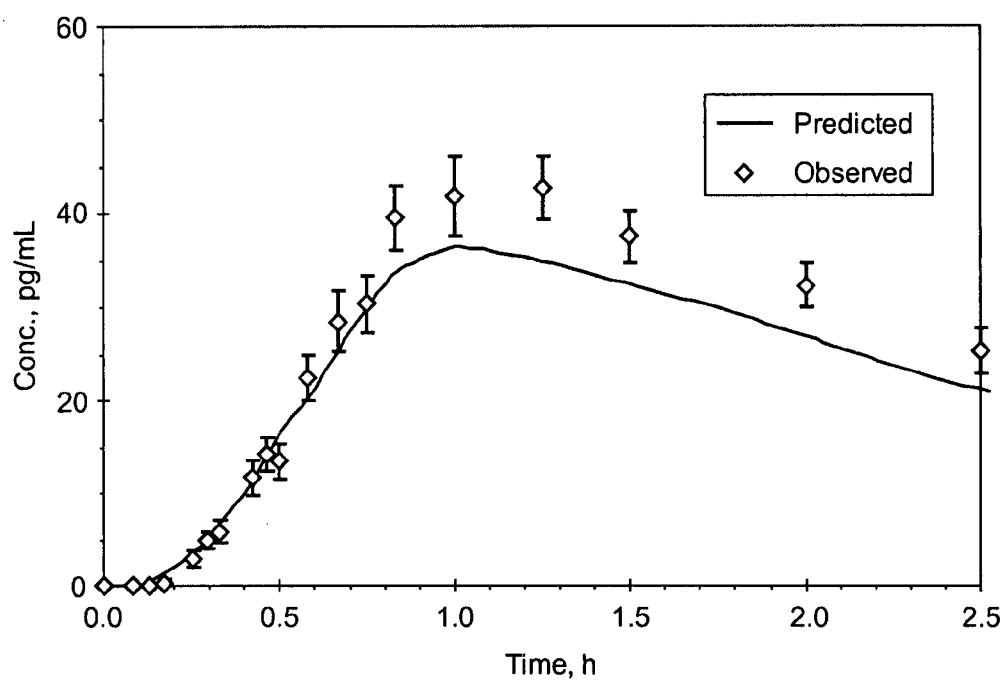

A simulation was used to estimate sufentanil plasma concentration following administration of 4×5 mcg sublingual sufentanil dosage forms (slow-eroding), administered 10 minutes apart. The simulation was conducted by superposition of the mean plasma concentration over time profile of a single administration of the 5 mcg sufentanil dosage form (slow-eroding). The simulation predicted and the observed mean (±SE) sufentanil plasma concentration versus time profiles were compared over a period of 12 hours (FIG. 5A) and a period of 2.5 hours (FIG. 5B). The predicted sufentanil concentrations based on the simulation closely tracks the observed sufentanil plasma concentration over time.

TABLE 1

Summary of Sufentanil Pharmacokinetic Parameters

| Parameter | | 5 mcg IV | 2.5 mcg | 5 mcg | 10 mcg | 4 × 5 mcg |
|---|---|---|---|---|---|---|
| $C_{max}$ | (pg/mL) | 81.3 ± 28.1 | 6.8 ± 2.1 | 10.9 ± 3.5 | 27.5 ± 7.7 | 46.4 ± 12.4 |
| $T_{max}$ | (hr) | 0.16 ± 0.03 | 0.73 ± 0.13 | 0.77 ± 0.29 | 0.68 ± 0.22 | 1.16 ± 0.23 |
| $AUC_{inf}$ | (hr*pg/mL) | 38.4 ± 8.5 | 18.0 ± 4.5 | 27.4 ± 9.1 | 71.2 ± 20.7 | 146.5 ± 39.1 |
| $t_{1/2}$ | (hr) | 1.66 ± 0.72 | 1.71 ± 0.51 | 1.56 ± 0.57 | 1.97 ± 0.85 | 3.29 ± 1.10 |
| F | (%) | — | 95.3 ± 19.1* | 74.5 ± 26.3* | 95.5 ± 29.2* | 97.2 ± 21.2* |

*% F calculated using 5 mcg IV AUC

Example 2

Further Evaluation of the Bioavailability and Pharmacokinetics of Sufentanil Following Sublingual Administration of a Small Volume Dosage Form

Example 2A

Subjects were administered 5 mcg of sufentanil solution via the sublingual route (N=2) or a 10-minute IV infusion of 5 mcg sufentanil (N=10), a single sublingual administration of a dosage form containing 10 mcg of sufentanil (faster-eroding formulation) and four repeated sublingual doses of a dosage form containing 10 mcg of sufentanil (faster-eroding formulation) administered at 20-minute intervals.

Example 2B

All subjects were administered a 20-minute IV infusion of 50 mcg sufentanil and a single sublingual administration of a dosage form containing 80 mcg of sufentanil (faster-eroding formulation).

The fast-eroding sublingual sufentanil formulation containing 10 mcg sufentanil is provided below:

| Component | Amount |
| --- | --- |
| Sufentanil Citrate | 0.26% |
| Mannitol SD100 | 70.64% |
| Di-Calcium Phosphate di-hydrate | 20.00% |
| HPMC K4M Premium CR | 3.00% |
| Stearic Acid | 5.00% |
| Mg Stearate | 1.00% |
| BHT | 0.10% |
| Total | 100.00% |

Figure 6:
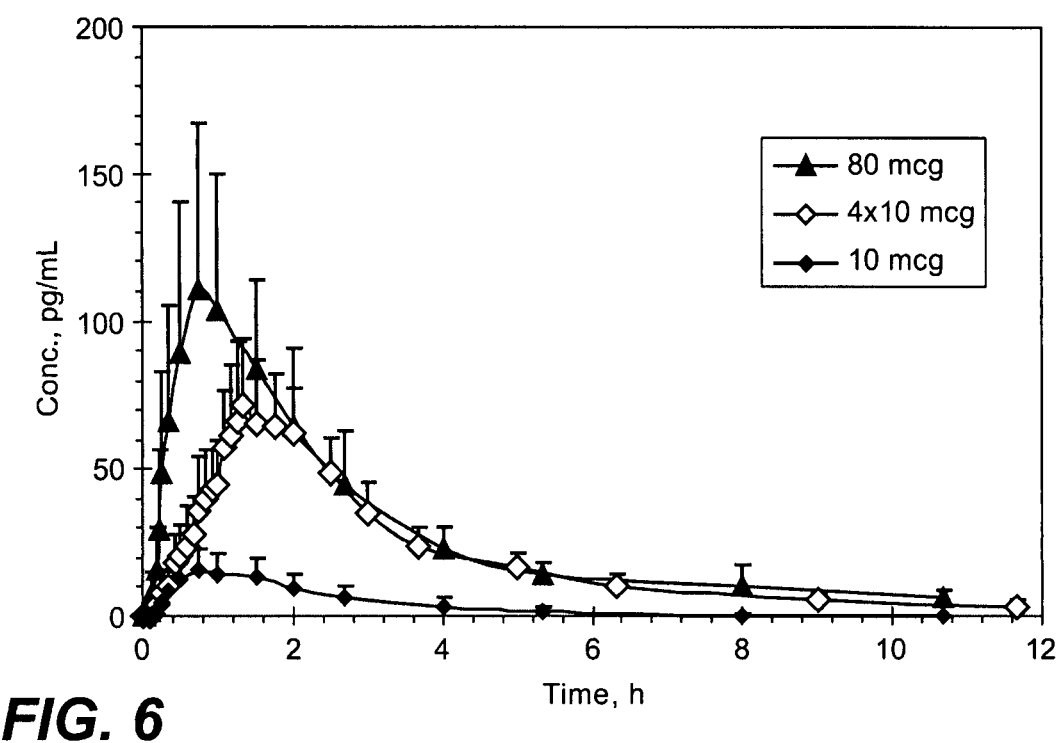
FIG. 6 is a graphic depiction of sufentanil plasma concentrations (mean+/−SD) versus time, following sublingual administration of 10, 40 (10 mcg every 20 minutes×4 doses) and 80 mcg sufentanil dosage forms (faster-eroding) in healthy human volunteers.

The sufentanil plasma concentration (mean+/−SD) at various time points following a single sublingual administration of 10 mcg and 80 mcg sufentanil dosage forms (faster-eroding) and 4 administrations of the 10 mcg sufentanil dosage form (faster-eroding) 20 minutes apart are shown in FIG. 6.

The mean $t_{1/2}$ was similar for the single sufentanil administrations and varied from 1.72 hours (5 mcg IV) to 1.67 hours (10 mcg sublingual). The mean sufentanil $AUC_{inf}$ increased with dose following single and multiple sublingual sufentanil administrations. The bioavailability was 60.9% in subjects treated with a single 10 mcg sublingual sufentanil dosage form (fast-eroding) and 87.8% following multiple (4×10 mcg) sublingual sufentanil administrations.

Figure 7A:
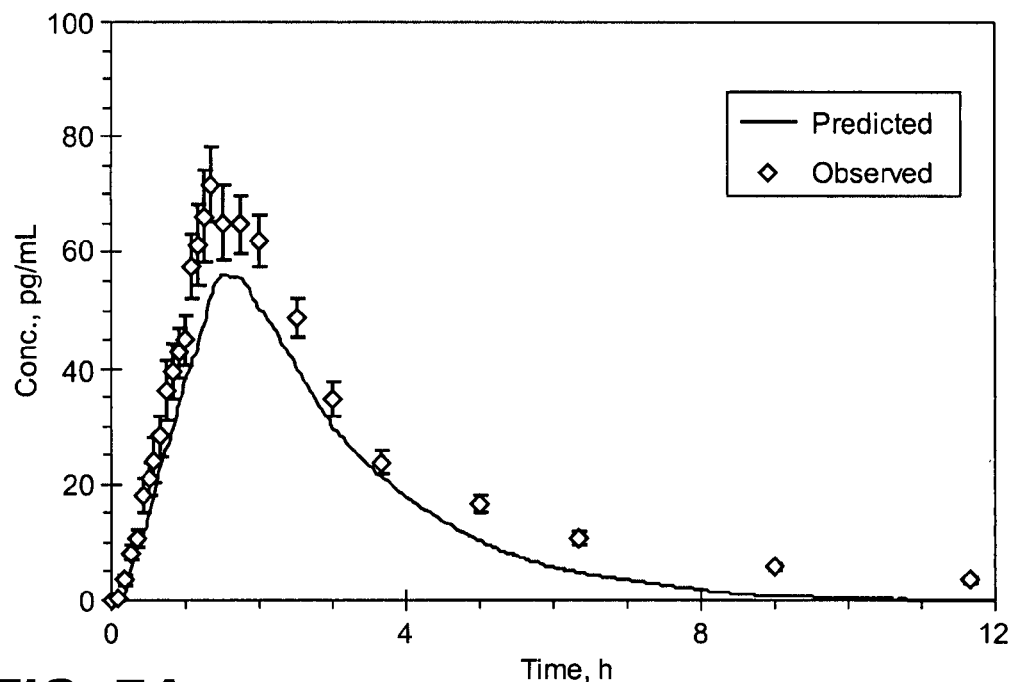
FIGS. 7A and 7B are a graphic depiction of observed and predicted sufentanil plasma concentration (mean+/−SD) versus time, following repeated sublingual administration of 4×10 mcg sufentanil dosage forms (faster-eroding) at 20 minute intervals in healthy human volunteers over a period of 12 hours (FIG. 7A) or a period of 2.5 hours (FIG. 7B).
Figure 7B:
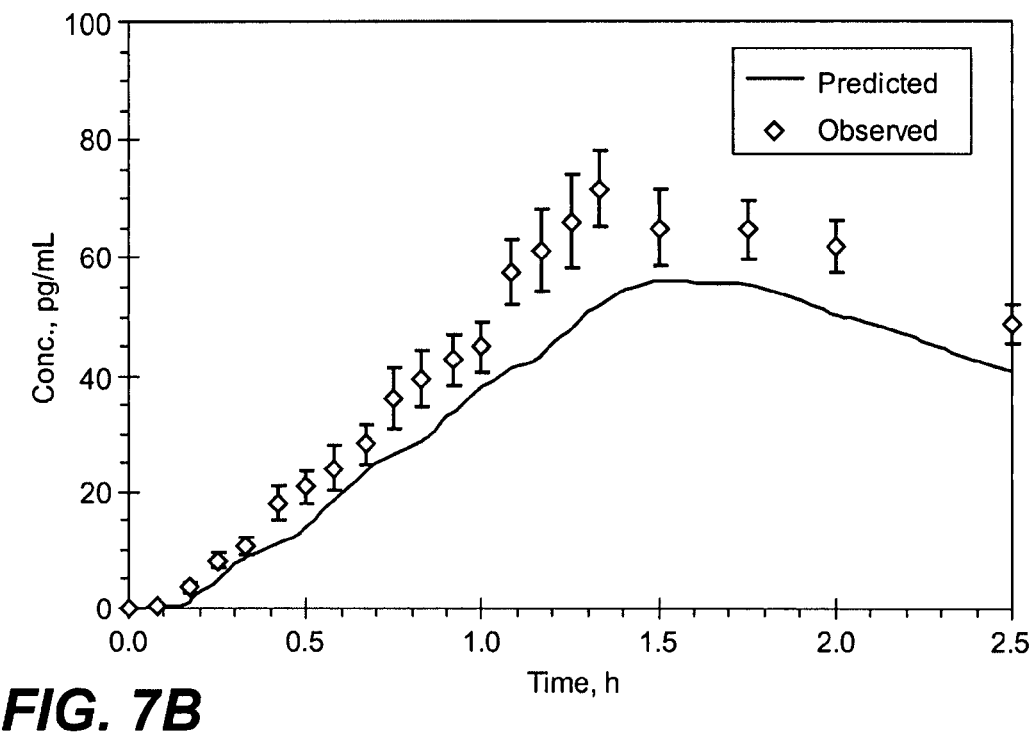

A simulation was used to estimate sufentanil plasma concentration following administration of 4×10 mcg sublingual sufentanil dosage forms (faster-eroding), administered 20 minutes apart. The simulation was conducted by superposition of the mean plasma concentration over time profile of a single administration of the 10 mcg sufentanil dosage form (faster-eroding). The simulation-predicted and the observed mean (±SE) sufentanil plasma concentration versus time profiles were compared over a period of 12 hours (FIG. 7A) and a period of 2.5 hours (FIG. 7B). The observed sufentanil plasma concentrations were greater than the predicted sufentanil plasma concentrations (based on the simulation) over time.

TABLE 3

Summary of Sufentanil Pharmacokinetic Parameters

| Parameter | | 5 mcg IV | 10 mcg | 4 × 10 mcg | 80 mcg | 50 mcg IV |
| --- | --- | --- | --- | --- | --- | --- |
| $C_{max}$ | (pg/mL) | 63.9 ± 28.2 | 16.5 ± 6.8 | 78.7 ± 20.1 | 127.2 ± 42.3 | 561.1 ± 277.7 |
| $T_{max}$ | (hr) | 0.17 ± 0.0 | 0.84 ± 0.35 | 1.41 ± 0.25 | 0.89 ± 0.35 | 0.34 ± 0.11 |
| $AUC_{inf}$ | (hr*pg/mL) | 39.4 ± 9.6 | 44.9 ± 24.6 | 253.4 ± 70.1 | 382.1 ± 88.2 | 528.0 ± 134.4 |
| $t_{1/2}$ | (hr) | 1.72 ± 0.47 | 1.67 ± 0.67 | 3.54 ± 1.02 | 4.23 ± 0.90 | 3.69 ± 0.78 |
| F | (%) | — | 60.9 ± 27.7* | 87.8 ± 22.2* | 70.1 ± 20.1* | — |

*% F calculated using 5 mcg IV AUC

The bioavailability following sublingual administration of the 80 mcg sufentanil dosage form (faster-eroding) was 70.1%.

Figure 8:
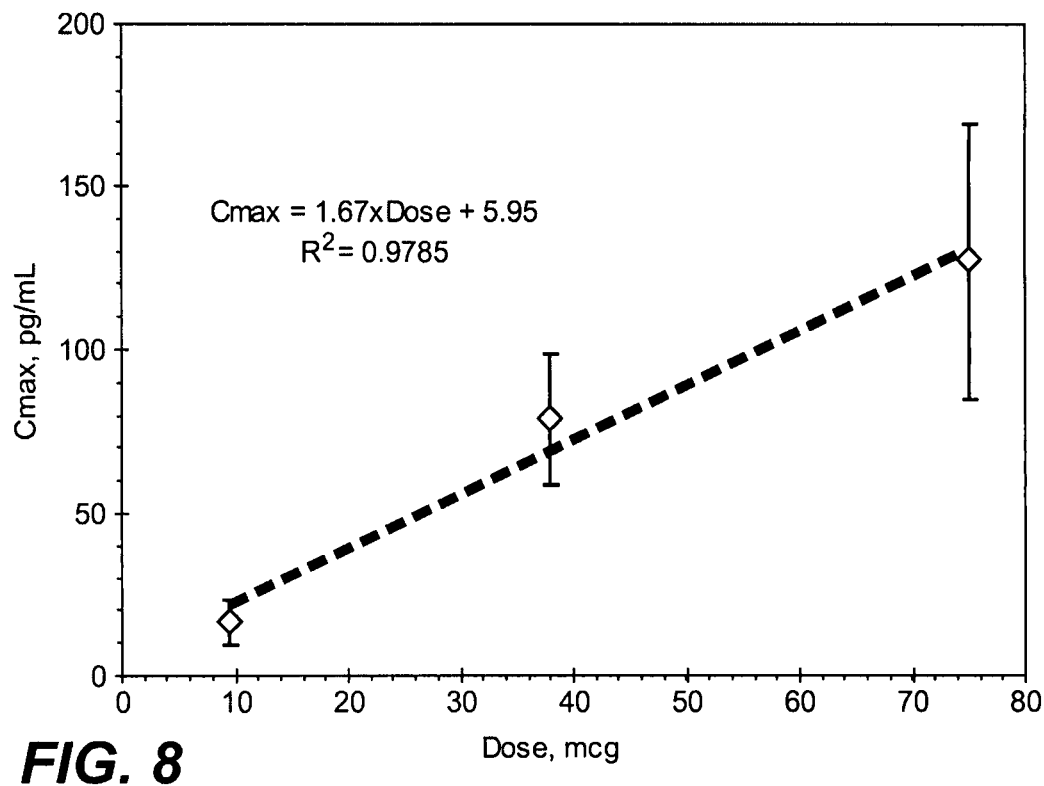
FIG. 8 is a graphic depiction of the linearity of $C_{max}$ (mean+/−SD) versus sufentanil dose (mcg), following sublingual administration of 10, 4×10 or 80 mcg sufentanil dosage forms (faster-eroding) in healthy human volunteers.
Figure 9:
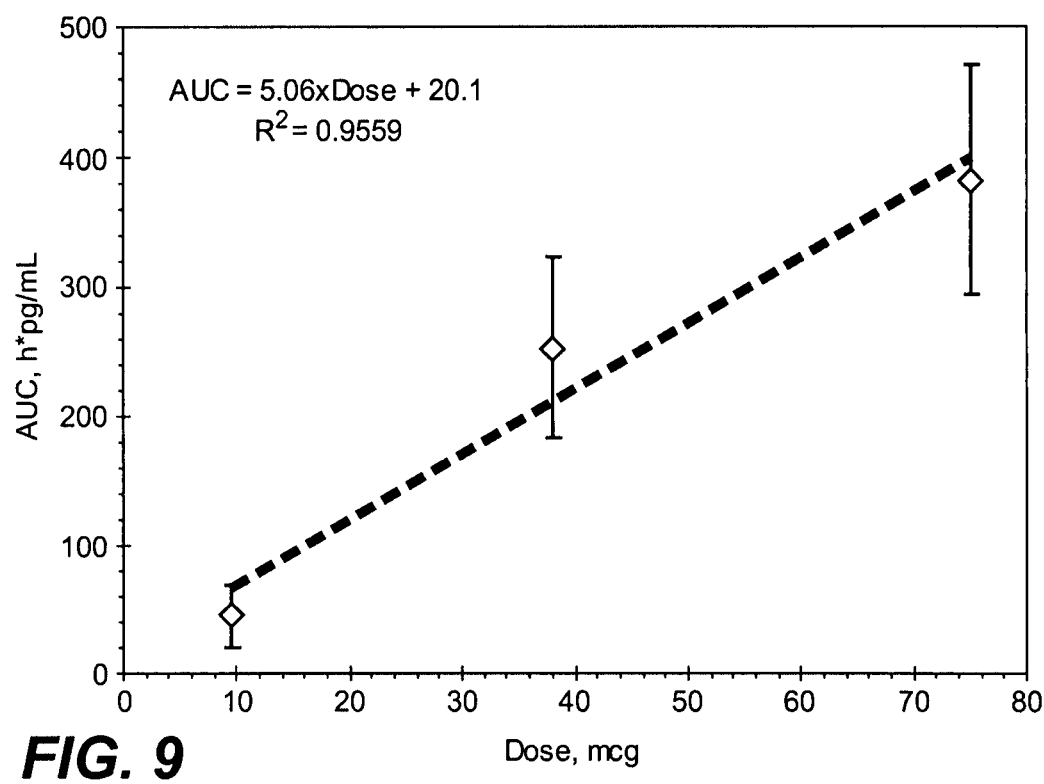
FIG. 9 is a graphic depiction of the linearity of $AUC_{inf}$ (mean+/−SD) versus sufentanil dose (mcg), following sublingual administration of 10, 4×10 or 80 mcg sufentanil dosage forms (faster-eroding) in healthy human volunteers.

A paired t-test comparison of the mean sufentanil $C_{max}$ and $AUC_{inf}$ parameters was conducted after normalizing to the 10 mcg sublingual dose. The results presented in Table 4 show that the $C_{max}$ and $AUC_{inf}$ were dose proportional from 10 to 80 mcg. Supporting data for dose-proportionality of the $C_{max}$ and $AUC_{inf}$ is shown in FIGS. 8 and 9, respectively.

TABLE 4

Comparison of Sufentanil Pharmacokinetic Parameters Dose-Normalized to 10 mcg (80 mcg faster-eroding dosage forms)

| n = 11 | 10 mcg | 80 mcg | Difference | Standard deviation | t value | p value |
| --- | --- | --- | --- | --- | --- | --- |
| $C_{max}$ (pg/mL) | 16.59 | 16.93 | −0.34 | 8.04 | −0.14 | 0.89 |
| $AUC_{inf}$ (hr*pg/mL) | 45.02 | 50.88 | −5.86 | 23.85 | −0.81 | 0.43 |

Figure 10A:
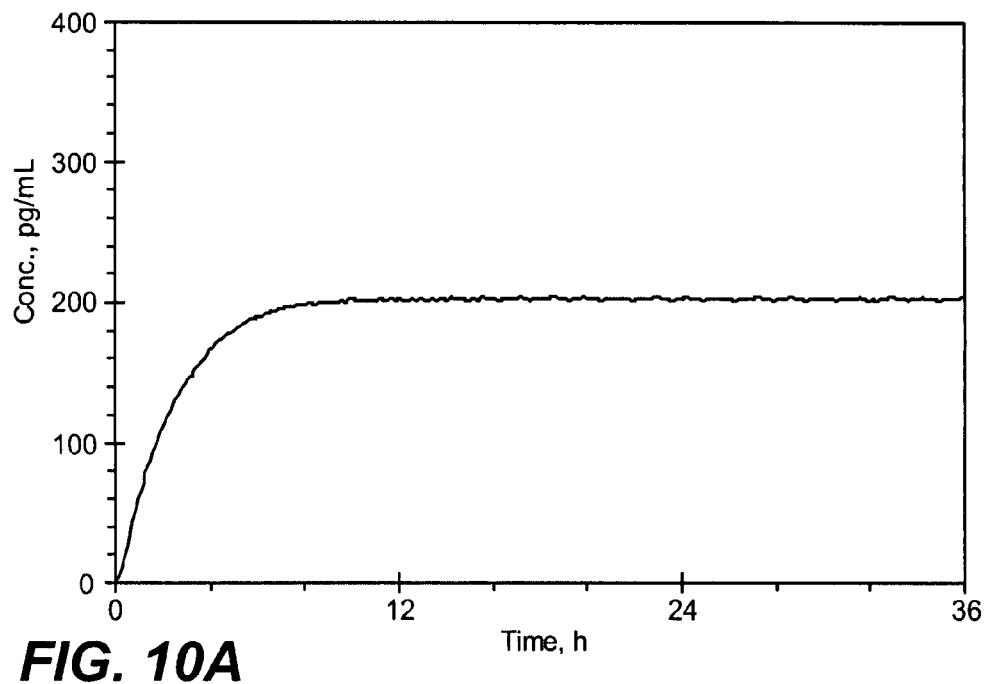
FIGS. 10A and 10B provide a graphic depiction of steady-state sufentanil plasma concentration versus time predicted by superposition following repeated sublingual administration of 10 mcg doses of sufentanil at 20 minute intervals (FIG. 10A) or 15 mcg doses of sufentanil at 20 minute intervals (FIG. 10B).
Figure 10B:
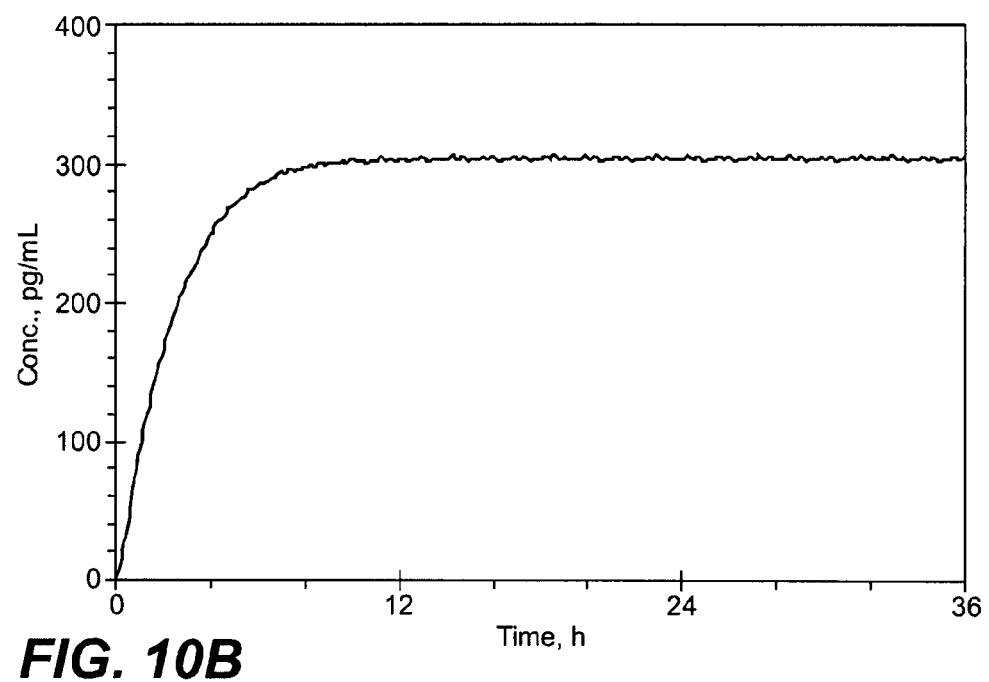

A simulation of sufentanil concentrations following multiple administrations of 10 or 15 mcg sublingual sufentanil dosage forms (slow-eroding), administered every 20 minutes was carried out. Dosage forms comprising the slow-eroding formulation resulted in a bioavailability of greater than 95%, and therefore serve as a basis for an estimate of the highest predicted steady-state sufentanil concentration following multiple administrations of 10 or 15 mcg sublingual sufentanil dosage forms. Steady-state sufentanil concentrations can be reached in about 12 hours after repeated sublingual doses at 20 minute intervals. The simulation predicted steady-state sufentanil concentrations of 200 pg/mL for administration of 10 mcg of sufentanil at 20 minute intervals and 300 pg/mL for administration of 15 mcg of sufentanil at 20 minute intervals as shown in FIGS. 10A and 10B, respectively. The simulations suggest that a minimal re-dosing interval of 20 minutes is safe.

Example 3

Acute Pain Management in the Outpatient Setting by Administering a Sufentanil-Containing Dosage Form Using a Device A pharmacist loads a drug dispensing device with a drug cartridge which includes 40 sufentanil dosage forms. Each cartridge has two colored initialization tablets (called "shipping tablets") arranged to be the first two tablets dispensed. The device has a means for loading the cartridge, which is either a port, hatch, or door that is secure and inaccessible to unauthorized users. Once the pharmacist has loaded the cartridge into the device, he locks the device access port, hatch or door. The pharmacist then docks the dispensing device for the first time to a dock that is connected to a personal or other computer, using the docking connector, and then programs the device. Programming involves uploading the dosage strength of the dosage forms, the number of dosage forms loaded in the device, the prescribed frequency of dosage form usage, the number of dosage forms to be used per day, the current date and time, the preferred language, a valid thumbprint or other identification for identifying the patient, and the physician's identification information, in case the device is lost and found.

Once the dispensing device is programmed, the pharmacist demonstrates proper usage and tests the device by dispensing a single shipping tablet. The pharmacist then gives the dispensing device to the patient and observes the patient dispense a shipping tablet to ensure proper usage and functionality. Along with the dispensing device, the pharmacist provides the patient with a radio frequency identification (RFID) tag that must be within approximately 5 inches of the device to allow the dispensing device to operate.

When the patient wants to administer a dose of the drug, he or she will hold the dispensing device, and push any button to wake the device up from its sleep mode. The device will query the user for either a thumbprint reading or a personal identification number (PIN). The device will then search for a validated RFID key within range. Once these conditions are met, the dispensing device will query its internal memory and clock to make sure that the dosage regimen programmed by the pharmacist is not being violated by the current usage request. At this point the device displays status information, such as the date and time, the number of doses left, the last time a dosage was used, the patient's name, etc., and the pharmacist informs the patient that the device is ready to dispense the dosage forms by a visual and/or audible signal.

The patient will hold the dispensing end of the device under his or her tongue and press the dispensing lever. When the dosage form is dispensed a tone will sound to inform the patient that the dosage form was properly delivered. At this point the device will lock down to prevent further dispensing until the preprogrammed lock-out time has passed, at which time the device will be ready to use again.

Example 4

Acute Pain Management in the Inpatient Setting by Administering a Sufentanil-Containing Dosage Form Using a Device A post operative patient requires acute pain treatment following surgery. The surgeon prescribes oral transmucosal sufentanil to be administered using the drug dispensing device. The attending nurse takes the prescription order to the pharmacist or automated pharmaceutical inventory management system (e.g. Pyxis) and obtains a sufentanil-containing drug cartridge for sublingual delivery. The cartridge is labeled and equipped with an RFID electronic tag containing drug label information. The cartridge is labeled and equipped with an RFID electronic tag containing drug label information.

The nurse then takes a disposable dispensing portion of the drug dispensing device from inventory, and proceeds to a base station to obtain a reusable controller portion of the drug dispensing device that has completed its recharge cycle and is ready for use. The nurse inserts the drug cartridge into the disposable dispensing portion, and then affixes this to the reusable controller portion of the drug dispensing device and locks the disposable portion into the reusable portion of the drug dispensing device. At this point the device reads the RFID tag on the drug cartridge and uploads the appropriate drug information, including the type of drug, the dosage strength, the programmed lockout period between doses, etc. The nurse confirms the proper drug cartridge information has been read by the drug dispensing device and gives the drug dispensing device to the patient for patient controlled dispensing of the pain medication.

When the patient requires pain medication, she takes the drug dispensing device in her hand, and places the dispensing tip in her mouth, under her tongue and presses the dispense button. The drug dispensing device then does an internal check to ensure that the proper lockout period has elapsed since the last dosage dispense. At this point the drug dispensing device dispenses a dosage form under the patient's tongue and provides feedback that dosing was successful. The patient removes the drug dispensing device from her mouth and allows the sublingual dosage form to dissolve under her tongue. The patient may attempt to dispense as frequently as she desires, but the drug dispensing device will only allow successful dosing after the appropriate lockout period has elapsed. The drug dispensing device electronically logs the dispensing attempts and successful dispenses in its dosing history.

Periodically the nurse checks on the patient and drug dispensing device. During such checks, the nurse inspects the drug dispensing device to see that there are no errors and to check the number of remaining dosage forms in the drug dispensing device, and returns it to the patient.

When the patient is discharged, the nurse takes the drug dispensing device and unlocks the reusable portion from the disposable portion, disposes of the cartridge and disposable portion of the drug dispensing device. The nurse then connects the reusable portion of the device to a computer and uploads the patient use information from the drug dispensing device to the computer for input into the patient's medical records. The nurse cleans the reusable controller portion and returns it to the base station for recharging.

Example 5

Acute Pain Management in the Inpatient Setting by Administering a Sufentanil-Containing Dosage Form Using a Device and a Portable Dock A post operative patient requires acute pain treatment following surgery. The surgeon prescribes oral transmucosal sufentanil to be administered using the drug dispensing device. The attending nurse takes the prescription order to the pharmacist or automated pharmaceutical inventory management system (e.g. Pyxis) and obtains a sufentanil-containing drug cartridge for sublingual delivery. The cartridge is labeled and equipped with an RFID electronic tag containing drug label information. The cartridge is labeled and equipped with an RFID electronic tag containing drug label information. The cartridge includes a shipping tablet or initialization tablet in the first to be dispensed location of the dosage form stack.

The nurse then takes a disposable dispensing portion of the drug dispensing device from inventory, and proceeds to a base station to obtain a reusable controller portion of the drug dispensing device that has completed its recharge cycle and is ready for use. The nurse inserts the drug cartridge into the disposable dispensing portion, and then affixes this to the reusable controller portion of the drug dispensing device. Next, the nurse takes a portable dock (or docking FOB) from the base station where it has been recharging, and docks the assembled drug dispensing device to the portable dock. The portable dock and the assembled drug dispensing device communicate electronically and a setup menu comes up on the portable dock for setting up the drug dispensing device.

At this point the device locks the reusable and disposable portions together, reads the RFID tag on the drug cartridge and uploads the appropriate drug information, including the type of drug, the dosage strength, the lockout period between doses, etc. The dispensing device writes a code to the RFID tag on the cartridge identifying it as a used cartridge. The nurse enters her fingerprint in the fingerprint reader on the portable dock to gain secured access and proceeds to set up the drug dispensing device for use. The set up procedure includes entering patient identification, the nurse's identification, confirming the proper time on the device, and confirming the proper drug cartridge information. The nurse then takes a disposable RFID bracelet and places this adjacent to the drug dispensing device at which point the drug dispensing device reads the tag and the nurse confirms that the proper bracelet tag has been read.

The nurse then confirms proper setup of the drug dispensing device by pressing the dispensing button once. The drug dispensing device actuates, dispensing the shipping tablet facsimile into the nurses hand, confirming proper operation. The drug dispensing device detects the dispensing of the shipping tablet, allowing for an internal system check of proper operation and internal calibration of the newly assembled system. If the internal dispensing check is successful, the portable dock queries the nurse to confirm that the shipping table was properly dispensed, and the nurse confirms the proper setup. The nurse then disengages the drug dispensing device from the portable dock, and proceeds to the patient's bedside for the final steps of setup.

The nurse places the RFID bracelet on the patient's wrist and affixes a theft resistant tether to the patient's bed and the other end to the drug dispensing device. The nurse then instructs the patient on proper use of the sublingual drug dispensing device, and gives the drug dispensing device to the patient for patient controlled dispensing of sufentanil.

When the patient requires pain medication, she takes the drug dispensing device in her hand, and places the dispensing tip in her mouth, under her tongue and presses the dispensing button. The drug dispensing device then does an internal check to ensure that the proper lockout period has elapsed since the last dosage dispense, and that the patient's RFID bracelet is present and readable. At this point the drug dispensing device dispenses a dosage form under the patient's tongue and provides a feedback that dosing was successful. The patient removes the drug dispensing device from her mouth and allows the sublingual dosage form to dissolve under her tongue. The patient may attempt to dispense as frequently as she desires, but the drug dispensing device will only allow successful dosing after the appropriate lockout period has elapsed. The drug dispensing device electronically logs the dispensing attempts and successful dispenses in its dosing history.

Periodically the nurse checks on the patient and device. During such a patient check in the nurse brings a portable docking FOB and docks the device to the FOB. The electronic connection enables the nurse to download the information from the drug dispensing device to the FOB. This information includes the use history, drug information, number of remaining dosage forms and duration of use since initial set up. The nurse then enters her fingerprint in the finger print scanner to gain access to the information and to drug dispensing device. Because the patient is requiring an additional dose of drug prior to the lockout period expiring, the nurse overrides the lockout period and then returns the drug dispensing device to the patient at which point the patient is able to take another dose.

The nurse leaves the patient's room with the portable docking FOB and returns to the nurse's station to record the dosing history in the patient's records. When finished the nurse returns the FOB to the base station for recharging.

When the patient has used all of the dosage forms in the drug dispensing device, the nurse brings the portable docking FOB into the patient's room and docks the drug dispensing device to the FOB. The nurse then enters her fingerprint in the fingerprint scanner on the FOB to gain secured access to the drug dispensing device. Next, the nurse unlocks the security tether and disconnects the drug dispensing device from the bed. She then unlocks the drug dispensing device and removes it from the FOB for disassembly. The nurse disconnects the disposable portion from the reusable portion, and removes the cartridge from the disposable portion. The nurse disposes of the disposable portion and the cartridge, and wipes the reusable controller portion with an antiseptic wipe to clean it before returning it to the base station. The reusable controller portion requires that the nurse return it to the base station where it recharges and runs an internal diagnostic test before being ready for use again.

The nurse then proceeds to set up a new drug dispensing device as described above and provides this to the patient.

Although the foregoing invention has been described in some detail by way of illustration and example for purposes of clarity and understanding, it will be apparent to those skilled in the art that certain changes and modifications may be practiced. Various aspects of the invention have been achieved by a series of experiments, some of which are described by way of the following non-limiting examples. Therefore, the description and examples should not be construed as limiting the scope of the invention, which is delineated by the appended description of exemplary embodiments.

What is claimed is:

1. A method of treating pain by administering a tablet to the oral mucosa of a subject, said tablet comprising from about 5 to about 100 micrograms (mcg) of sufentanil expressed as the base and a bioadhesive material, wherein: (i) said tablet adheres to the oral mucosa during the period of drug delivery; (ii) said tablet has a volume of less than 30 microliters or a mass of less than 30 mg; (iii) said tablet provides a dose-normalized mean Cmax of 1.59-2.75 pg/mL per mcg dosed; and (iv) said tablet delivers a majority of the total amount of sufentanil in said tablet via the transmucosal route.

2. A method of treating pain by administering a tablet according to claim 1, wherein a single sublingual administration of said tablet to a subject results in a bioavailability of greater than 50%.

3. A method of treating pain by administering a tablet according to claim 1, wherein a single sublingual administration of said tablet to a subject results in a $T_{max}$ with a coefficient of variation of less than 40%.

4. The method of treating pain according to claim 1, wherein a single sublingual administration of said tablet to a subject results in a mean $T_{max}$ of from 0.68 to 0.89 hours.

5. A method of treating pain by administering a tablet according to claim 1, using a handheld dispensing device for placement of said tablet in the sublingual space.

6. The method of claim 5, wherein said tablet administration is patient controlled.

7. The method of claim 5, wherein said dispensing device comprises a housing having a dispensing end with a means to prevent or retard saliva ingress and a lock-out feature.

8. The method of claim 7, wherein said lock-out feature provides for repeated sublingual administration of sufentanil at a minimum interval of 20 minutes.

9. The method of claim 7, wherein said device further comprises a patient identification feature.

10. The method of claim 7, wherein said dispensing device further comprises a disposable cartridge which holds sufficient drug tablets to provide 48 to 72 hours of treatment.

11. The method of claim 10, wherein said cartridge includes a recognition system comprising a physical keyed feature on the cartridge, an optically detected feature or pattern, a bar code on the cartridge, a magnetic tag on the cartridge, an RFID tag on the cartridge, an electronic microchip on the cartridge, or a combination thereof which allows a dispensing device to recognize said cartridge.

12. The method of claim 1, wherein said tablet comprises a dose of sufentanil, expressed as the base, selected from the group consisting of 5 mcg, 10 mcg, 15 mcg, 20 mcg, 30 mcg, 40 mcg, 50 mcg, 60 mcg, 70 mcg, 80 mcg and 100 mcg.

13. The method of claim 12, wherein said tablet comprises a 5 mcg dose of sufentanil expressed as the base.

14. The method of claim 12, wherein said tablet comprises a 10 mcg dose of sufentanil expressed as the base.

15. The method of claim 12, wherein said tablet comprises a 15 mcg dose of sufentanil expressed as the base.

16. The method of claim 12, wherein said tablet comprises a 20 mcg dose of sufentanil expressed as the base.

17. The method of claim 1, wherein erosion of said tablet is complete in from about 6 minutes to about 25 minutes following sublingual administration to said subject.

18. The method of claim 1, wherein said tablet delivers at least 55% of the total amount of sufentanil in said tablet via the transmucosal route.

19. The method of claim 16, wherein said tablet delivers at least 65% of the total amount of sufentanil in said tablet via the transmucosal route.

20. The method of claim 16, wherein said tablet delivers at least 75% of the total amount of sufentanil in said tablet via the transmucosal route.

21. The method of claim 1, wherein following administration of said tablet there is a linear relationship between $C_{max}$ and the amount of sufentanil in said tablet.

22. The method of claim 13, wherein following administration of said dosage form there is a linear relationship between $AUC_{inf}$ and the amount of sufentanil in said tablet.

23. The method of claim 1, wherein repeated sublingual administration of said tablet to a subject results in a $T_{max}$ with a coefficient of variation of less than 40%.

24. A method of treating pain by administering a tablet to the oral mucosa of a subject, said tablet comprising from about 5 to about 100 micrograms (mcg) of sufentanil expressed as the base and a bioadhesive material, wherein: (i) said tablet adheres to the oral mucosa during the period of drug delivery; (ii) said tablet has a volume of less than 30 microliters or a mass of less than 30 mg; and (iii) said tablet provides a mean Tmax of from 0.68 to 0.89 hours.

25. A method of treating pain by administering a tablet according to claim 24, wherein a single sublingual administration of said tablet to a subject results in a bioavailability of greater than 50%.

26. A method of treating pain by administering a tablet according to claim 24, wherein a single sublingual administration of said tablet to a subject results in a $T_{max}$ with a coefficient of variation of less than 40%.

27. The method of treating pain according to claim 24, wherein a single sublingual administration of said tablet provides a dose-normalized mean $C_{max}$ of 1.59-2.75 pg/mL per mcg dosed.

28. The method of treating pain according to claim 24, wherein said tablet delivers at least 55% of the total amount of sufentanil in said tablet via the transmucosal route.

29. The method of claim 24, wherein said tablet comprises a dose of sufentanil, expressed as the base, selected from the group consisting of 5 mcg, 10 mcg, 15 mcg, 20 mcg, 30 mcg, 40 mcg, 50 mcg, 60 mcg, 70 mcg, 80 mcg and 100 mcg.

30. A method of treating pain by administering a tablet to the oral mucosa of a subject, said tablet comprising from about 5 to about 100 micrograms (mcg) of sufentanil expressed as the base and a bioadhesive material, wherein: (i) said tablet adheres to the oral mucosa during the period of drug delivery; (ii) said tablet has a volume of less than 30 microliters or a mass of less than 30 mg; and (iii) said tablet delivers at least 55% of the total amount of sufentanil in said tablet via the transmucosal route.

31. The method of treating pain according to claim 30, wherein a single sublingual administration of said tablet provides a dose-normalized mean Cmax of 1.59-2.75 pg/mL per mcg dosed.

32. The method of claim 30, wherein a single sublingual administration of said tablet to a subject results in a mean Tmax of from 0.68 to 0.89 hours.

33. A method of treating pain by administering a tablet according to claim 30, wherein a single sublingual administration of said tablet to a subject results in a bioavailability of greater than 50%.

34. A method of treating pain by administering a tablet according to claim 30, wherein a single sublingual administration of said tablet to a subject results in a $T_{max}$ with a coefficient of variation of less than 40%.

35. The method of claim 30, wherein said tablet comprises a dose of sufentanil, expressed as the base, selected from the group consisting of 5 mcg, 10 mcg, 15 mcg, 20 mcg, 30 mcg, 40 mcg, 50 mcg, 60 mcg, 70 mcg, 80 mcg and 100 mcg.

* * * * *